US008916652B2

(12) United States Patent
Dalsin et al.

(10) Patent No.: US 8,916,652 B2
(45) Date of Patent: Dec. 23, 2014

(54) MULTI-ARMED CATECHOL COMPOUND BLENDS

(75) Inventors: Jeffrey L. Dalsin, Verona, WI (US); Bruce P. Lee, Houghton, MI (US); Laura Vollenweider, Lodi, WI (US); Sunil Silvary, Madison, WI (US); John L. Murphy, Verona, WI (US); Fangmin Xu, Sudbury, MA (US); Amanda Spitz, Madison, WI (US); Arinne Lyman, Fitchburg, WI (US)

(73) Assignee: Kensey Nash Corporation, Exton, PA (US)

( * ) Notice: Subject to any disclaimer, the term of this patent is extended or adjusted under 35 U.S.C. 154(b) by 368 days.

(21) Appl. No.: 13/400,333

(22) Filed: Feb. 20, 2012

(65) Prior Publication Data

US 2012/0149849 A1 Jun. 14, 2012

Related U.S. Application Data

(63) Continuation of application No. 12/568,542, filed on Sep. 28, 2009, now Pat. No. 8,119,742.

(60) Provisional application No. 61/100,742, filed on Sep. 28, 2008, provisional application No. 61/150,471, filed on Feb. 6, 2009.

(51) Int. Cl.
| | | |
|---|---|---|
| *C08L 21/02* | (2006.01) | |
| *A61L 29/14* | (2006.01) | |
| *A01N 37/38* | (2006.01) | |

(Continued)

(52) U.S. Cl.
CPC ............... *A01N 47/12* (2013.01); *A61L 29/145* (2013.01); *A01N 37/38* (2013.01); *A61L 29/14* (2013.01); *A61L 31/10* (2013.01); *A61L 24/04* (2013.01); *A61B 17/08* (2013.01); *A61L 31/145* (2013.01); *C09J 171/02* (2013.01); *A61B 17/06166* (2013.01); *A61L 15/46* (2013.01); *A61L 31/16* (2013.01); *C08G 65/3317* (2013.01); *A61L 15/60* (2013.01); *A01N 37/40* (2013.01); *A61L 27/52* (2013.01); *A61B 2017/00951* (2013.01); *C09D 5/1637* (2013.01); *A61L 27/34* (2013.01); *A61B 17/064* (2013.01); *A61F 2002/0086* (2013.01);

(Continued)

(58) Field of Classification Search
USPC .......................................... 525/408; 527/200
See application file for complete search history.

(56) References Cited

U.S. PATENT DOCUMENTS 5,550,177 A * 8/1996 Fanta et al. ...................... 524/47
5,550,188 A 8/1996 Rhee et al.

(Continued)

FOREIGN PATENT DOCUMENTS

WO 03/008376 1/2003
WO 2005-118831 12/2005

OTHER PUBLICATIONS

Nektar Advanced PETylation Catalog 2005-2006, pp. 1-34.*

(Continued)

*Primary Examiner* — Alicia Bland
(74) *Attorney, Agent, or Firm* — Kirk J. Hogan; Casimir Jones S.C.

(57) ABSTRACT

The invention describes families of compounds that utilize multihydroxyl phenyl groups to provide adhesive properties. Selection of the multihydroxy phenyl group along with linkers or linking groups and the linkages between the linkers or linking groups with polyalkylene oxides, provides materials that can be engineered to afford controllable curing time, biodegradation and/or swelling.

12 Claims, 28 Drawing Sheets

(51) Int. Cl.

| | | |
|---|---|---|
| A61L 31/10 | (2006.01) | |
| A61L 24/04 | (2006.01) | |
| A61B 17/08 | (2006.01) | |
| A61L 31/14 | (2006.01) | |
| C09J 171/02 | (2006.01) | |
| A61L 15/46 | (2006.01) | |
| A61L 31/16 | (2006.01) | |
| C08G 65/331 | (2006.01) | |
| A61L 15/60 | (2006.01) | |
| A01N 37/40 | (2006.01) | |
| A61L 27/52 | (2006.01) | |
| C09D 5/16 | (2006.01) | |
| A61L 27/34 | (2006.01) | |
| A61L 15/44 | (2006.01) | |
| A61L 27/54 | (2006.01) | |
| A61L 29/16 | (2006.01) | |
| A01N 47/28 | (2006.01) | |
| A61L 27/50 | (2006.01) | |
| A61L 29/08 | (2006.01) | |
| A01N 47/12 | (2006.01) | |
| A61L 15/42 | (2006.01) | |
| A01N 37/44 | (2006.01) | |
| C08G 65/333 | (2006.01) | |
| A61B 17/06 | (2006.01) | |
| A61B 17/00 | (2006.01) | |
| A61B 17/064 | (2006.01) | |
| A61F 2/00 | (2006.01) | |

(52) U.S. Cl.
CPC ............... *A61L 15/44* (2013.01); *A61L 27/54* (2013.01); *A61L 29/16* (2013.01); *A01N 47/28* (2013.01); *A61L 27/50* (2013.01); *A61L 29/085* (2013.01); *A61L 15/42* (2013.01); *A61F 2/0063* (2013.01); *C08L 2203/02* (2013.01); *A61B 17/085* (2013.01); *A01N 37/44* (2013.01); *C08G 65/33396* (2013.01); *A61L 31/14* (2013.01)
USPC ........................................ 525/408; 527/200

(56) References Cited

U.S. PATENT DOCUMENTS

| | | | |
|---|---|---|---|
| 2003/0087228 A1* | 5/2003 | Bamdad et al. | 435/6 |
| 2003/0087338 A1 | 5/2003 | Messersmith et al. | |
| 2004/0258753 A1 | 12/2004 | Demeester et al. | |
| 2005/0214250 A1 | 9/2005 | Harris et al. | |
| 2005/0238789 A1 | 10/2005 | Cholli et al. | |
| 2005/0241250 A1* | 11/2005 | Tarr | 52/266 |
| 2008/0145427 A1 | 6/2008 | Berchielli et al. | |
| 2008/0171012 A1 | 7/2008 | Messersmith et al. | |
| 2008/0171836 A1 | 7/2008 | Lee | |
| 2009/0035350 A1* | 2/2009 | Stankus et al. | 424/424 |

OTHER PUBLICATIONS

Declaration of Jeffrey L. Dalsin, Ph.D. under 37 C.F.R. 1.132 (Sep. 2, 2011).
Declaration of Phillip B. Messersmith, Ph.D. under 37 C.F.R. 1.132 (Sep. 2, 2011).
Nektar Advanced PEGylation Catalog 2005-2006, pp. 1-34.
Lee Bruce P. et al, Synthesis and gelation of DOPA-modified poly-(ethylene glycol) hydrogels, Biomarcromolecules, American Chemical Society, US, vol. 3, No. 5, Sep. 9, 2002, pp. 1038-1047.
Sean A Burke et al., Thermal gelation and tissue adhesion of biomimetic hydrogels; Temperature-triggered gelation of protein mimetic hydrogels, Biomedical materials, Institute of Physics Publishing, Bristol, GB, vol. 2, No. 4, Dec. 1, 2007, pp. 203-210.

* cited by examiner

Medhesive-058: PEG10k-(DH)$_6$ ; m = 37
Medhesive-059: PEG15k-(DH)$_6$ ; m = 56
Medhesive-060: PEG20k-(DH)$_6$ ; m = 75

Medhesive-074: PEG10k-(DMurea)$_6$

Medhesive-061: PEG20k-(DMu)₈ ; m = 56
Medhesive-082: PEG40k-(DMu)₈ ; m = 120

Medhesive-063: PEG20k-(DH)₈

Medhesive-068: PEG20k-(SADMe)₈

Medhesive-069: PEG20k-(GADMe)₈

Medhesive-072: PEG20k-(DMurea)₈

Medhesive-075: PEG20k-(BA)₈

Medhesive-081: PEG20k-(DOPA₄)₈

Medhesive-089: PEG20k-(DMuDHe₂)₈

Medhesive-094: PEG20k-(DOPA₃-Lys₃)₈

Medhesive-076
*PEG20k-(BAe)₈*

Medhesive-077
*PEG20k-(GA)₈*

Medhesive-078
*PEG20k-(GAe)₈*

Medhesive-079
*PEG20k-(CA)₈*

Medhesive-080
*PEG20k-(CA)₈*

Medhesive-083
*PEG15k-(DMu)₆*

Medhesive-091
PEG20K-(DH)$_8$

Medhesive-092
*dpe–PEG15k-(BA)$_6$*

Medhesive-093
*PEG20k-(THBA)$_8$*

Medhesive-103
PEG20K-(DMGADMe)₈

Medhesive-085

Medhesive-087
PEG20K-(LysDH2)$_8$

Medhesive-088
PEG20K-(AspDH2)₈

*Medhesive-090*

*Medhesive-095*

*Medhesive-099*

*Medhesive-100*

Medhesive-103
PEG20K-(DMGADMe)$_8$

Medhesive-107
PEG20K-(GABMe)$_8$

Medhesive-108
PEG40K-(LysDH2)$_8$

Medhesive-113
PEG40K-(GADMe)8

MULTI-ARMED CATECHOL COMPOUND BLENDS

CROSS REFERENCE TO RELATED APPLICATIONS

This application is a continuation of U.S. patent application Ser. No. 12/568,542 filed Sep. 28, 2009, which claims priority to U.S. Provisional application 61/100,742, filed Sep. 28, 2008, entitled "Multi-Armed Catechol Compounds" and U.S. Provisional application 61/150,471, filed Feb. 6, 2009, entitled "Multi-Armed Catechol Compound Blends", the contents of each are incorporated herein by reference for all purposes.

REFERENCE TO FEDERAL FUNDING

[1] H NMR was performed at National Magnetic Resonance Facility at Madison, which is supported by NIH (P41RR02301, P41GM66326, RR02781, RR08438), the NSF (DMB-8415048, OIA-9977486, BIR-9214394), the University of Wisconsin, and the USDA.

FIELD OF THE INVENTION

The invention relates generally to new synthetic medical adhesives which exploit the key components of natural marine mussel adhesive proteins. The method exploits a biological strategy to modify surfaces that exhibit adhesive properties useful in a diverse array of medical applications. Specifically, the invention describes the use of peptides that mimic natural adhesive proteins in their composition and adhesive properties. These adhesive moieties are coupled to a polymer chain, and provide adhesive and crosslinking (cohesive properties) to the synthetic polymer.

BACKGROUND OF THE INVENTION

Mussel adhesive proteins (MAPs) are remarkable underwater adhesive materials secreted by certain marine organisms which form tenacious bonds to the substrates upon which they reside. During the process of attachment to a substrate, MAPs are secreted as adhesive fluid precursors that undergo a crosslinking or hardening reaction which leads to the formation of a solid adhesive plaque. One of the unique features of MAPs is the presence of L-3-4-dihydroxyphenylalanine (DOPA), an unusual amino acid which is believed to be responsible for adhesion to substrates through several mechanisms that are not yet fully understood. The observation that mussels adhere to a variety of surfaces in nature (metal, metal oxide, polymer) led to a hypothesis that DOPA-containing peptides can be employed as the key components of synthetic medical adhesives.

In the medical arena, few adhesives exist which provide both robust adhesion in a wet environment and suitable mechanical properties to be used as a tissue adhesive or sealant. For example, fibrin-based tissue sealants (e.g. Tisseel VH, Baxter Healthcare) provide a good mechanical match for natural tissue, but possess poor tissue-adhesion characteristics. Conversely, cyanoacrylate adhesives (e.g. Dermabond, ETHICON, Inc.) produce strong adhesive bonds with surfaces, but tend to be stiff and brittle in regard to mechanical properties and tend to release formaldehyde as they degrade.

Therefore, a need exists for materials that overcome one or more of these current disadvantages.

BRIEF SUMMARY OF THE INVENTION

The present invention surprisingly provides a multi-armed, poly (alkylene oxide) polyether, multihydroxy (dihydroxy) phenyl derivative (DHPD) having the general formula:

$$DHPD_a-L_b-PA_c-L_d-O-\left(\left(R_1\right)_e\left(R_2\right)_f\left(R_3\right)_g O\right)_h-L_i-PA_j-L_k-DHPD_l$$
$$|$$
$$O$$
$$|$$
$$L_m$$
$$|$$
$$PA_n$$
$$|$$
$$L_o$$
$$|$$
$$DHPD_p$$

(I)

wherein
  each $DHPD_a$, $DHPD_l$, $DHPD_p$, independently, can be the same or different;
  each $L_b$, $L_k$, and $L_o$, independently, can be the same or different;
  optionally, each $L_d$, $L_i$ and $L_m$, if present, can be the same or different and if not present, represent a bond between the O and respective PA of the compound;
  each $PA_c$, $PA_j$ and $PA_n$, independently, can be the same or different;
  e is a value from 1 to about 3;
  f is a value from 1 to about 10;
  g is a value from 1 to about 3;
  h is a value from 1 to about 10;
  each of $R_1$, $R_2$ and $R_3$, independently, is a branched or unbranched alkyl group having at least 1 carbon atom;
  each PA, independently, is a substantially poly(alkylene oxide) polyether or derivative thereof;
  each L, independently, is a linker or is a suitable linking group selected from amide, ether, ester, urea, carbonate or urethane linking groups; and
  each DHPD, independently, is a multihydroxy phenyl derivative.

In one aspect, each of $DHPD_a$, $DHPD_l$, $DHPD_p$ of formula (I) is a 3,4-dihydroxyhydrocinnamic acid residue, each of $L_b$, $L_k$, and $L_o$ are amide linkages, each of $L_d$, $L_i$ and $L_m$ represent ether bonds, each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons, wherein e, f and g each a value of 1, each $R_1$ and $R_3$ is a $CH_2$ and $R_2$ is a CH; and h is 6.

In another aspect of formula (I), each of $DHPD_a$, $DHPD_j$, $DHPD_p$ is a dopamine residue; each of $L_b$, $L_k$, and $L_o$ are urethane linkages between the dopamine residue and a the terminal portion of the polyethylene glycol polyether; each of $L_d$, $L_i$ and $L_m$ represent ether bonds; each of $PA_c$, $PA_j$ and $PA_n$ are polyethylene glycol polyether derivatives comprising a hydroxyl terminal residue which form the urethane linkage between the amine residue and the polyethylene glycol polyether derivative, each having a molecular weight of between about 1,500 and about 5,000 daltons; wherein e, f and g each have a value of 1; each $R_1$ and $R_3$ is a $CH_2$ and $R_2$ is a CH; and h is 6.

In yet another aspect of formula (I), each of $DHPD_a$, $DHPD_j$, $DHPD_p$ is a dopamine residue; each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether; each of $L_d$, $L_i$ and $L_m$ represent ether bonds; each of $PA_c$, $PA_j$ and $PA_n$ are polyethylene glycol polyether derivatives comprising a hydroxyl terminal residue, each having a molecular weight of between about 1,500 and about 3,500 daltons; wherein e, f and g each a value of 1; each $R_1$ and $R_3$ is a $CH_2$ and $R_2$ is a CH; and h is 6. In particular $L_b$, $L_k$, and $L_o$ succinic acid, 3-methylglutaric acid, or glutaric acid residues.

In still yet another aspect of formula (I) each of $DHPD_a$, $DHPD_j$, $DHPD_p$ is a 3,4-dihydroxyhydrocinnamic acid residue; each of $L_b$, $L_k$, and $L_o$ are amide linkages; each of $L_d$, $L_i$ and $L_m$ represent ether bonds; each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons; wherein e, g and h each have a value of 1; each $R_1$ and $R_3$ is a $CH_2$ and $R_2$ is a CH; and f is 4. The molecular weights of $PA_c$, $PA_j$ and $PA_n$ are each about 1,500 daltons or the molecular weights of $PA_c$, $PA_j$ and $PA_n$ are each about 2,500 daltons or the molecular weights of $PA_c$, $PA_j$ and $PA_n$ are each about 3,300 daltons.

These other adhesives of the invention described throughout the specification can be utilized for wound closure and materials of this type are often referred to as tissue sealants or surgical adhesives.

The compounds of the invention can be applied to a suitable substrate surface as a film or coating. Application of the compound(s) to the surface inhibits or reduces the growth of biofilm (bacteria) on the surface relative to an untreated substrate surface. In other embodiments, the compounds of the invention can be employed as an adhesive.

In one embodiment, adhesive compounds of the present invention provide a method of adhering a first surface to a second surface in a subject. In some embodiments, the first and second surfaces are tissue surfaces, for example, a natural tissue, a transplant tissue, or an engineered tissue. In further embodiments, at least one of the first and second surfaces is an artificial surface. In some embodiments, the artificial surface is an artificial tissue. In other embodiments, the artificial surface is a device or an instrument. In some embodiments, adhesive compounds of the present invention seal a defect between a first and second surface in a subject. In other embodiments, adhesive compounds of the present invention provide a barrier to, for example, microbial contamination, infection, chemical or drug exposure, inflammation, or metastasis. In further embodiments, adhesive compounds of the present invention stabilize the physical orientation of a first surface with respect to a second surface. In still further embodiments, adhesive compounds of the present invention reinforce the integrity of a first and second surface achieved by, for example, sutures, staples, mechanical fixators, or mesh. In some embodiments, adhesive compounds of the present invention provide control of bleeding. In other embodiments, adhesive compounds of the present invention provide delivery of drugs including, for example, drugs to control bleeding, treat infection or malignancy, or promote tissue regeneration.

Exemplary applications include, but are not limited to fixation of synthetic (resorbable and non-resorbable) and biological membranes and meshes for hernia repair, void-eliminating adhesive for reduction of post-surgical seroma formation in general and cosmetic surgeries, fixation of synthetic (resorbable and non-resorbable) and biological membranes and meshes for tendon and ligament repair, sealing incisions after ophthalmic surgery, sealing of venous catheter access sites, bacterial barrier for percutaneous devices, as a contraceptive device, a bacterial barrier and/or drug depot for oral surgeries (e.g. tooth extraction, tonsillectomy, cleft palate, etc.), for articular cartilage repair, for antifouling or anti-bacterial adhesion.

In one embodiment, the reaction products of the syntheses described herein are included as compounds or compositions useful as adhesives or surface treatment/antifouling aids. It should be understood that the reaction product(s) of the synthetic reactions can be purified by methods known in the art, such as diafiltration, chromatography, recrystallization/precipitation and the like or can be used without further purification.

It should be understood that the compounds of the invention can be coated multiple times to form bi, tri, etc. layers. The layers can be of the compounds of the invention per se, or of blends of a compound(s) and polymer, or combinations of a compound layer and a blend layer, etc.

Consequently, constructs can also include such layering of the compounds per se, blends thereof, and/or combinations of layers of a compound(s) per se and a blend or blends.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
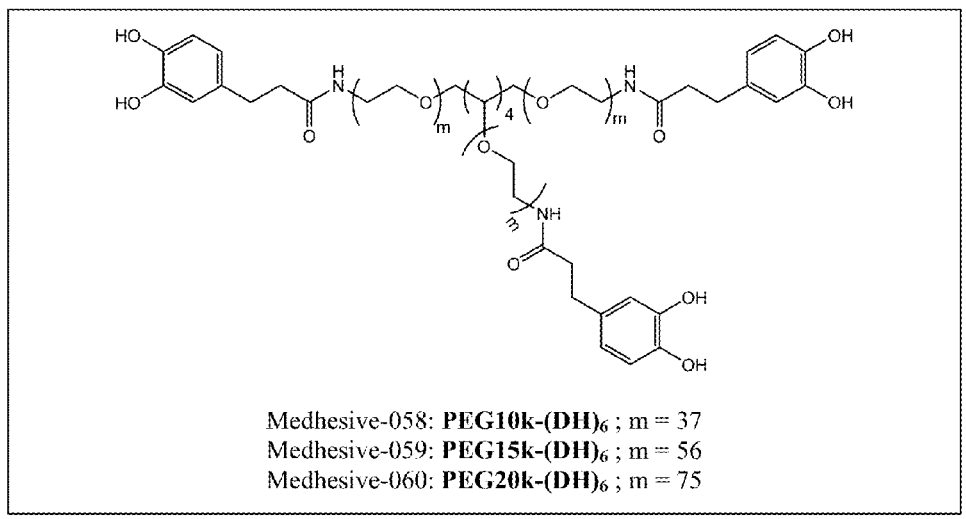
FIG. 1 depicts compounds encompassed by the invention.
Figure 1:
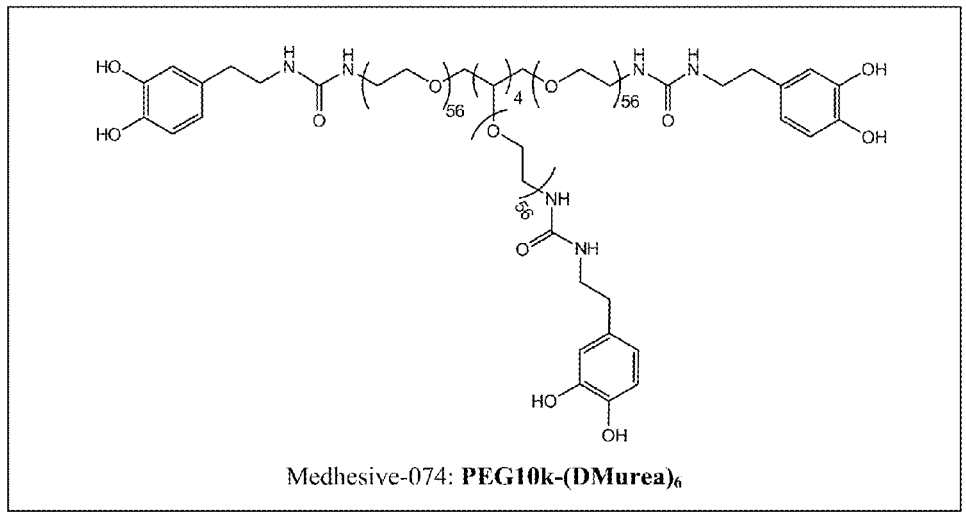
Figure 1:
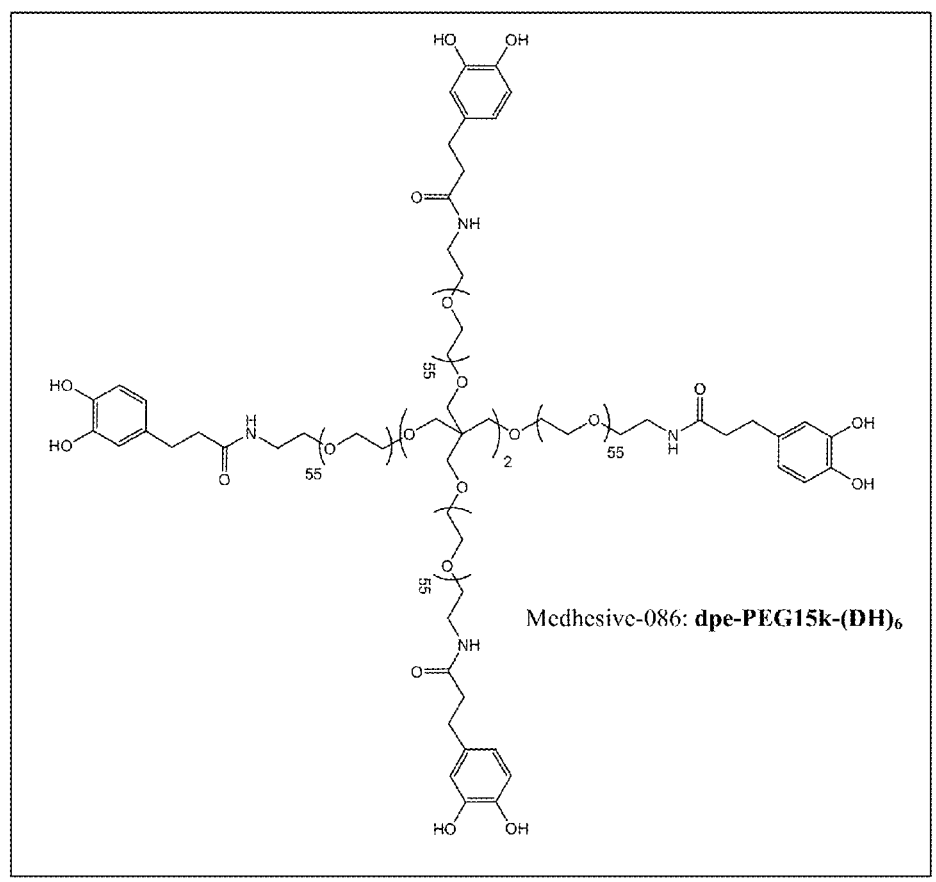
Figure 1:
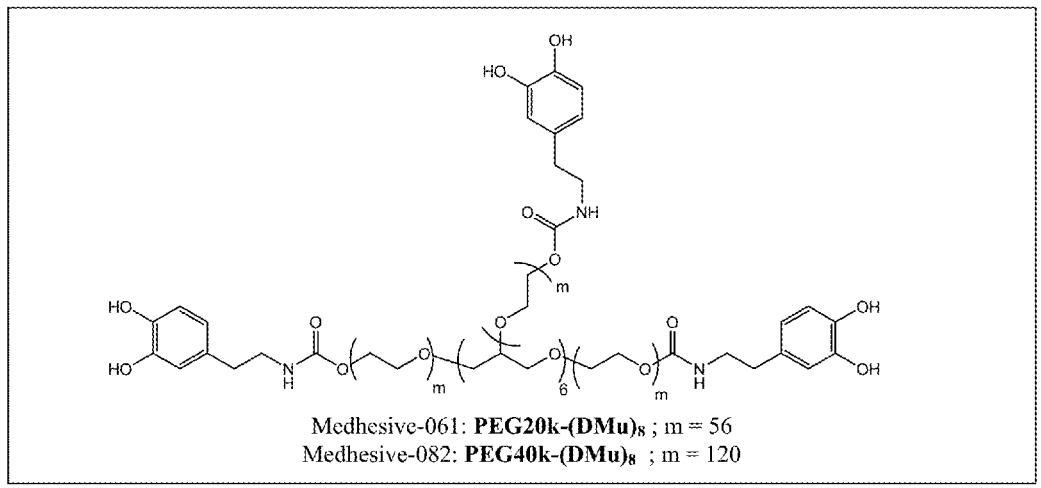
Figure 1:
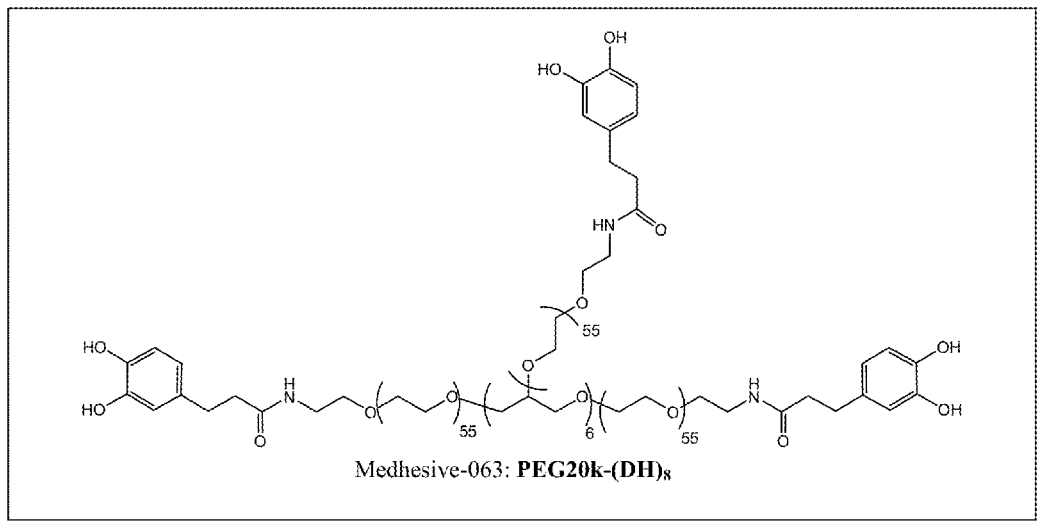
Figure 1:
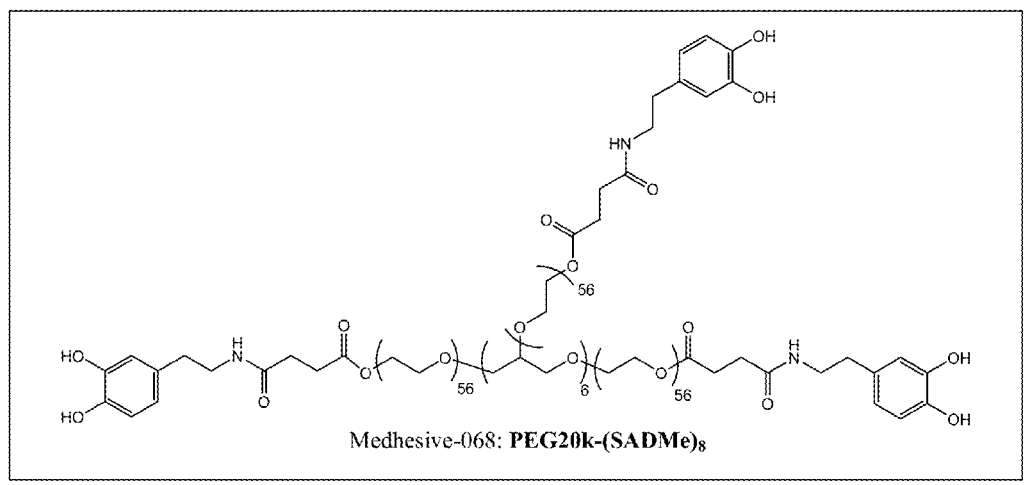
Figure 1:
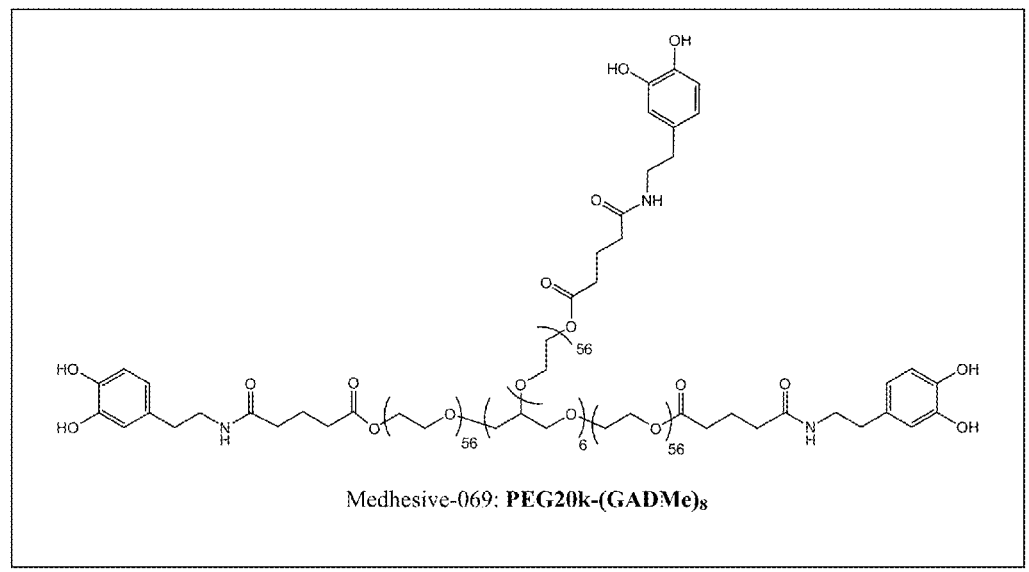
Figure 1:
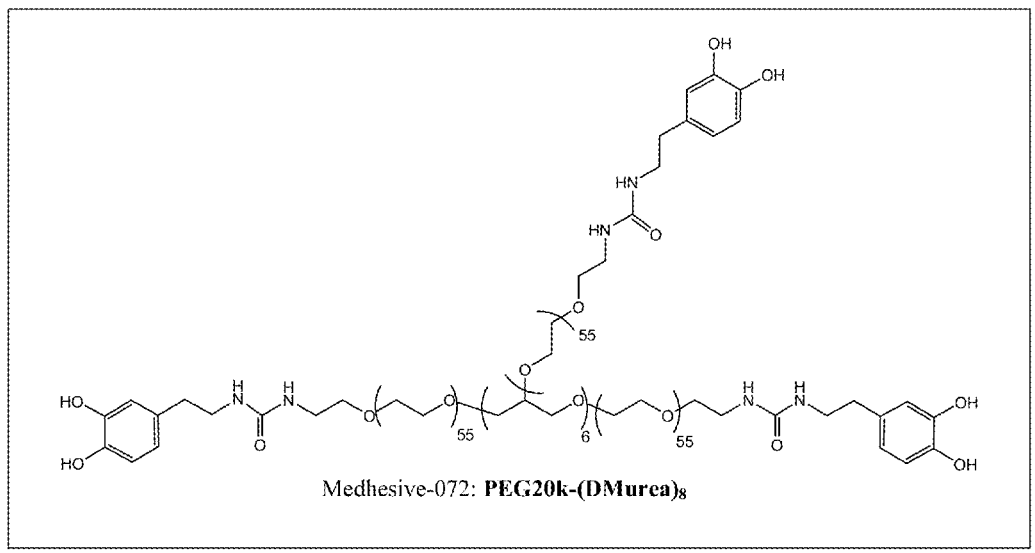
Figure 1:
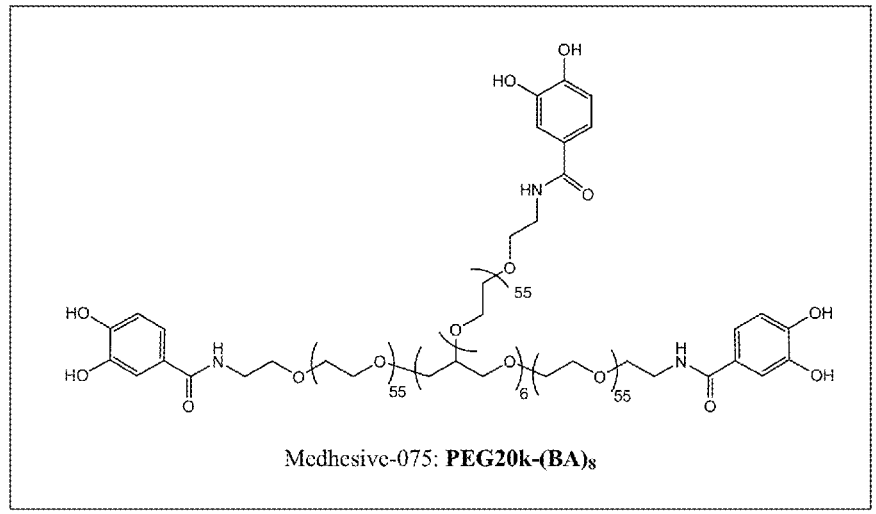
Figure 1:
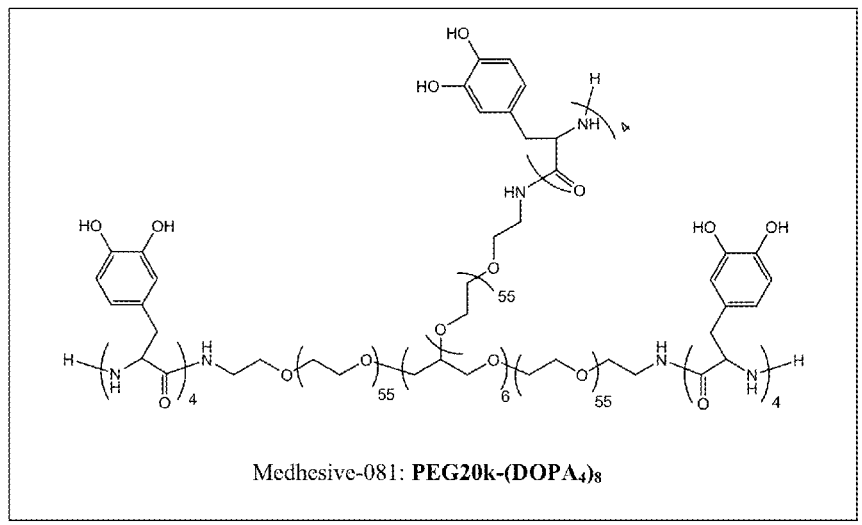
Figure 1:
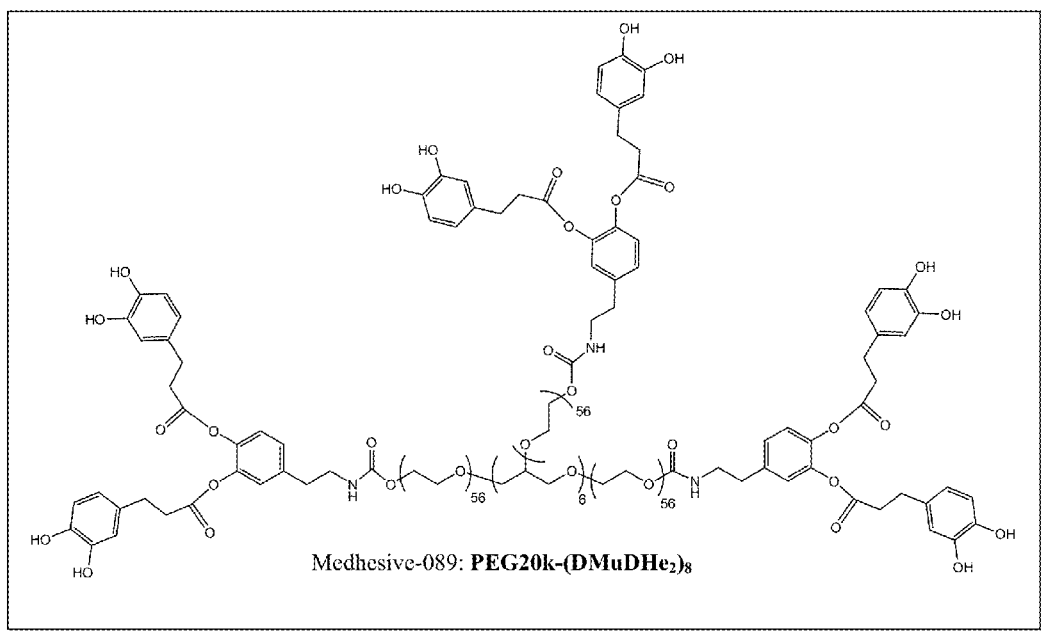
Figure 1:
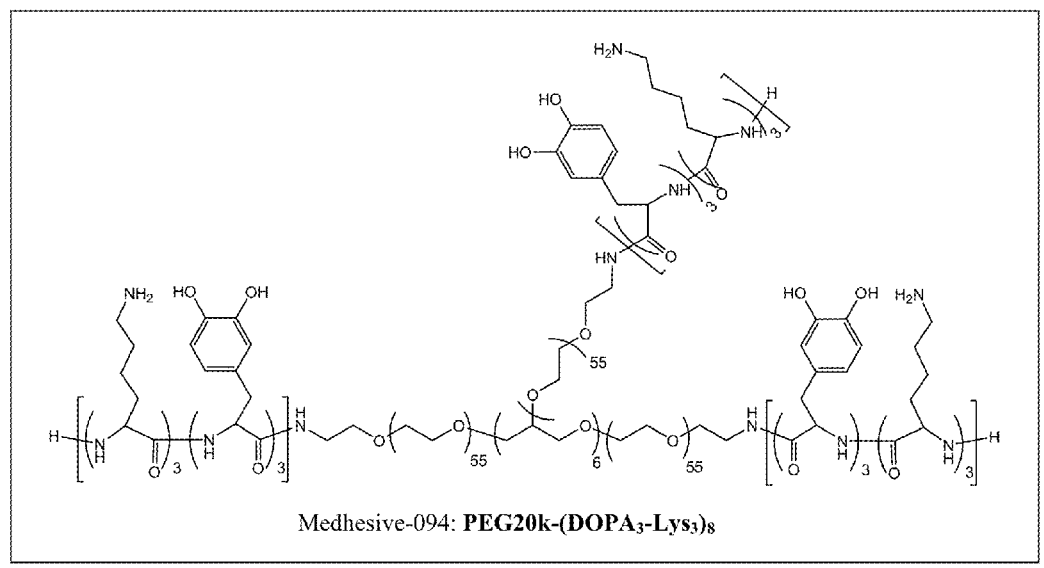
Figure 1:
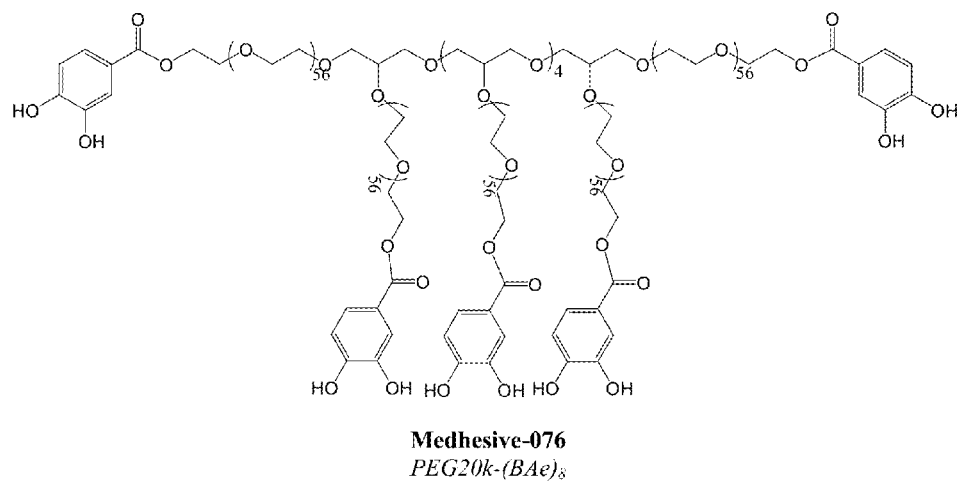
Figure 1:
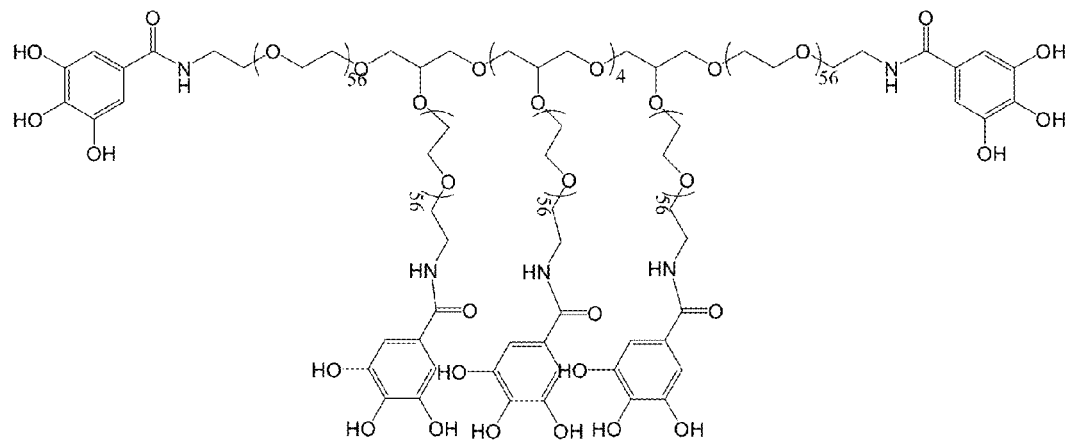
Figure 1:
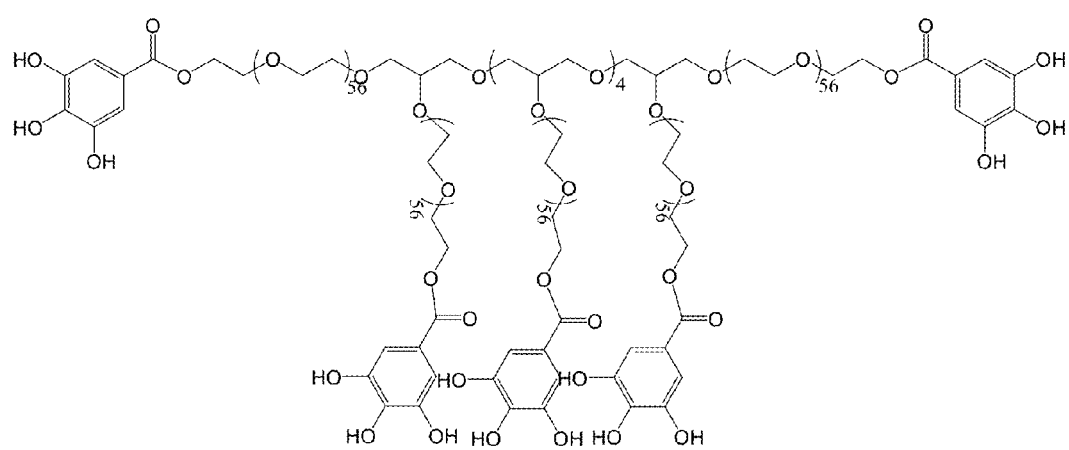
Figure 1:
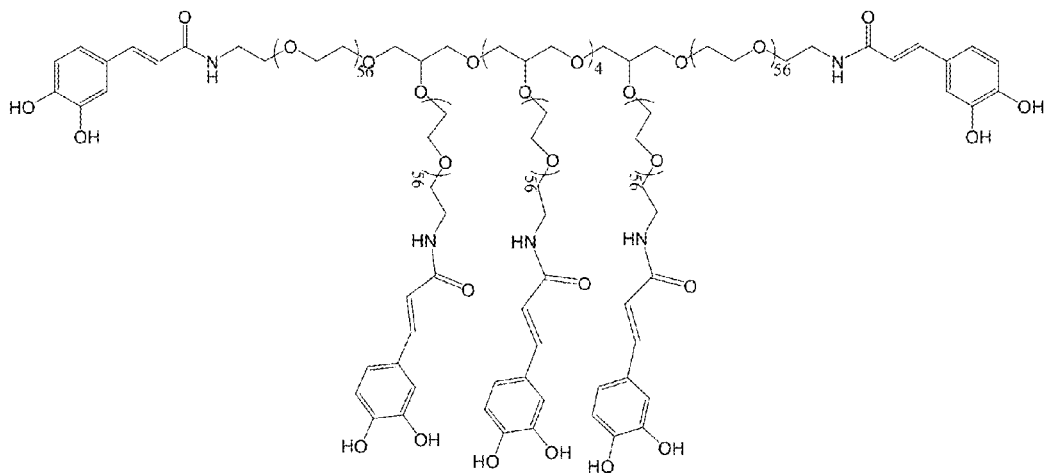
Figure 1:
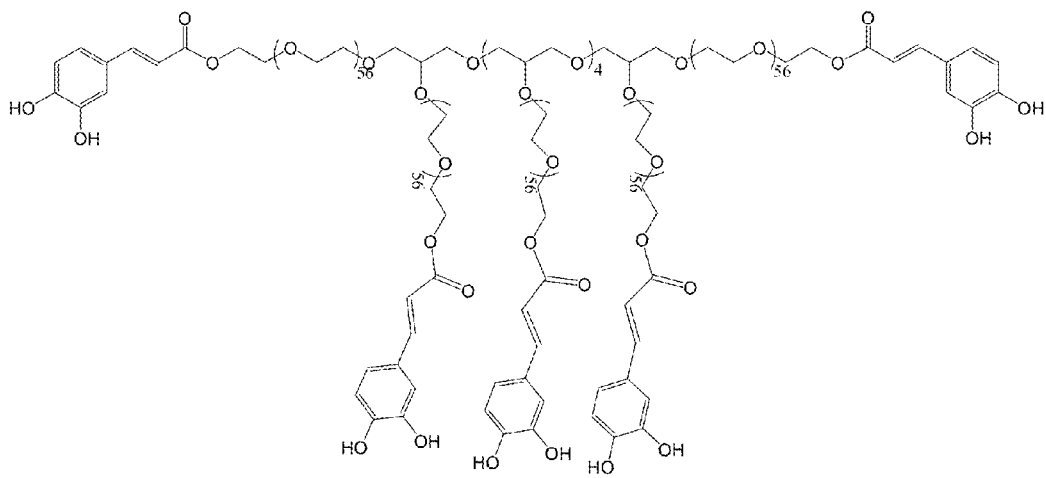
Figure 1:
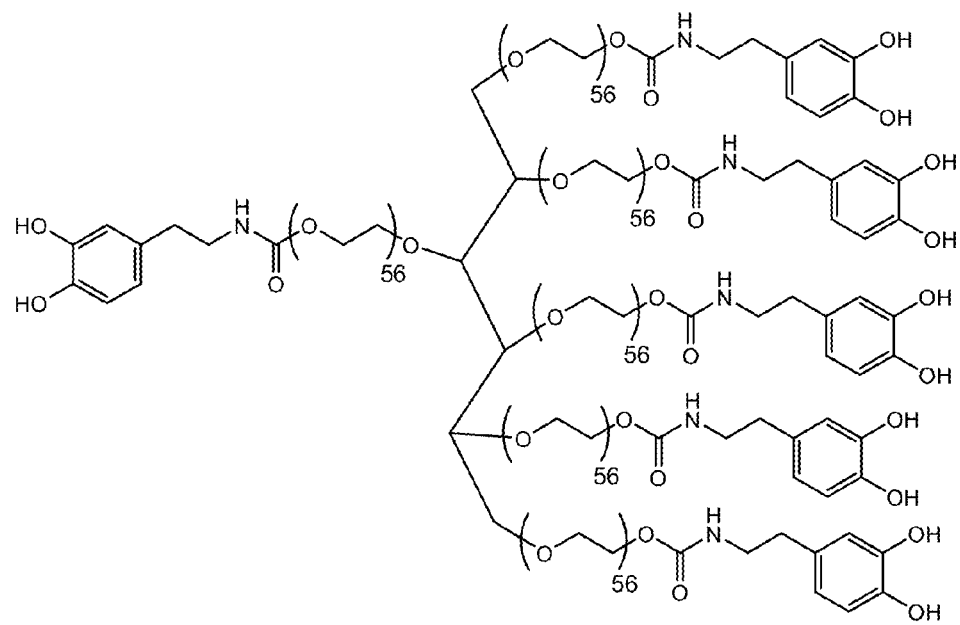
Figure 1:
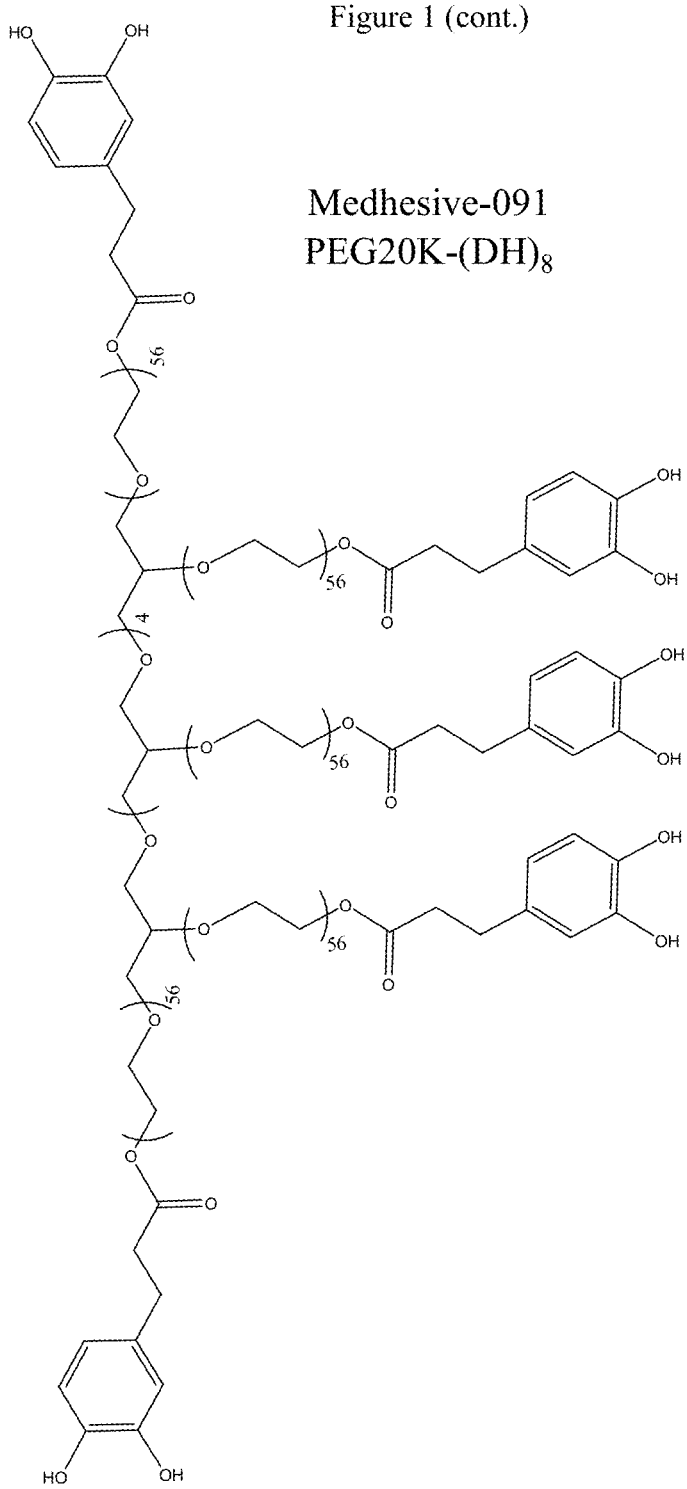
Figure 1:
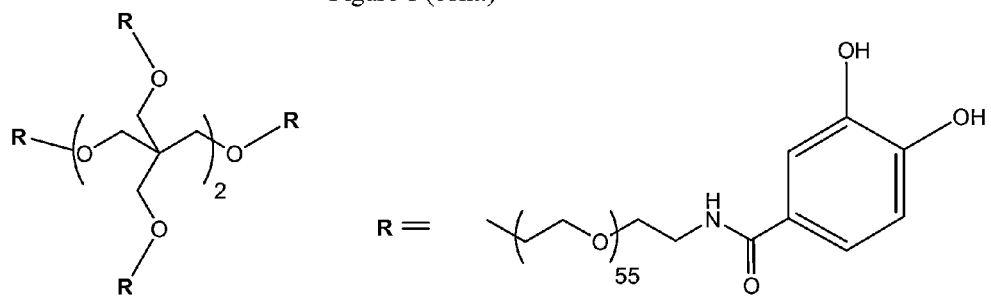
Figure 1:
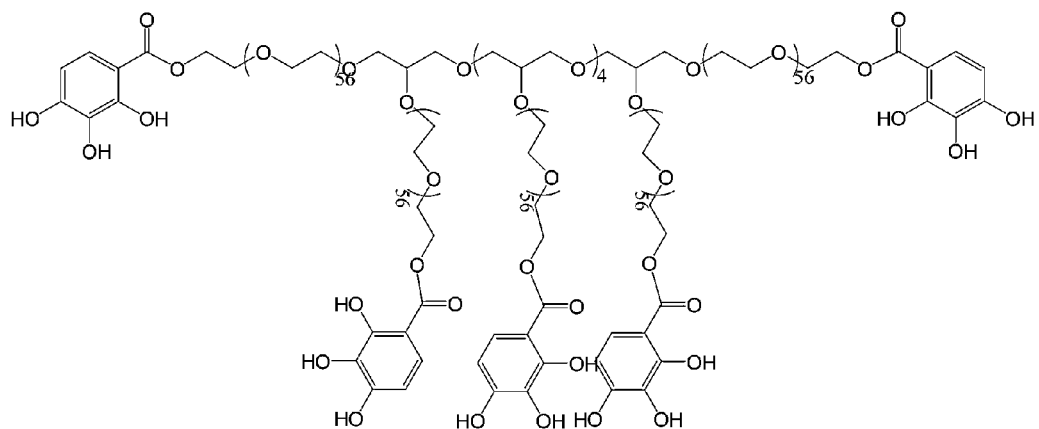
Figure 1:
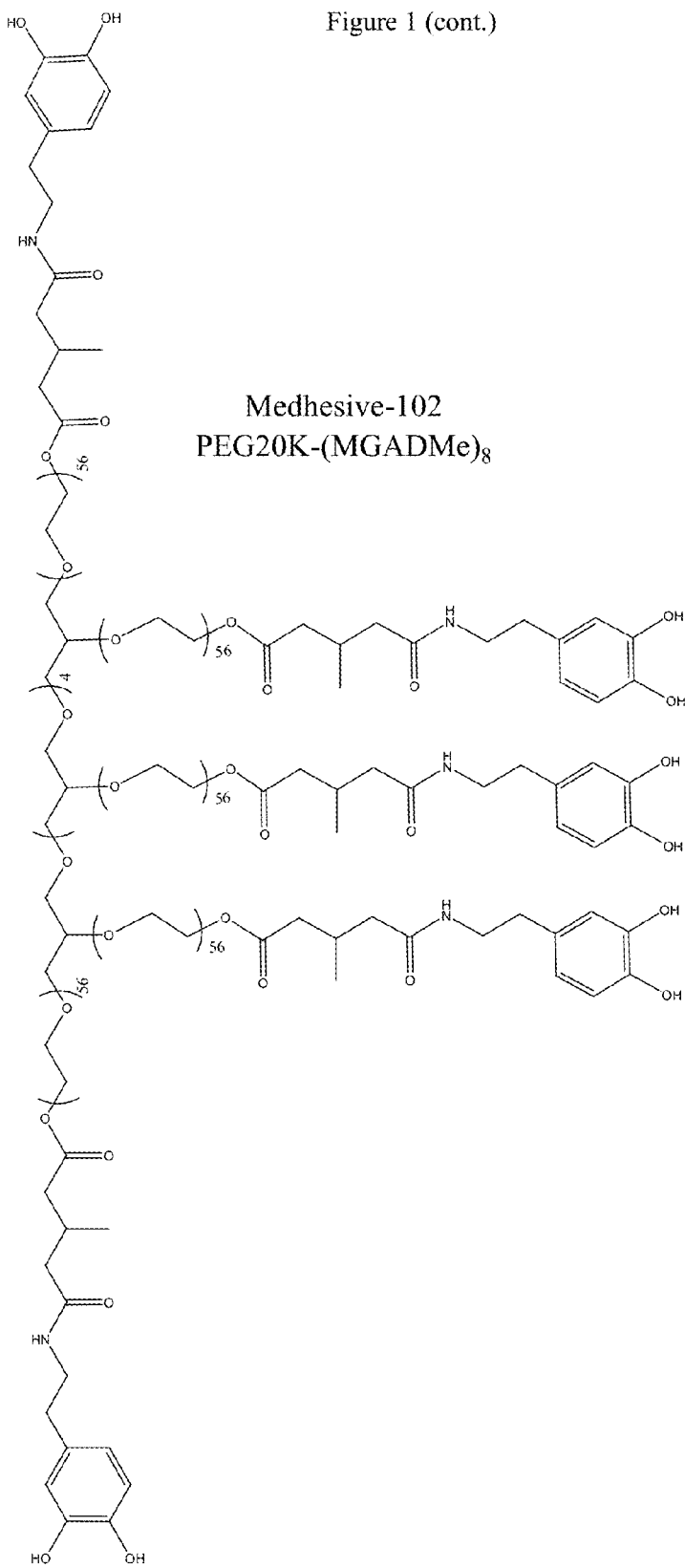
Figure 1:
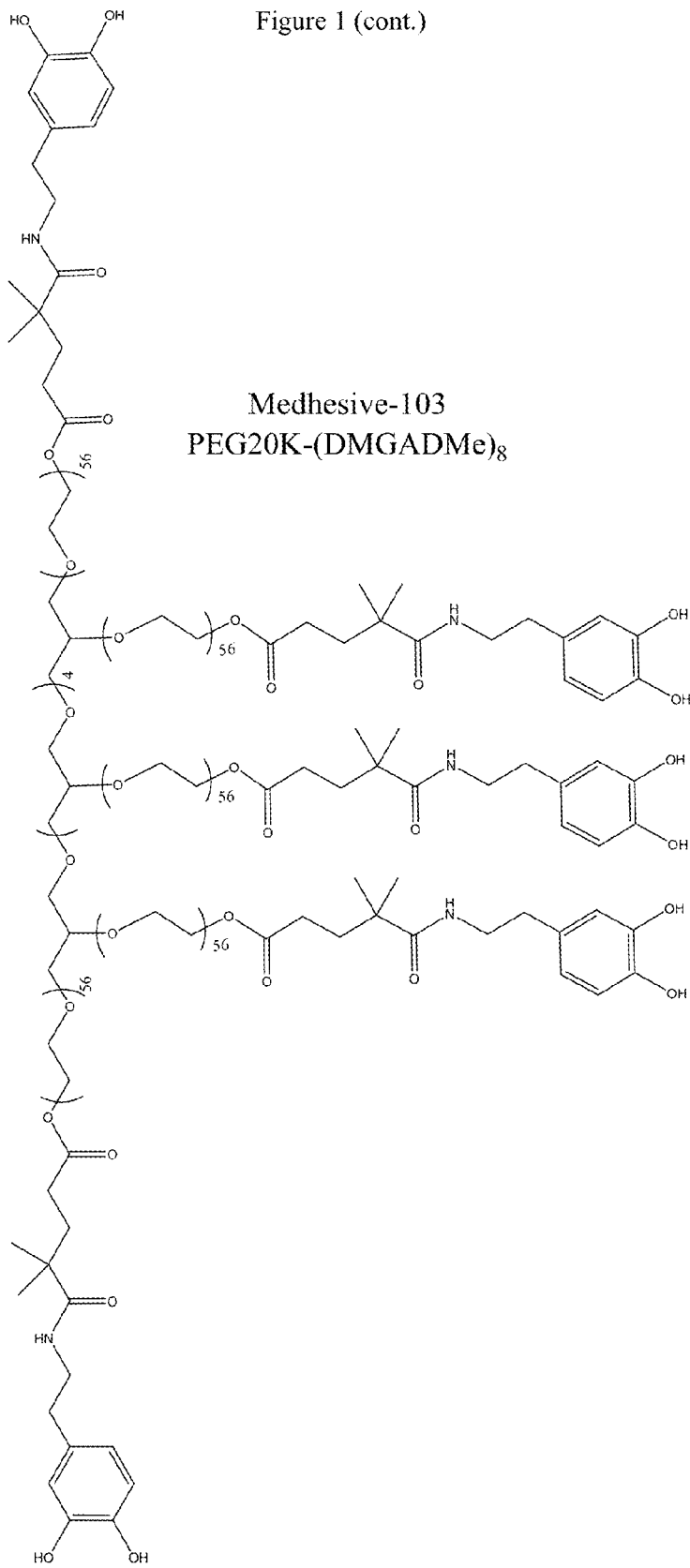
Figure 1:
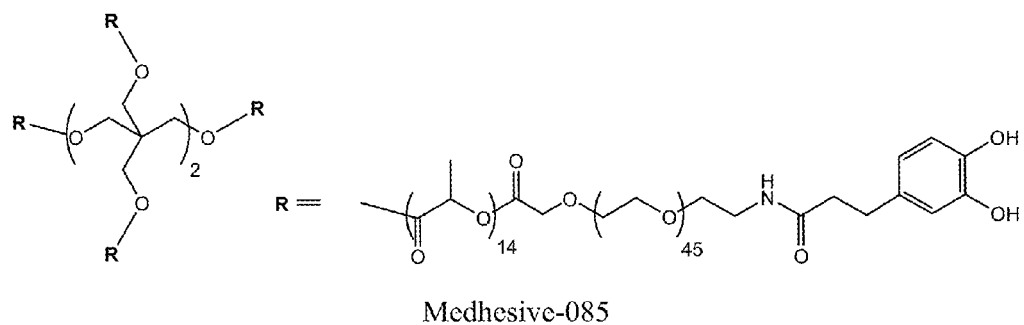
Figure 1:
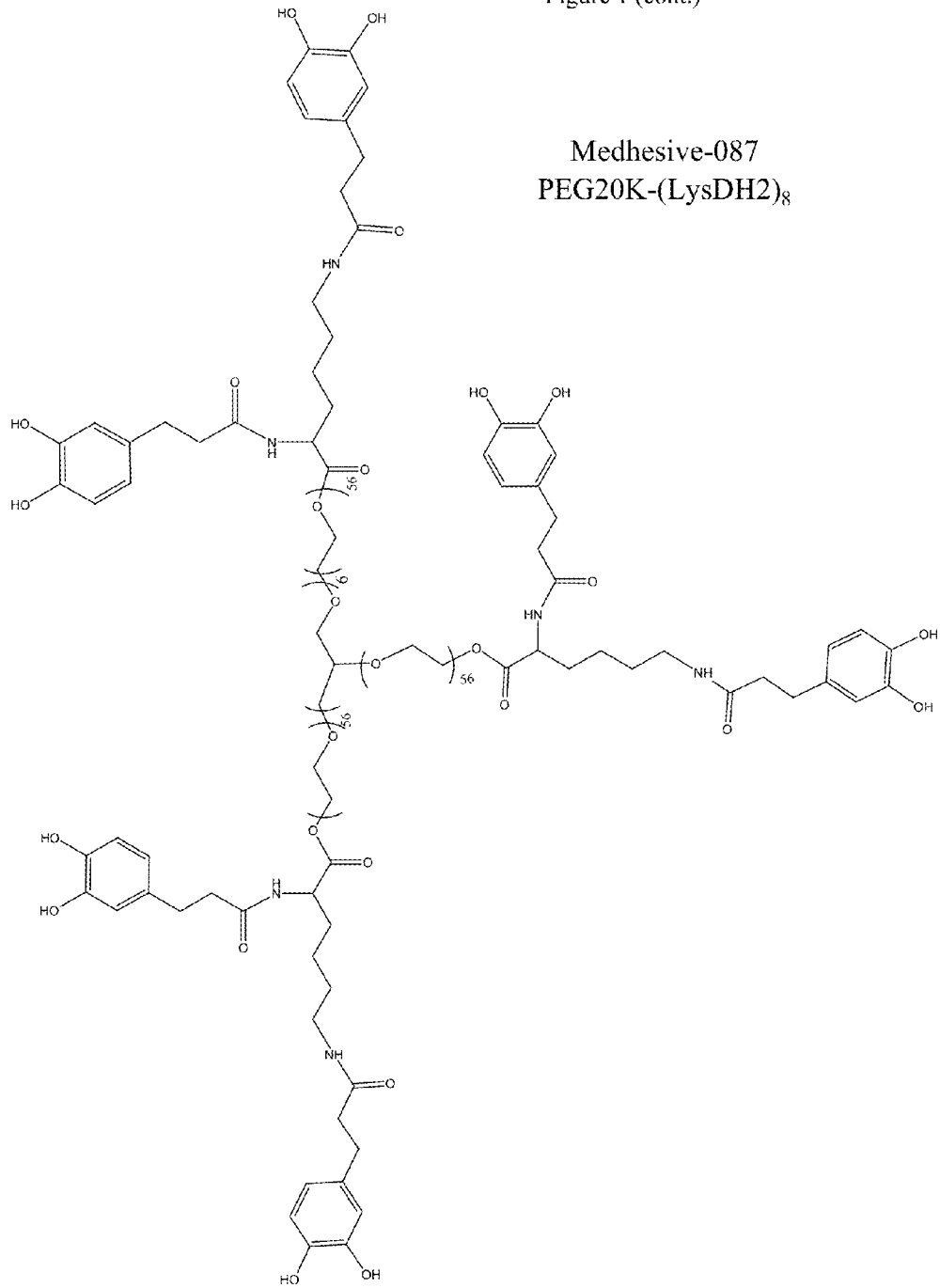
Figure 1:
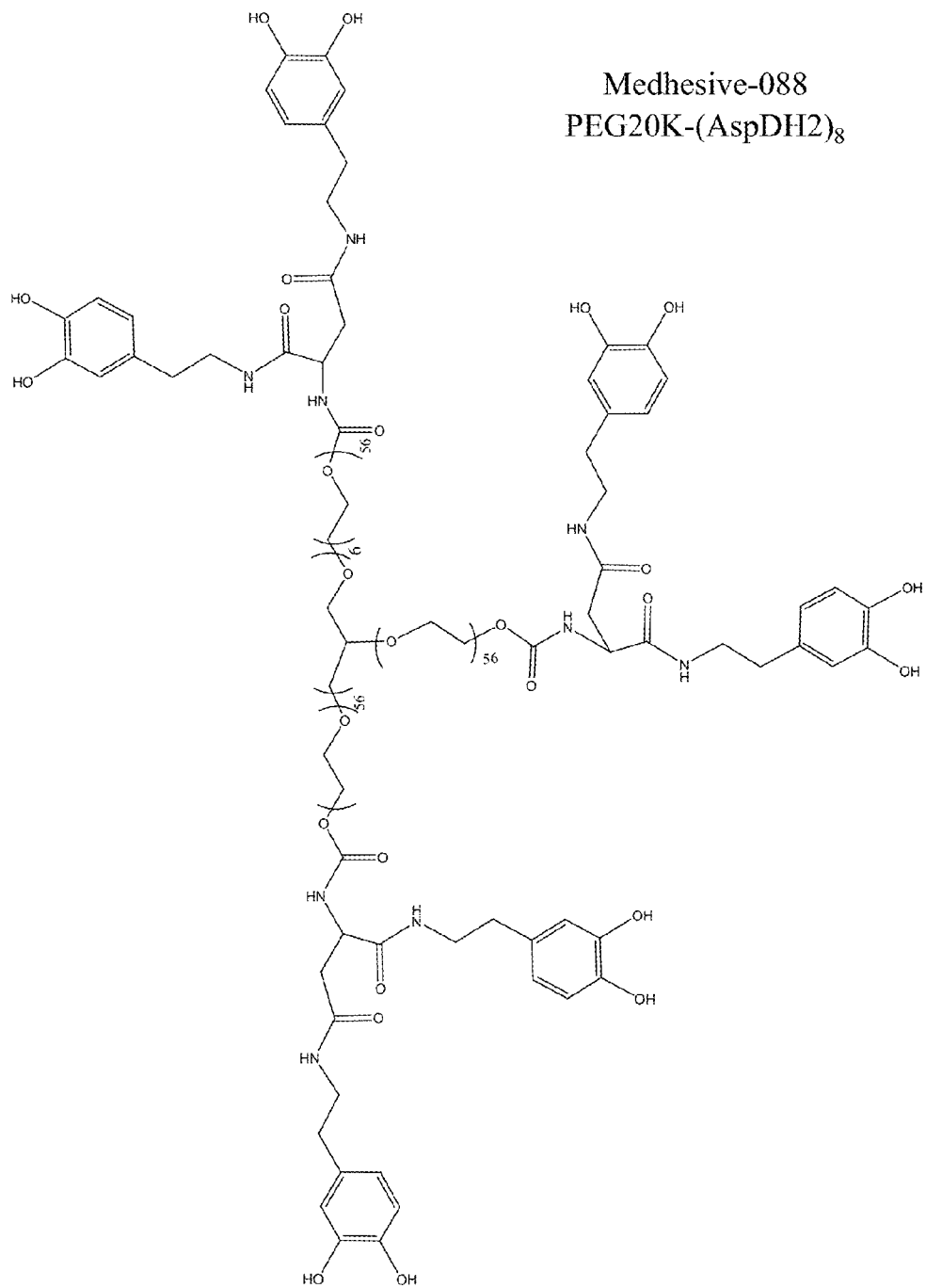
Figure 1:
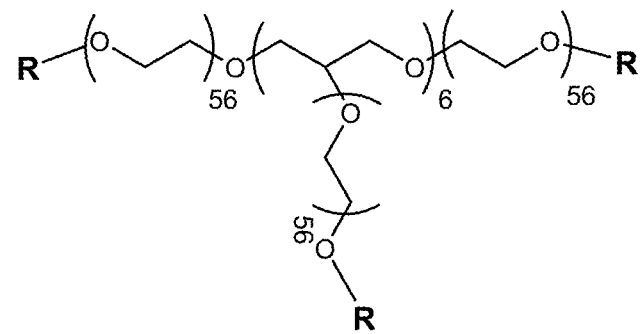
Figure 1:
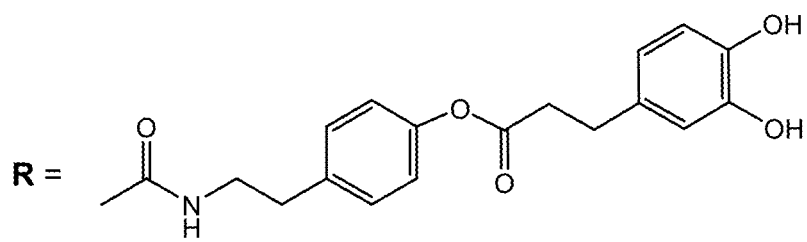
Figure 1:
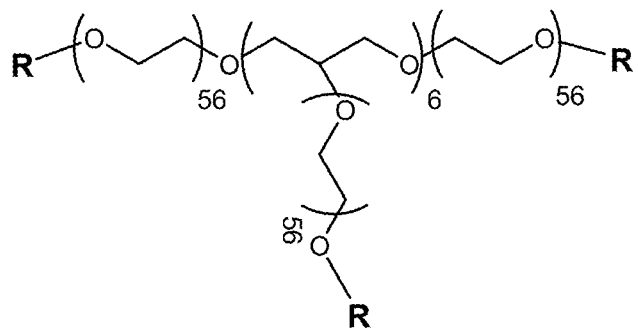
Figure 1:
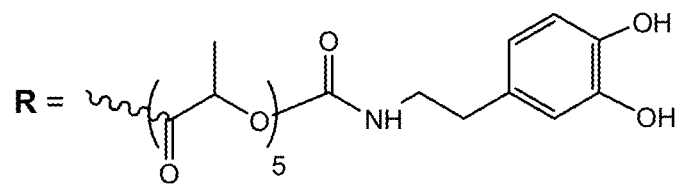
Figure 1:
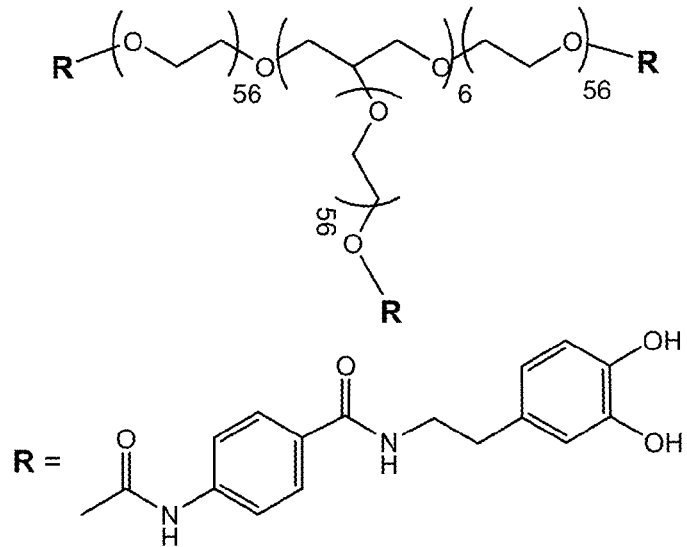
Figure 1:
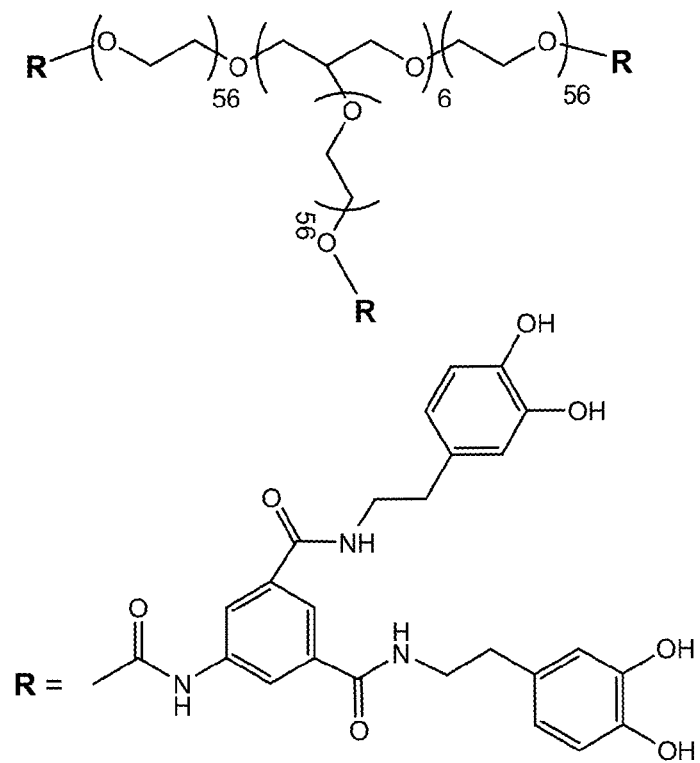
Figure 1:
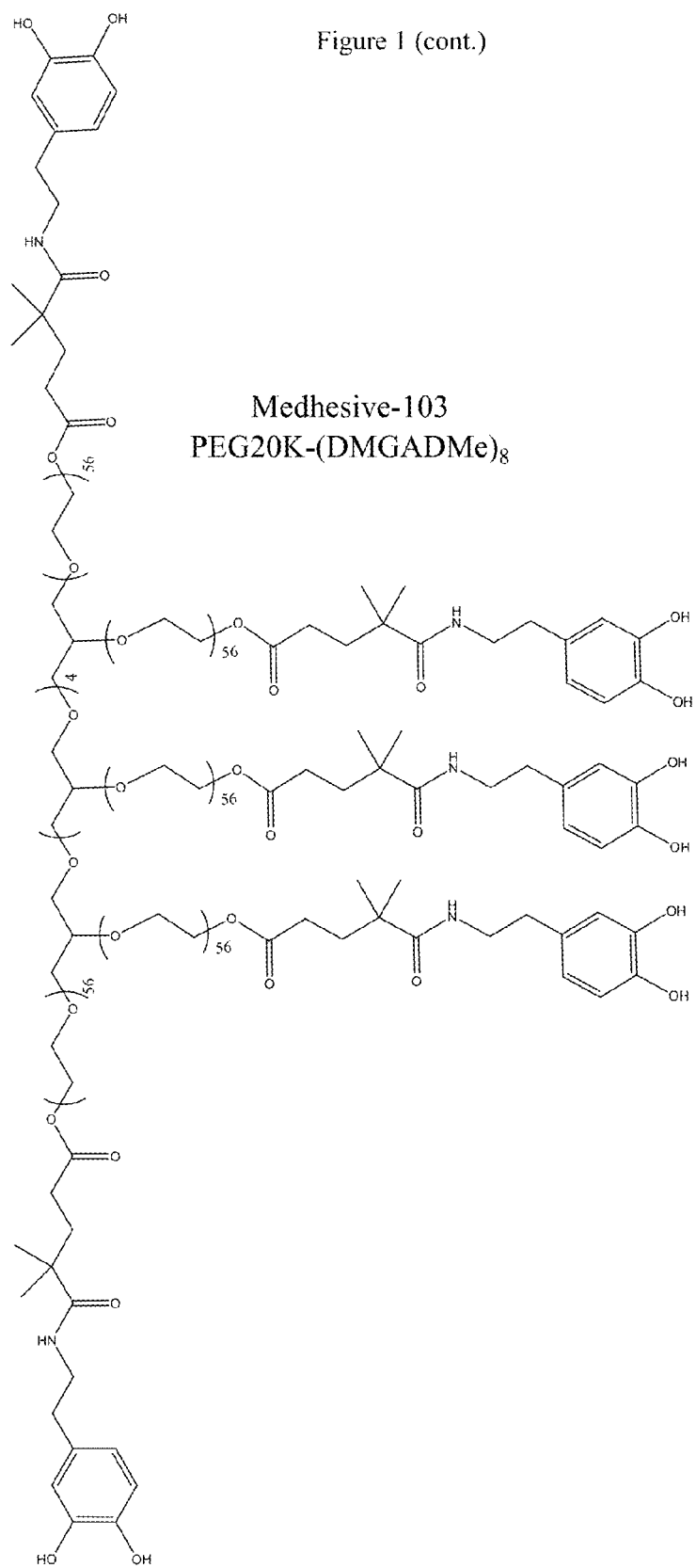
Figure 1:
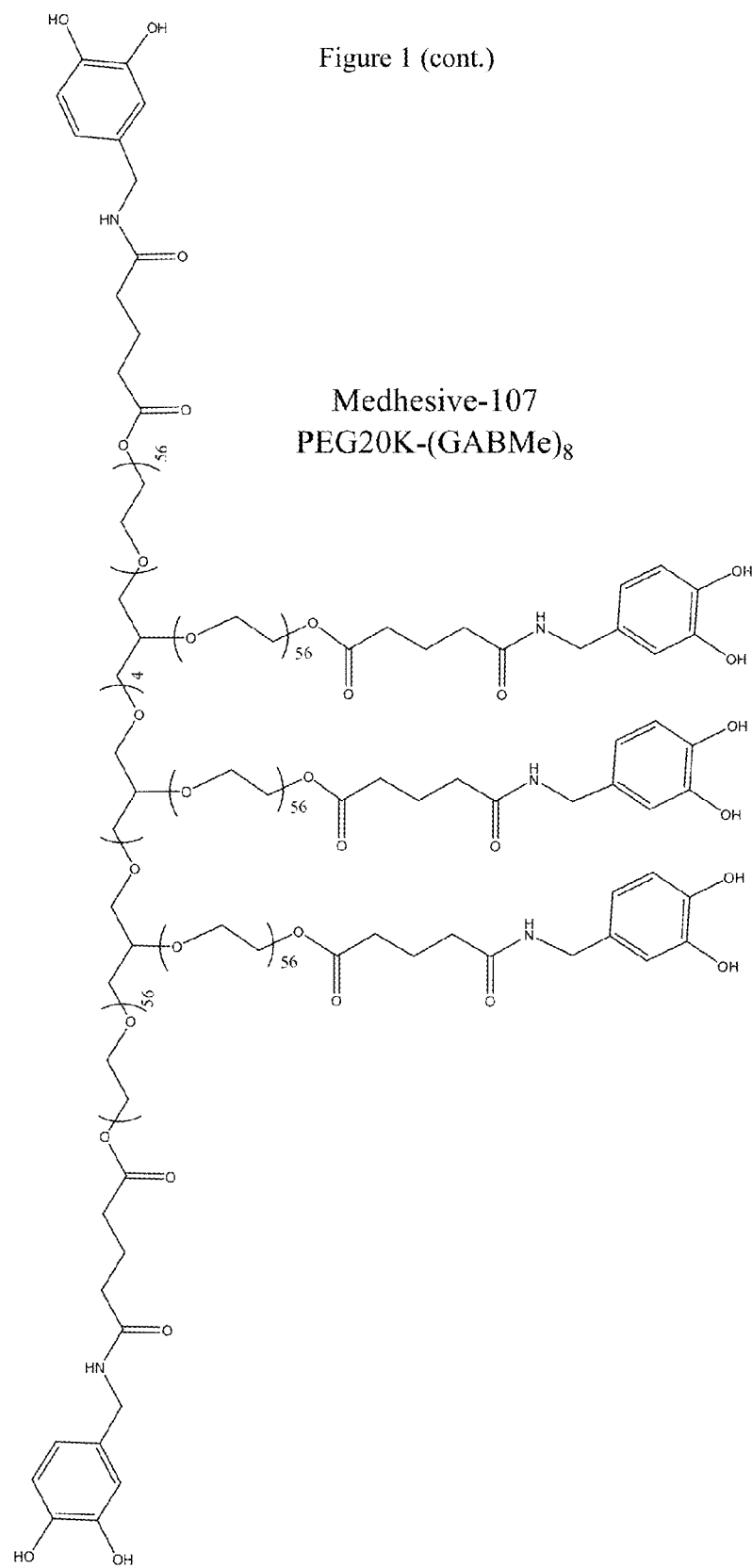
Figure 1:
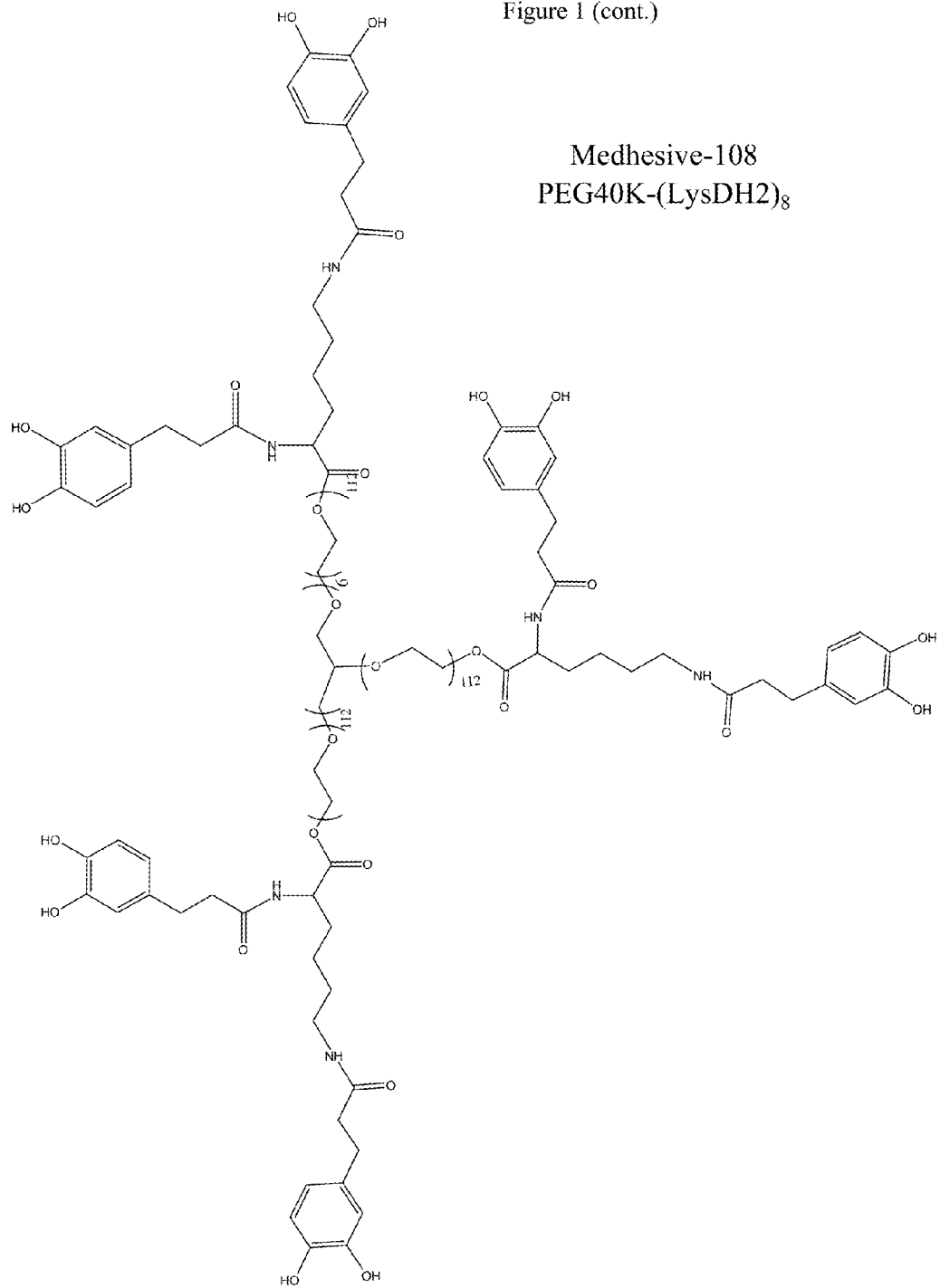
Figure 1:
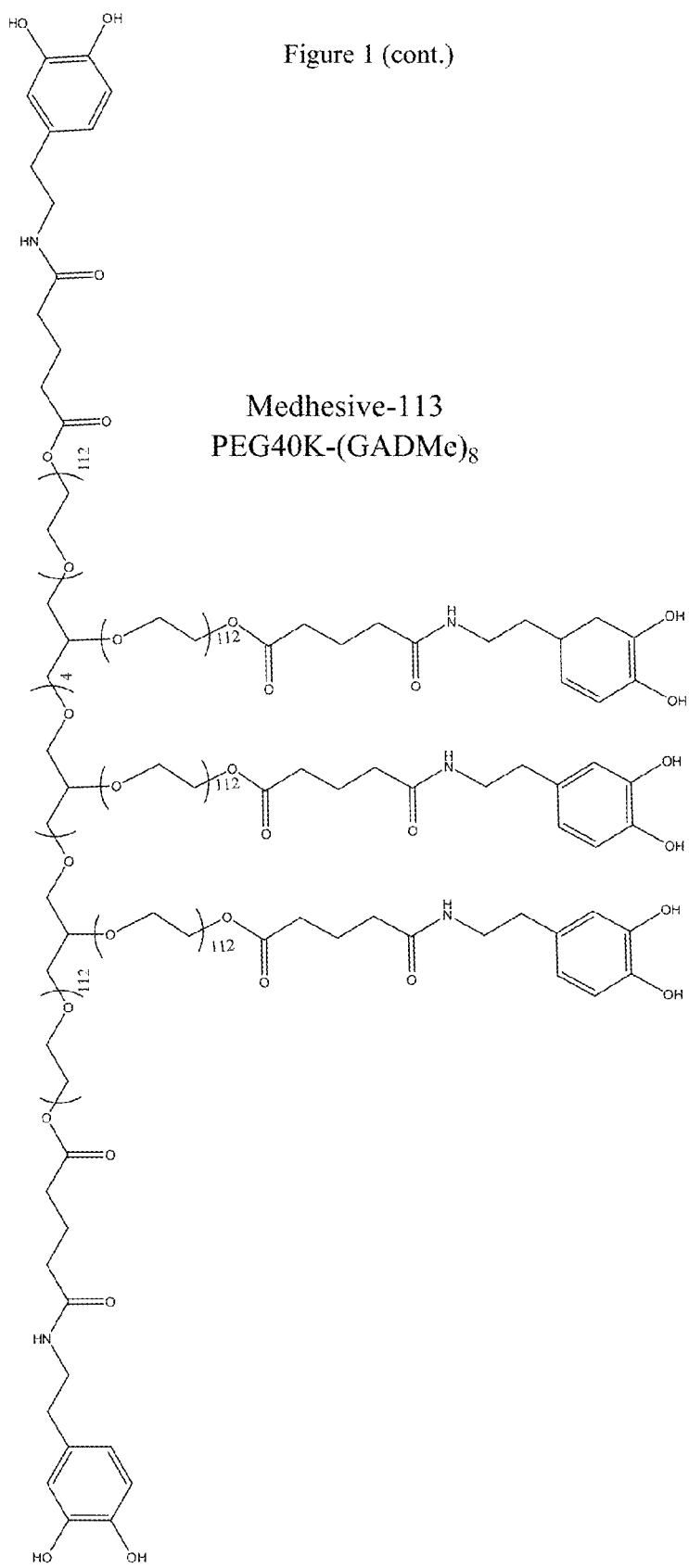

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms ($C_1$-$C_6$ alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$—$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms e.g., N, O, S, P, etc. and of functional groups e.g., —COOH, —$NH_2$, —SH, or —OH as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, of this polymer. It should also be understood that PAs can include terminal end groups such as PA-O—$CH_2$—$CH_2$—$NH_2$, e.g., PEG-O—$CH_2$—$CH_2$—$NH_2$ (as a common form of amine terminated PA). PA-O—$CH_2$—$CH_2$—$CH_2$—$NH_2$, e.g., PEG-O—$CH_2$—$CH_2$—$CH_2$—$NH_2$ is also available as well as PA-O—($CH_2$—CH($CH_3$)—O)$_{xx}$—$CH_2$—CH($CH_3$)—$NH_2$, where xx is 0 to about 3, e.g., PEG-O—($CH_2$—CH($CH_3$)—O)$_{xx}$—$CH_2$—CH($CH_3$)—$NH_2$ and a PA with an acid end-group typically has a structure of PA-O—$CH_2$—COOH, e.g., PEG-O—$CH_2$—COOH or PA-O—$CH_2$—$CH_2$—COOH, e.g., PEG-O—$CH_2$—$CH_2$—COOH. These can be considered "derivatives" of the PA. These are all contemplated as being within the scope of the invention and should not be considered limiting.

Generally each PA of the molecule has a molecular weight between about 1,250 and about 5,000 daltons and most particularly between about 1,500 and about 3,500 daltons. Therefore, it should be understood that the desired MW of the whole or combined polymer is between about 5,000 and about 50,000 Da, in particular a MW of between about 10,000 and about 20,000 Da, where the molecule has six to eight "arms", each arm having a MW of between about 1,250 and about 5,000 daltons, and in particular a MW of 1,500 and about 3,500 Da, e.g., about 3300 daltons, or about 2,500 daltons.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation or Creative PEGWorks. In one embodiment, the PA is a polyalkylene glycol polyether or derivative thereof, and most particularly is polyethylene glycol (PEG), the PEG unit (arm) having a molecular weight generally in the range of between about 1,250 and about 12,500 daltons, in particular between about 2,500 and about 10,000 daltons, e.g., 5,000 daltons.

It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

It should be understood that the PA terminal end groups can be functionalized. Typically the end groups are OH, NH$_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notations of "L", "FnL" and "L" refer, respectively, to a linker, functional linker and a linking group.

A "linker" (L) refers to a moiety that has two points of attachment on either end of the moiety. For example, an alkyl dicarboxylic acid HOOC-alkyl-COOH (e.g., succinic acid) would "link" a terminal end group of a PA (such as a hydroxyl or an amine to form an ester or an amide respectively) with a reactive group of the DHPD (such as an NH$_2$, OH, or COOH). Suitable linkers include an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano[2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C2 through C10 dicarbonyl alkylenes such as malonic acid, succinic acid, 3-methylglutaric acid, glutaric acid, etc. Additionally, the anhydrides, acid halides and esters of such materials can be used to effect the linking when appropriate.

Other suitable linkers include moieties that have two different functional groups that can react and link with an end group of a PA. These include groups such as amino acids (glycine, lysine, aspartic acid, etc.) and moieties such as dopamine.

A functional linker (FnL) is a linker, such as those noted above, that includes one or more moieties that can react with a reactive site of the DHPD molecule. Generally such moieties are amines, esters, carboxylic acids, etc. For example, aspartic is a dicarboxylic acid with an amine group. The dicarboxylic acid portion of the molecule can be reacted to form part of the polymer backbone while the amine portion can be reacted with the DHPD, forming, or example, an amide bond, e.g., where the amide bond is a "L". The functional linker can contain several moieties that can react with reactive sites of DHPD molecules. For example, lysine, is a dicarboxylic acid with an amine residue. Consequently, condensation of lysine with DHPD molecules and a PEG provide a molecule that contains two amide bonds, where the DHPD's contain reactive esters, and an ester where the terminal carboxylic acid/ester forms the ester bond with the hydroxyl of a PEG. This can be signified by DHPD-L-FnL-(L-DHPD)-L, where the FnL contains three points of attachment to the polymer backbone (amide, amide, ester).

It should be understood that two or more linkers may be adjacent to each other. In such embodiments, two reactive portions of the two or more linkers combine to form a bond, such as an ester bond, an amide bond, etc. (L). For example, a carboxylic acid can react with a group that includes a hyroxyl group, such that an ester is formed. Many combinations can be envisaged between various linkers and are contemplated within the scope of this application. Additionally, the one or more of the linkers can be functional linkers.

A linking group (L) refers to the reaction product of the terminal end moieties of the PA and DHPD (the situation where "b" is 0; no linker present) condense to form an amide, ether, ester, urea, carbonate or urethane linkage depending on the reactive sites on the PA and DHPD. In other words, a direct bond is formed between the PA and DHPD portion of the molecule and no linker is present.

The term "residue" is used to mean that a portion of a first molecule reacts (e.g., condenses) with a portion of a second molecule to form, for example, a linking group, such an amide, ether, ester, urea, carbonate or urethane linkage depending on the reactive sites on the PA and DHPD.

The denotation "DHDP" refers to a multihydroxy phenyl derivative, such as a dihydroxy phenyl derivative, for example, a 3,4 dihydroxy phenyl moiety. Suitable DHDP derivatives include the formula:

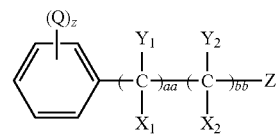

wherein Q is an OH;
"z" is 2 to 5;
each $X_1$, independently, is H, NH$_2$, OH, or COOH;
each $Y_1$, independently, is H, NH$_2$, OH, or COOH;
each $X_2$, independently, is H, NH$_2$, OH, or COOH;
each $Y_2$, independently, is H, NH$_2$, OH, or COOH;
Z is COOH, NH$_2$, OH or SH;
aa is a value of 0 to about 4;
bb is a value of 0 to about 4; and
optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1 when a double bond is present.

In one aspect, z is 3.

In particular, "z" is 2 and the hydroxyls are located at the 3 and 4 positions of the phenyl ring.

In one embodiment, each $X_1$, $X_2$, $Y_1$ and $Y_2$ are hydrogen atoms, aa is 1, bb is 1 and Z is either COOH or NH$_2$.

In another embodiment, $X_1$ and $Y_2$ are both hydrogen atoms, $X_2$ is a hydrogen atom, aa is 1, bb is 1, $Y_2$ is NH$_2$ and Z is COOH.

In still another embodiment, $X_1$ and $Y_2$ are both hydrogen atoms, aa is 1, bb is 0, and Z is COOH or NH$_2$.

In still another embodiment, aa is 0, bb is 0 and Z is COOH or NH$_2$.

In still yet another embodiment, z is 3, aa is 0, bb is 0 and Z is COOH or NH$_2$.

It should be understood that where aa is 0 or bb is 0, then $X_i$ and $Y_1$ or $X_2$ and $Y_2$, respectively, are not present.

It should be understood, that upon condensation of the DHDP molecule with the PA that a molecule of water, for example, is generated such that a bond is formed as described above (amide, ether, ester, urea, carbonate or urethane).

In particular, DHPD molecules include dopamine, 3,4-dihydroxy phenylalanine (DOPA), 3,4-dihydroxyhydrocinnamic acid, 3,4-dihydroxyphenyl ethanol, 3,4 dihydroxyphenylacetic acid, 3,4 dihydroxyphenylamine, 3,4-dihydroxybenzoic acid, gallic acid, 2, 3,4, trihydroxybenzoic acid and 3,4 dihydroxycinnamic acid, etc.

The present invention surprisingly provides a multi-armed, poly (alkylene oxide) polyether, multihydroxy (dihydroxy) phenyl derivative (DHPD) having the general formula:

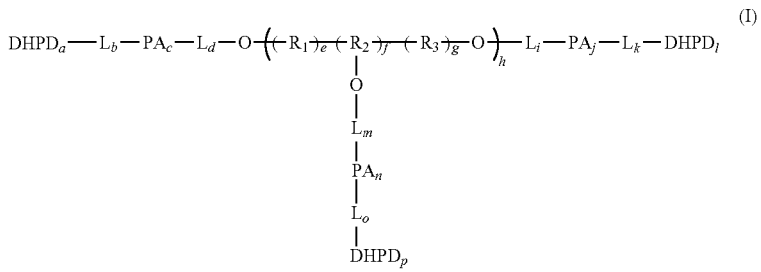

(I)

wherein each $DHPD_a$, $DHPD_l$, $DHPD_p$, independently, can be the same or different;

each $L_b$, $L_k$, and $L_o$, independently, can be the same or different;

optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

e is a value from 1 to about 3;
f is a value from 1 to about 10;
g is a value from 1 to about 3;
h is a value from 1 to about 10;

each of $R_1$, $R_2$ and $R_3$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups; and each DHPD, independently, is a multihydroxy phenyl derivative.

It should be understood that where ranges are provided, such as where "f" for example has a value of from 1 to about 10, that every value between is contemplated by the applicant and is included herein for all purposes. Therefore, every value can be relied upon to provider novel and inventive compositions and their uses.

In one aspect, each of $DHPD_a$, $DHPD_l$, $DHPD_p$ of formula (I) is a 3,4-dihydroxyhydrocinnamic acid residue, each of $L_b$, $L_k$, and $L_o$ are amide linkages, each of $L_d$, $L_i$ and $L_m$ represent bonds, each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons, wherein e, f and g each a value of 1, each $R_1$ and $R_3$ is a $CH_2$ and $R_2$ is a CH; and h is 6.

In another aspect of formula (I), each of $DHPD_a$, $DHPD_l$, $DHPD_p$ is a dopamine residue; each of $L_b$, $L_k$, and $L_o$ are urethane linkages between the dopamine residue and a the terminal portion of the polyethylene glycol polyether; each of $L_d$, $L_i$ and $L_m$ represent bonds; each of $PA_c$, $PA_j$ and $PA_n$ are polyethylene glycol polyether derivatives comprising a hydroxyl terminal residue which form the urethane linkage between the amine residue and the polyethylene glycol polyether derivative, each having a molecular weight of between about 1,500 and about 5,000 daltons; wherein e, f and g each a value of 1; each $R_1$ and $R_3$ is a $CH_2$ and $R_2$ is a CH; and h is 6.

In yet another aspect of formula (I), each of $DHPD_a$, $DHPD_l$, $DHPD_p$ is a dopamine residue; each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether; each of $L_d$, $L_i$ and $L_m$ represent bonds; each of $PA_c$, $PA_j$ and $PA_n$ are polyethylene glycol polyether derivatives comprising a hydroxyl terminal residue, each having a molecular weight of between about 1,500 and about 3,500 daltons; wherein e, f and g each a value of 1; each $R_1$ and $R_3$ is a $CH_2$ and $R_2$ is a CH; and h is 6.

In still yet another aspect of formula (I) each of $DHPD_a$, $DHPD_l$, $DHPD_p$ is a 3,4-dihydroxyhydrocinnamic acid residue; each of $L_b$, $L_k$, and $L_o$ are amide linkages; each of $L_d$, $L_i$ and $L_m$ represent bonds; each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons; wherein e, g and h each have a value of 1; each $R_T$ and $R_3$ is a $CH_2$ and $R_2$ is a CH; and f is 4. The molecular weights of $PA_c$, $PA_j$ and $PA_n$ are each about 1,500 daltons or the molecular weights of $PA_c$, $PA_j$ and $PA_n$ are each about 2,500 daltons or the molecular weights of $PA_c$, $PA_j$ and $PA_n$ are each about 3,300 daltons.

$L_b$, $L_k$, $L_o$ and $L_u$, if present, each individually, can be a C1 to about a C8 alkyl chain that can be branched or unbranched and/or substituted with substituents, such as for example, carbonyl functionalit(ies). Suitable examples include succinic acid, 3-methylglutaric acid, or glutaric acid residues. Further the alkyl chain can include one or more heteroatoms and/or one or more degrees of unsaturation. Alternatively, one or more of $L_b$, $L_k$, $L_o$ and $L_u$ can be a bond, e.g., an amide, ether, ester, urea, carbonate, or urethane linking group.

$R_1$, $R_2$, $R_3$, $R_4$ and/or $R_5$, each individually when present, can be a C1 to about a C8 carbon alky that can be that can be branched or unbranched and/or subtituted with substituents. Further the alkyl chain can include one or more heteroatoms and/or one or more degrees of unsaturation.

$L_d$, $L_i$, $L_m$ and $L_s$, if present, each individually, can be a C1 to about a C8 alkyl chain that can be branched or unbranched and/or substituted with substituents, such as for example, carbonyl functionalit(ies). Suitable examples include succinic acid, 3-methylglutaric acid, or glutaric acid residues. Further the alkyl chain can include one or more heteroatoms and/or one or more degrees of unsaturation. Alternatively, one or more of $L_d$, $L_i$, $L_m$ and $L_s$ can be a single bond, e.g., an amide, ether, ester, urea, carbonate, or urethane linking group.

Each $PA_c$, $PA_j$, $PA_n$ and $PA_t$, independently, if present, can be one of the PA's described herein.

"e" is a value from 1 to about 3.
"f" is a value from 1 to about 10.
"g" is a value from 1 to about 3.

"h" is a value from 1 to about 10.

"q" is a value from 0 to about 3.

"r" is a value from 0 to about 3;

Each $z^1$, $z^2$, and $z^3$, independently, if present, are each a value from about 1 to about 10.

Each $SubDHPD_a$, $SubDHPD_l$, $SubDHPD_p$, independently, if present, are each a DHPD as described herein that has at least two hydroxyl groups further substituted with another DHPD. Generally, such substitution can be accomplished by a condensation of the hydroxyl group with a carboxylic acid or carboxylic ester group of a DHPD. For example, dopamine can be reacted with 3,4-dihydroxyhydrocinnamic acid to form a substituted DHPD (a SubDHPD). See for example, Medhesive-089.

Each $AA_1$, $AA_2$ and $AA_3$, independently, if present, is an amino acid residue. Suitable amino acids include tyrosine, lysine and the like.

Each dd, ee and ff, independently, if present, is a value from 1 to about 10.

Each jj, kk and mm, independently, if present, is a value from about 1 to about 10.

The adhesives of the invention can be utilized for wound closure and materials of this type are often referred to as tissue sealants or surgical adhesives.

Typically, formulations of the invention (the adhesive composition) have a solids content of between about 10% to about 50% solids by weight, in particular between about 15% and about 40% by weight and particularly between about 20% and about 35% by weight.

Without wishing to be bound to a theory, it is believed that the addition of the preferred amino acid lysine, contributes to adhesive interactions on metal oxide surfaces through electrostatic interactions with negatively charged oxides. Cohesion or crosslinking is achieved via oxidation of DOPA catechol by sodium periodate ($NaIO_4$) to form reactive quinone. It is further theorized, again without wishing to be bound by a theory, that quinone can react with other nearby catechols and functional groups on surfaces, thereby achieving covalent crosslinking The adhesives of the invention can be utilized for wound closure, such as a dura sealant. One unique aspect of the adhesives of the invention is that they are biodegradable. The biodegradation can occur via cleavage of the linking groups or linkers by hydrolysis or enzymatic means.

As used herein, a wound includes damage to any tissue in a living organism. The tissue may be an internal tissue, such as the stomach lining, dura mater or pachymeninx or a bone, or an external tissue, such as the skin. As such a wound may include, but is not limited to, a gastrointestinal tract ulcer, a broken bone, a neoplasia, or cut or abraided skin. A wound may be in a soft tissue, such as the spleen, cardiovascular, or in a hard tissue, such as bone. The wound may have been caused by any agent, including traumatic injury, infection or surgical intervention.

As used herein, the adhesives/compositions of the invention can be considered "tissue sealants" which are substances or compositions that, upon application to a wound, seals the wound, thereby reducing blood loss and maintaining hemostasis.

Typically the adhesive composition of the invention is applied to the surface to be treated, e.g., repaired, as a formulation with a carrier (such as a pharmaceutically acceptable carrier) or as the material per se.

The phrase "pharmaceutically acceptable carrier" means a pharmaceutically-acceptable material, composition or vehicle, such as a liquid or solid filler, diluent, excipient, solvent or encapsulating material that can be combined with the adhesive compositions of the invention. Each carrier should be "acceptable" in the sense of being compatible with the other ingredients of the composition and not injurious to the individual. Some examples of materials which may serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; phosphate buffered saline with a neutral pH and other non-toxic compatible substances employed in pharmaceutical formulations.

Alternatively, the adhesive composition of the invention can be applied as a "patch" that includes any shaped substrate compatible with surgical implantation and capable of being coated by an inventive sealant. The adhesive compositions can be formulated for use as an aqueous suspension, a solution, a powder, a paste, a sheet, a ring, a stent, a cone, a plug, a pin, a screw and complex three-dimensional shapes contoured to be complementary to specific anatomical features. Inventive patch materials include collagen; polylactic acid; hyaluronic acid; fluoropolymers; silicones; knitted or woven meshes of, for example, cellulosic fibers, polyamides, rayon acetates and titanium; skin; bone; titanium and stainless steel. Alternatively, pericardial or other body tissue may be used instead of a collagen patch. More preferably, the collagen is a flexible, fibrous sheet readily formed into a variety of shapes that is bioabsorbable and has a thickness of 2 5 millimeters. Such fibrous sheet collagen is commercially available from a number of suppliers. A collagen patch serves to enhance sealant strength while allowing some penetration of the inventive tissue sealant thereto. Optionally, in a surgical setting, a dry or a wetted absorbent gauze is placed proximal to the wound site in order to wick away any excess inventive tissue sealant prior to cure.

The inventive tissue adhesive composition can be delivered in conjunction with a propellant that is provided in fluid communication with a spray nozzle tip. Propellants include aerosol propellants such as carbon dioxide, nitrogen, propane, fluorocarbons, dimethyl ether, hydrochlorofluorocarbon-22, 1-chloro-1,1-difluoroethane, 1,1-difluoroethane, and 1,1,1-trifluoro-2-fluoroethane, alone or in combination.

In certain embodiments an oxidant is included with the bioadhesive film layer. The oxidant can be incorporated into the polymer film or it can be contacted to the film at a later time. A solution could be sprayed or brushed onto either the adhesive surface or the tissue substrate surface. Alternatively, the construct can be dipped or submerged in a solution of oxidant prior to contacting the tissue substrate. In any situation, the oxidant upon activation, can help promote crosslinking of the multihydroxy phenyl groups with each other and/or tissue. Suitable oxidants include periodates and the like.

The invention further provides crosslinked bioadhesive constructs or hydrogels derived from the compositions described herein. For example, two DHDP moieties from two separate polymer chains can be reacted to form a bond between the two DHDP moieties. Typically, this is an oxidative/radical initiated crosslinking reaction wherein oxidants/initiators such as $NaIO_3$, $NaIO_4$, Fe III salts, ($FeCl_3$), Mn III salts (MnCl$_3$), H$_2$O$_2$, oxygen, an inorganic base, an organic base or an enzymatic oxidase can be used. Typically, a ratio of oxidant/initiator to DHDP containing material is between about 0.2 to about 1.0 (on a molar basis) (oxidant:DHDP). In one particular embodiment, the ratio is between about 0.25 to about 0.75 and more particularly between about 0.4 to about 0.6 (e.g., 0.5). It has been found that periodate is very effective in the preparation of crosslinked hydrogels of the invention. Additionally, it is possible that oxidation "activates" the DHPD(s) which allow it to form interfacial crosslinking with appropriate surfaces with functional group (i.e. biological tissues with —NH$_2$, —SH, etc.)

The DHDP containing material is put into a first aqueous solution having a pH between about 7 and about 10, e.g., a pH of about 9, with a saline content of between about 0.9 to about 1.8 percent on a weight basis. FD&C Blue No. 1 can be added in a concentration range of between about 0.005 and about 0.5 percent on a weight basis, in particular between about 0.005 and about 0.02, more particularly about 0.1 weight percent. The concentration of the polymer (DHPD containing material) can be between about 15 to about 60 percent on a weight basis, in particular between about 20 and about 50 percent and particularly about 30 weight percent.

A second solution is prepared prior to combining with the first solution. The second solution is an aqueous solution that contains between about 5 to about 15 milligrams (mg) of sodium periodate (NaIO$_4$) per ml of solution, in particular between about 8 and about 12 mg/ml and particularly between about 9 and about 10 mg/ml.

Typically, when the DHDP containing material is treated with an oxidant/initiator as described, the material sets (crosslinks) within 100 seconds, more particularly within 30 seconds, even more particularly 5 seconds, most particularly under 2 seconds and in particular within 1 second or less. For example, PEG20 k-(DMu)$_8$ gelled with in 2 seconds or less at a IO$_4$:DHP mole ratio of 5 in pH 9.0 saline solution.

In certain aspects of the invention, volumetric swelling of the DHDP containing material upon reaction is less than about 200%, in particular less than about 100% and particularly less than about 50%.

The burst strength of the DHDP containing material upon reaction is between about 60 and about 200 mm Hg/mm, more particularly between about 100 and about 200 mm Hg/mm and particularly between about 150 and about 200 mm Hg/mm.

In still another aspect, blends of the compounds of the invention described herein, can be prepared with various polymers. Polymers suitable for blending with the compounds of the invention are selected to impart non-covalent interactions with the compound(s), such as hydrophobic-hydrophobic interactions or hydrogen bonding with an oxygen atom on PEG and a substrate surface. These interactions can increase the cohesive properties of the film to a substrate. If a biopolymer is used, it can introduce specific bioactivity to the film, (i.e. biocompatibility, cell binding, immunogenicity, etc.).

Suitable polymers include, for example, polyesters, PPG, linear PCL-diols (MW 600-2000), branched PCL-triols (MW 900), wherein PCL can be replaced with PLA, PGA, PLGA, and other polyesters, amphiphilic block (di, tri, or multiblock) copolymers of PEG and polyester or PPG, tri-block copolymers of PCL-PEG-PCL (PCL MW=500-3000, PEG MW=500-3000), tri-block copolymers of PLA-PEG-PLA (PCL MW=500-3000, PEG MW=500-3000), wherein PCL and PLA can be replaced with PGA, PLGA, and other polyesters. Pluronic polymers (triblock, diblock of various MW) and other PEG, PPG block copolymers are also suitable. Hydrophilic polymers with multiple functional groups (—OH, —NH2, —COOH) contained within the polymeric backbone such as PVA (MW 10,000-100,000), poly acrylates and poly methacrylates, polyvinylpyrrolidone, and polyethylene imines are also suitable. Biopolymers such as polysaccharides (e.g., dextran), hyaluronic acid, chitosan, gelatin, cellulose (e.g., carboxymethyl cellulose), proteins, etc. which contain functional groups can also be utilized.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

Typically, blends of the invention include from about 0 to about 99.9% percent (by weight) of polymer to composition(s) of the invention, more particularly from about 1 to about 50 and even more particularly from about 1 to about 30.

The compositions of the invention, either a blend or a compound of the invention per se, can be applied to suitable substrates using conventional techniques. Coating, dipping, spraying, spreading and solvent casting are possible approaches.

The present invention surprisingly provides unique antifouling coatings/constructs that are suitable for application in, for example, urinary applications. The coatings could be used anywhere that a reduction in bacterial attachment is desired: dental unit waterlines, implantable orthopedic devices, cardiovascular devices, wound dressings, percutaneous devices, surgical instruments, marine applications, food preparation surfaces and utensils.

The present invention surprisingly provides unique bioadhesive constructs that are suitable to repair or reinforce damaged tissue.

Suitable supports include those that can be formed from natural materials, such as collagen, metal surfaces such as titanium, iron, steel, etc. or man made materials such as polypropylene, polyethylene, polybutylene, polyesters, PTFE, PVC, polyurethanes and the like. The support can be a solid surface such as a film, sheet, coupon or tube, a membrane, a mesh, a non-woven and the like. The support need only help provide a surface for the coating to adhere.

Other suitable supports can be formed from a natural material, such as collagen, pericardium, dermal tissues, small intestinal submucosa and the like. The support can be a film, a membrane, a mesh, a non-woven and the like. The support need only help provide a surface for the bioadhesive/coating to adhere. The support should also help facilitate physiological reformation of the tissue at the damaged site. Thus the constructs of the invention provide a site for remodeling via fibroblast migration, followed by subsequent native collagen deposition. For biodegradable support of either biological or synthetic origins, degradation of the support and the adhesive can result in the replacement of the bioadhesive construct by the natural tissues of the patient.

The coatings of the invention can include a compound of the invention or mixtures thereof or a blend of a polymer with one or more of the compounds of the invention. In one embodiment, the construct is a combination of a substrate, to which a blend is applied, followed by a layer(s) of one or more compounds of the invention.

In another embodiment, two or more layers can be applied to a substrate wherein the layering can be combinations of one or more blends or one or more compositions of the invention. The layering can alternate between a blend and a composition layer or can be a series of blends followed by a composition layer or vice versa.

It has interestingly been found that use of a blend advantageously has improved adhesion to the substrate surface. For example, a blend of a hydrophobic polymer with a composition of the invention should have improved adhesion to a hydrophobic substrate. Subsequent application of a composition as described herein to the blend layer then provides improved interfacial adhesion between the blend and provides for improved adhesive properties to the tissue to be adhered to as the hydrophobic polymer is not in the outermost layer.

Typically the loading density of the coating layer is from about 0.001 g/m$^2$ to about 200 g/m$^2$, more particularly from about 5 g/m$^2$ to about 150 g/m$^2$, and more particularly from about 10 g/m$^2$ to about 100 g/m$^2$. Thus, typically a coating has a thickness of from about 1 to about 200 nm. More typically for an adhesive, the thickness of the film is from about 1 to about 200 microns.

The following paragraphs enumerated consecutively from 1 through 106 provide for various aspects of the present invention. In one embodiment, in a first paragraph (1), the present invention provides a compound comprising formula (I):

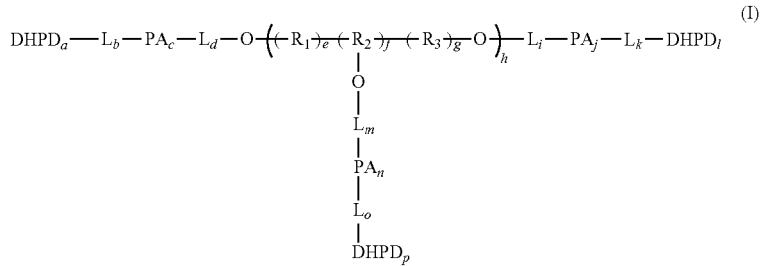

wherein each $DHPD_a$, $DHPD_l$, $DHPD_p$, independently, can be the same or different;

each $L_b$, $L_k$, and $L_o$, independently, can be the same or different; optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

e is a value from 1 to about 3;

f is a value from 1 to about 10;

g is a value from 1 to about 3;

h is a value from 1 to about 10;

each of $R_1$, $R_2$ and $R_3$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups; and each DHPD, independently, is a multihydroxy phenyl derivative.

2. The compound of paragraph 1, wherein each of $DHPD_a$, $DHPD_l$, $DHPD_p$ is either a dopamine, 3,4-dihydroxyphenylalanine, 3,4-dihydroxyphenyl ethanol or 3,4-dihydroxyhydrocinnamic acid residue.

3. The compound of either paragraphs 1 or 2, wherein each of $PA_c$, $PA_j$ and $PA_n$ is a polyethylene glycol polyether or derivative thereof.

4. The compound of any of paragraphs 1 through 3, wherein the molecular weight of each of the PAs is between about 1,500 and about 5,000 daltons.

5. The compound of any of paragraphs 1 through 4, wherein each of $L_b$, $L_k$, and $L_o$ are amide or urethane linkages and $L_d$, $L_i$ and $L_m$ represent ether bonds.

6. The compound of any of paragraphs 1 through 5, wherein each $R_1$ and $R_3$ is a $CH_2$ and $R_2$ is a CH.

7. The compound of any of paragraphs 1 through 6, wherein e and g each have a value of 1 and f is 4 or 6.

8. The compound of any of paragraphs 1 through 7, wherein h is 1.

9. The compound of paragraph 1, wherein each of $DHPD_a$, $DHPD_l$, $DHPD_p$ is a 3,4-dihydroxyhydrocinnamic acid residue;

each of $L_b$, $L_k$, and $L_o$ are amide linkages;

each of $L_d$, $L_i$ and $L_m$ represent ether bonds;

each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;

wherein e, f and g each have a value of 1;

each $R_1$ and $R_3$ is a $CH_2$ and $R_2$ is a CH; and h is 6.

10. The compound of paragraph 1, wherein each of $DHPD_a$, $DHPD_l$, $DHPD_p$ is a dopamine residue;

each of $L_b$, $L_k$, and $L_o$ are urethane linkages between the dopamine residue and a the terminal portion of the polyethylene glycol polyether;

each of $L_d$, $L_i$ and $L_m$ represent ether bonds;

each of $PA_c$, $PA_j$ and $PA_n$ are polyethylene glycol polyether derivatives comprising a hydroxyl terminal residue which form the urethane linkage between the amine residue and the polyethylene glycol polyether derivative, each having a molecular weight of between about 1,500 and about 5,000 daltons;

wherein e, f and g each have a value of 1;

each $R_1$ and $R_3$ is a $CH_2$ and $R_2$ is a CH; and h is 6.

11. The compound of paragraph 1, wherein each of $DHPD_a$, $DHPD_l$, $DHPD_p$ is a dopamine residue;

each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether;

each of $L_d$, $L_i$ and $L_m$ represent ether bonds;

each of $PA_c$, $PA_j$ and $PA_n$ are polyethylene glycol polyether derivatives comprising a hydroxyl terminal residue, each having a molecular weight of between about 1,500 and about 3,500 daltons;

wherein e, f and g each have a value of 1;

each $R_1$ and $R_3$ is a $CH_2$ and $R_2$ is a CH; and h is 6.

12. The compound of paragraph 1, wherein each of $DHPD_a$, $DHPD_l$, $DHPD_p$ is a 3,4-dihydroxyhydrocinnamic acid residue;
each of $L_b$, $L_k$, and $L_o$ are amide linkages;
each of $L_d$, $L_i$ and $L_m$ represent ether bonds;
each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;
wherein e, g and h each have a value of 1;
each $R_1$ and $R_3$ is a $CH_2$ and $R_2$ is a CH; and
f is 4.

13. The compound of paragraph 12, wherein the molecular weights of $PA_c$, $PA_j$ and $PA_n$ are each about 1,500 daltons.

14. The compound of paragraph 12, wherein the molecular weights of $PA_c$, $PA_j$ and $PA_n$ are each about 2,500 daltons.

15. The compound of paragraph 12, wherein the molecular weights of $PA_c$, $PA_j$ and $PA_n$ are each about 3,300 daltons.

16. A compound comprising formula (II):

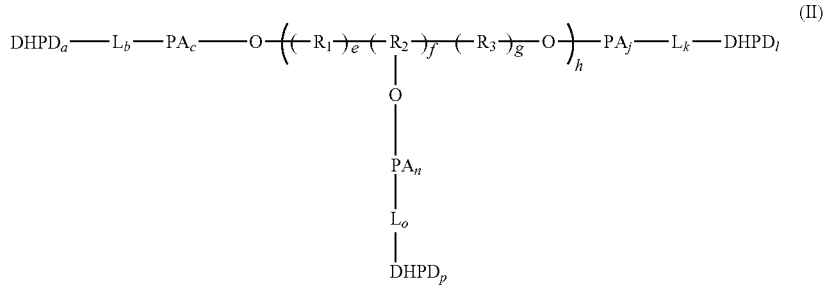

(II)

wherein
each $DHPD_a$, $DHPD_l$, $DHPD_p$, independently, can be the same or different;
each $L_b$, $L_k$, and $L_o$, independently, can be the same or different;
each $PA_c$, $PA_j$ and $PA_n$, independently, can be the same or different;
e is a value from 1 to about 3;
f is a value from 1 to about 10;
g is a value from 1 to about 3;
h is a value from 1 to about 10;
each of $R_1$, $R_2$ and $R_3$, independently, is a branched or unbranched alkyl group having at least 1 carbon atom;
each PA, independently, is a substantially poly(alkylene oxide) polyether or derivative thereof;
each L, independently, is a linker or is a suitable linking group selected from amide, ether, ester, urea, carbonate or urethane linking groups; and
each DHPD, independently, is a multihydroxy phenyl derivative.

17. The compound of paragraph 16, wherein each of $DHPD_a$, $DHPD_l$, $DHPD_p$ is either a dopamine, 3,4-dihydroxyphenyl alanine, 3,4-dihydroxyphenyl ethanol or 3,4-dihydroxyhydrocinnamic acid residue.

18. The compound of either paragraphs 16 or 17, wherein each of $PA_c$, $PA_j$ and $PA_n$ is a polyethylene glycol polyether or derivative thereof.

19. The compound of any of paragraphs 16 through 18, wherein the molecular weight of each of the PAs is between about 1,500 and about 3,500 daltons.

20. The compound of any of paragraphs 16 through 19, wherein each $R_1$ and $R_3$ is a $CH_2$ and $R_2$ is a CH.

21. The compound of any of paragraphs 16 through 20, wherein e, f and g each a value of 1.

22. The compound of any of paragraphs 16 through 21, wherein h is 1 or 6.

23. The compound of paragraph 16, wherein each of $DHPD_a$, $DHPD_l$, $DHPD_p$ is a 3,4-dihydroxyhydrocinnamic acid residue;
each of $L_b$, $L_k$, and $L_o$ are amide linkages;
each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;
wherein e, f and g each have a value of 1;
each $R_1$ and $R_3$ is a $CH_2$ and $R_2$ is a CH; and
h is 6.

24. The compound of paragraph 16, wherein each of $DHPD_a$, $DHPD_l$, $DHPD_p$ is a dopamine residue;
each of $L_b$, $L_k$, and $L_o$ are urethane linkages between the dopamine residue and a the terminal portion of the polyethylene glycol polyether;
each of $PA_c$, $PA_j$ and $PA_n$ are polyethylene glycol polyether derivatives comprising a hydroxyl terminal residue which form the urethane linkage between the amine residue and the polyethylene glycol polyether derivative, each having a molecular weight of between about 1,500 and about 5,000 daltons;
wherein e, f and g each have a value of 1;
each $R_1$ and $R_3$ is a $CH_2$ and $R_2$ is a CH; and
h is 6.

25. The compound of paragraph 16, wherein each of $DHPD_a$, $DHPD_l$, $DHPD_p$ is a dopamine residue;
each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether;
each of $PA_c$, $PA_j$ and $PA_n$ are polyethylene glycol polyether derivatives comprising a hydroxyl terminal residue, each having a molecular weight of between about 1,500 and about 3,500 daltons;
wherein e, f and g each have a value of 1;
each $R_1$ and $R_3$ is a $CH_2$ and $R_2$ is a CH; and
h is 6.

26. The compound of paragraph 16, wherein each of $DHPD_a$, $DHPD_l$, $DHPD_p$ is a 3,4-dihydroxyhydrocinnamic acid residue;
each of $L_b$, $L_k$, and $L_o$ are amide linkages;

each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;

wherein e, g and h each have a value of 1;

each $R_1$ and $R_3$ is a $CH_2$ and $R_2$ is a CH; and f is 4.

27. The compound of paragraph 26, wherein the molecular weights of $PA_c$, $PA_j$ and $PA_n$ are each about 1,500 daltons.

28. The compound of paragraph 26, wherein the molecular weights of $PA_c$, $PA_j$ and $PA_n$ are each about 2,500 daltons.

29. The compound of paragraph 26, wherein the molecular weights of $PA_c$, $PA_j$ and $PA_n$ are each about 3,300 daltons.

30. A compound comprising formula (III):

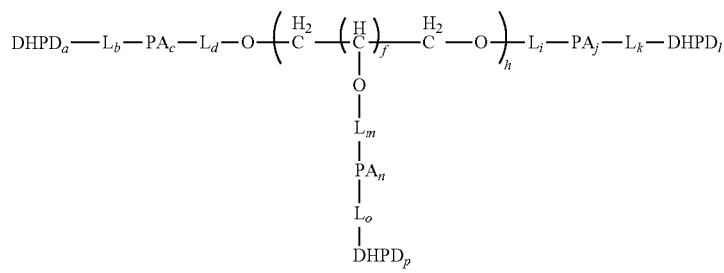

(III)

wherein each $DHPD_a$, $DHPD_l$, $DHPD_p$, independently, can be the same or different;

each $L_b$, $L_k$, and $L_o$, independently, can be the same or different;

optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

f is a value from 1 to about 10;

h is a value from 1 to about 10;

each PA, independently, is a substantially poly(alkylene oxide) polyether or derivative thereof;

each L, independently, is a linker or is a suitable linking group selected from amide, ether, ester, urea, carbonate or urethane linking groups; and each DHPD, independently, is a multihydroxy phenyl derivative.

31. The compound of paragraph 30, wherein each of $DHPD_a$, $DHPD_l$, $DHPD_p$ is either a dopamine, 3,4-dihydroxyphenyl alanine, 3,4-dihydroxyphenyl ethanol or 3,4-dihydroxyhydrocinnamic acid residue.

32. The compound of either paragraphs 30 or 31, wherein each of $PA_c$, $PA_j$ and $PA_n$ is a polyethylene glycol polyether or derivative thereof.

33. The compound of any of paragraphs 30 through 32, wherein the molecular weight of each of the PAs is between about 1,500 and about 5,000 daltons.

34. The compound of any of paragraphs 30 through 33, wherein each of $L_b$, $L_k$, and $L_o$ are amide or urethane linkages and $L_d$, $L_i$ and $L_m$ represent ether bonds.

35. The compound of any of paragraphs 30 through 34, wherein h is 1 or 6.

36. The compound of paragraph 30, wherein each of $DHPD_a$, $DHPD_l$, $DHPD_p$ is a 3,4-dihydroxyhydrocinnamic acid residue;

each of $L_b$, $L_k$, and $L_o$ are amide linkages;

each of $L_d$, $L_i$ and $L_m$ represent ether bonds;

each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons; and h is 6.

37. The compound of paragraph 30, wherein each of $DHPD_a$, $DHPD_l$, $DHPD_p$ is a dopamine residue;

each of $L_b$, $L_k$, and $L_o$ are urethane linkages between the dopamine residue and a the terminal portion of the polyethylene glycol polyether;

each of $L_d$, $L_i$ and $L_m$ represent ether bonds;

each of $PA_c$, $PA_j$ and $PA_n$ are polyethylene glycol polyether derivatives comprising a hydroxyl terminal residue which form the urethane linkage between the amine residue and the polyethylene glycol polyether derivative, each having a molecular weight of between about 1,500 and about 5,000 daltons; and h is 6.

38. The compound of paragraph 1, wherein each of $DHPD_a$, $DHPD_l$, $DHPD_p$ is a dopamine residue;

each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether;

each of $L_d$, $L_i$ and $L_m$ represent ether bonds; each of $PA_c$, $PA_j$ and $PA_n$ are polyethylene glycol polyether derivatives comprising a hydroxyl terminal residue, each having a molecular weight of between about 1,500 and about 3,500 daltons; and h is 6.

39. The compound of paragraph 1, wherein each of $DHPD_a$, $DHPD_l$, $DHPD_p$ is a 3,4-dihydroxyhydrocinnamic acid residue;

each of $L_b$, $L_k$, and $L_o$ are amide linkages;

each of $L_d$, $L_i$ and $L_m$ represent ether bonds;

each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;

f is 4; and h is 1.

40. The compound of paragraph 39, wherein the molecular weights of $PA_c$, $PA_j$ and $PA_n$ are each about 1,500 daltons.

41. The compound of paragraph 39, wherein the molecular weights of $PA_c$, $PA_j$ and $PA_n$ are each about 2,500 daltons.

42. The compound of paragraph 39, wherein the molecular weights of $PA_c$, $PA_j$ and $PA_n$ are each about 3,300 daltons.

43. A compound comprising formula (IV):

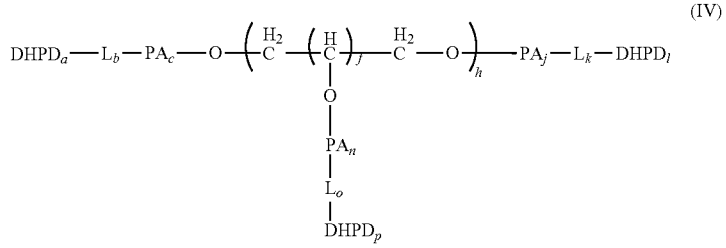

(IV)

wherein
each $DHPD_a$, $DHPD_l$, $DHPD_p$, independently, can be the same or different;
each $L_b$, $L_k$, and $L_o$, independently, can be the same or different;
each $PA_c$, $PA_j$ and $PA_n$, independently, can be the same or different;
f is a value from 1 to about 10
h is a value from 1 to about 10;
each PA, independently, is a substantially poly(alkylene oxide) polyether or derivative thereof;
each L, independently, is a linker or is a suitable linking group selected from amide, ether, ester, urea, carbonate or urethane linking groups; and
each DHPD, independently, is a multihydroxy phenyl derivative.

44. The compound of paragraph 43, wherein each of $DHPD_a$, $DHPD_l$, $DHPD_p$ is either a dopamine, 3,4-dihydroxyphenyl alanine, 3,4-dihydroxyphenyl ethanol or 3,4-dihydroxyhydrocinnamic acid residue.

45. The compound of either paragraphs 43 or 44, wherein each of $PA_c$, $PA_j$ and $PA_n$ is a polyethylene glycol polyether or derivative thereof.

46. The compound of any of paragraphs 43 through 45, wherein the molecular weight of each of the PAs is between about 1,500 and about 3,500 daltons.

47. The compound of any of paragraphs 43 through 46, wherein f is 4 or 6.

48. The compound of paragraph 43, wherein each of $DHPD_a$, $DHPD_l$, $DHPD_p$ is a 3,4-dihydroxyhydrocinnamic acid residue;
each of $L_b$, $L_k$, and $L_o$ are amide linkages;
each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;
f is 1; and
h is 6.

49. The compound of paragraph 43, wherein each of $DHPD_a$, $DHPD_l$, $DHPD_p$ is a dopamine residue;
each of $L_b$, $L_k$, and $L_o$ are urethane linkages between the dopamine residue and a the terminal portion of the polyethylene glycol polyether;
each of $PA_c$, $PA_j$ and $PA_n$ are polyethylene glycol polyether derivatives comprising a hydroxyl terminal residue which form the urethane linkage between the amine residue and the polyethylene glycol polyether derivative, each having a molecular weight of between about 1,500 and about 5,000 daltons;
f is 1; and
h is 6.

50. The compound of paragraph 43, wherein each of $DHPD_a$, $DHPD_l$, $DHPD_p$ is a dopamine residue;
each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether;
each of $PA_c$, $PA_j$ and $PA_n$ are polyethylene glycol polyether derivatives comprising a hydroxyl terminal residue, each having a molecular weight of between about 1,500 and about 3,500 daltons;
f is 1; and
h is 6.

51. The compound of paragraph 43, wherein each of $DHPD_a$, $DHPD_l$, $DHPD_p$ is a 3,4-dihydroxyhydrocinnamic acid residue;
each of $L_b$, $L_k$, and $L_o$ are amide linkages; each of $PA_c$, $PA_j$ and $PA_n$ are polyethylene glycol polyether derivatives each comprising an amine terminal residue which form the amide linkages between the acid residue and the polyethylene glycol polyether derivative, each having a molecular weight of between about 1,500 and about 3,500 daltons;
f is 4; and
h is 1.

52. The compound of paragraph 51, wherein the molecular weights of $PA_c$, $PA_j$ and $PA_n$ are each about 1,500 daltons.

53. The compound of paragraph 51, wherein the molecular weights of $PA_c$, $PA_j$ and $PA_n$ are each about 2,500 daltons.

54. The compound of paragraph 51, wherein the molecular weights of $PA_c$, $PA_j$ and $PA_n$ are each about 3,300 daltons.

55. A compound comprising formula (V):

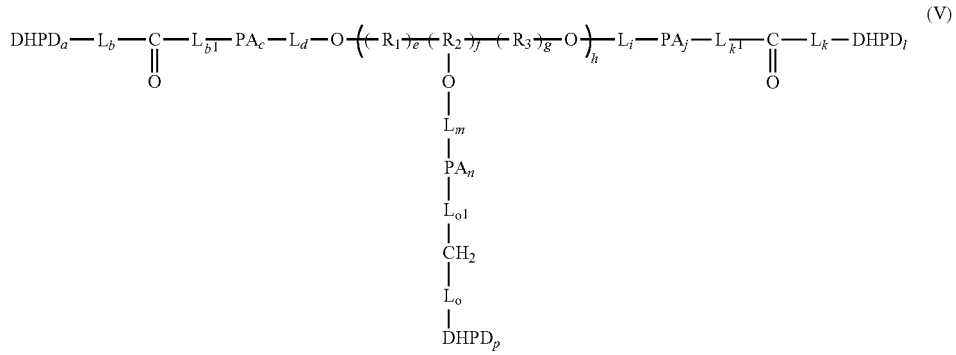

wherein each $DHPD_a$, $DHPD_l$, $DHPD_p$, independently, can be the same or different;

each $L_b$, $L_k$, and $L_o$, independently, can be the same or different;

each $L_b^1$, $L_k^1$, and $L_o^1$, independently, can be the same or different;

optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

e is a value from 1 to about 3;

f is a value from 1 to about 10;

g is a value from 1 to about 3;

h is a value from 1 to about 10;

each of $R_1$, $R_2$ and $R_3$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups; and each DHPD, independently, is a multihydroxy phenyl derivative.

56. The compound of paragraph 55, wherein each $DHPD_a$, $DHPD_l$, $DHPD_p$, is a dopamine residue;

each $L_b$, $L_k$, and $L_o$, is NH;

each $L_b^1$, $L_k^1$, and $L_o^1$ is NH;

each $L_d$, $L_i$ and $L_m$, form an ether bond;

each $PA_c$, $PA_j$ and $PA_n$, are the same;

e is 1;

f is 1 or 4;

g is 1;

h is 1, 4 or 6;

$R_1$ and $R_3$ are each $CH_2$; and $R_2$ is CH.

57. The compound of paragraph 1, wherein each $DHPD_a$, $DHPD_l$, $DHPD_p$, is a dihydroxy benzoic acid residue;

each $L_b$, $L_k$, and $L_o$, is an amide bond;

each $L_d$, $L_i$ and $L_m$, form an ether bond;

each $PA_c$, $PA_j$ and $PA_n$, are the same;

e is 1;

f is 1;

g is 1;

h is 4 or 6;

$R_1$ and $R_3$ are each $CH_2$; and $R_2$ is CH.

58. A compound comprising formula (VI)

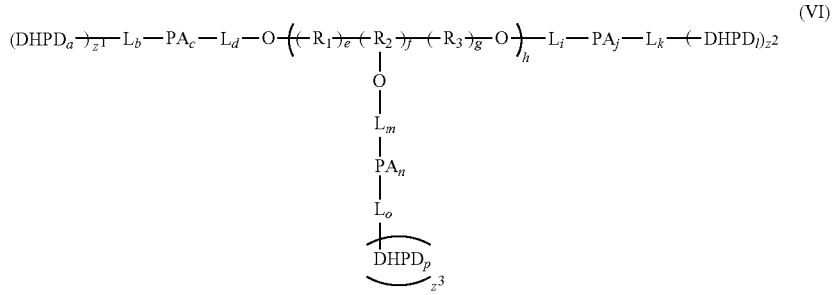

wherein each $DHPD_a$, $DHPD_l$, $DHPD_p$ is a 3,4-dihydroxy-phenylalanine residue;

each $L_b$, $L_k$, and $L_o$, independently, can be the same or different;

optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

e is a value from 1 to about 3;

f is a value from 1 to about 10;

g is a value from 1 to about 3;

h is a value from 1 to about 10;

each $z^1$, $z^2$, and $z^3$, independently, are each a value from about 1 to about 10;

each of $R_1$, $R_2$ and $R_3$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups.

59. The compound of paragraph 58, wherein
each $L_b$, $L_k$, and $L_a$, is and amide bond;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$;
$R_2$ is CH; and
each $z^1$, $z^2$, and $z^3$, independently, are each a value about 4.

60. A compound comprising the formula (VII):

f is a value from 1 to about 10;
g is a value from 1 to about 3;
h is a value from 2 to about 10;
q is a value from 0 to about 3;
r is a value from 0 to about 3;
each of $R_1$, $R_2$, $R_3$, $R_4$, and $R_5$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups; and each DHPD, independently, is a multihydroxy phenyl derivative.

61. The compound of paragraph 60, wherein
each $DHPD_a$, $DHPD_l$, $DHPD_p$, and $DHP_v$, is DOHA;
each $L_b$, $L_k$, $L_o$ and $L_u$, is an amide bond;
each $L_d$, $L_i$, $L_m$ and $L_s$, is an ether bond;

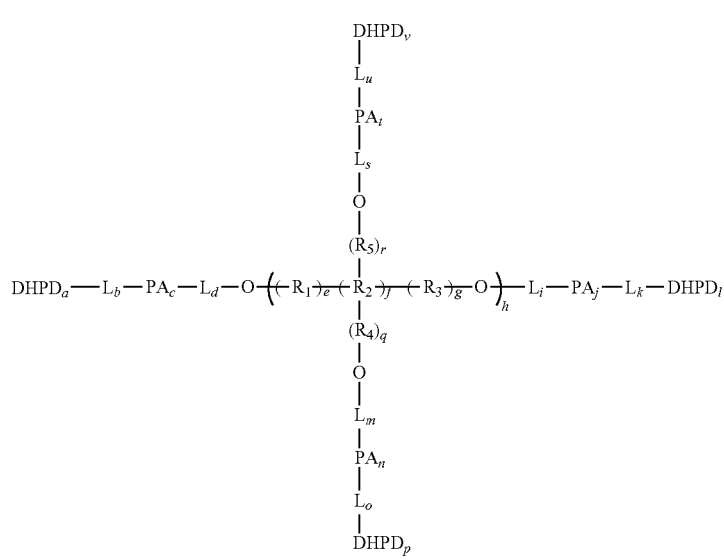

(VII)

wherein
each $DHPD_a$, $DHPD_l$, $DHPD_p$, and $DHP_v$, independently, can be the same or different;
each $L_b$, $L_k$, $L_o$ and $L_u$, independently, can be the same or different;
optionally, each $L_d$, $L_i$, $L_m$ and $L_s$, if present, can be the same or different and if not present, represent a bond between the O and respective PA of the compound;
each $PA_c$, $PA_j$, $PA_n$, and $PA_t$, independently, can be the same or different;
e is a value from 1 to about 3;

each $PA_c$, $PA_j$, $PA_n$, and $PA_t$, are the same;
e is 1;
f is 1;
g is 1;
h is 2;
q is 1;
r is 1;
each of $R_1$, $R_3$, $R_4$, and $R_5$, is a $CH_2$; and
$R_2$, is CH.

62. A compound comprising the formula (VIII):

$$\text{DHPDSub}_a-L_b-PA_c-L_d-O-\left(\left(R_1\right)_e\left(R_2\right)_f\left(R_3\right)_g-O\right)_h-L_i-PA_j-L_k-\text{SubDHPD}_l$$

with a branch from $R_2$:
$$|\ O\ |\ L_m\ |\ PA_n\ |\ L_o\ |\ \text{SubDHPD}_p$$

(VIII)

wherein each $\text{SubDHPD}_a$, $\text{SubDHPD}_l$, $\text{SubDHPD}_p$, independently, can be the same or different;

each $L_b$, $L_k$, and $L_o$, independently, can be the same or different;

optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

e is a value from 1 to about 3;
f is a value from 1 to about 10;
g is a value from 1 to about 3;
h is a value from 1 to about 10;

each of $R_1$, $R_2$ and $R_3$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups; and each SubDHPD, independently, is a multihydroxy phenyl derivative that is further substituted at one or more of the hydroxyl groups with a DHPD multihydroxy phenyl group.

63. The compound of paragraph 62, wherein
each $\text{SubDHPD}_a$, $\text{SubDHPD}_l$, $\text{SubDHPD}_p$ are the same;
each $L_b$, $L_k$, and $L_o$, is a urethane bond;
each $L_d$, $L_i$ and $L_m$, is an ether bond;
each $PA_c$, $PA_j$ and $PA_n$, are the same;
e is 1;
f is 1;
g is 1;

h is 4 or 6;
$R_1$ and $R_3$ are each $CH_2$;
$R_2$ is CH; and
each SubDHPD, independently, is substituted at least two of the hydroxyl groups with a DHPD multihydroxy phenyl group.

64. A compound comprising the formula (IX):

$$\left[\left(AA_1\right)_{dd}-\left(DHPD_a\right)_{z1}\right]_{jj}-L_b-PA_c-L_d-O-\left(\left(R_1\right)_e\left(R_2\right)_f\left(R_3\right)_g-O\right)_h-L_i-PA_j-L_k-\left[\left(DHPD_l\right)_{z2}-\left(AA_2\right)_{ee}\right]_{kk}$$

with branch:
$$|\ O\ |\ L_m\ |\ PA_n\ |\ L_o\ |\ \left[\left(DHPD_p\right)_{z3}-\left(AA_3\right)_{ff}\right]_{mm}$$

(IX)

wherein
each $\text{DHPD}_a$, $\text{DHPD}_l$, $\text{DHPD}_p$ is a 3,4-dihydroxy-phenylalanine residue;

each $L_b$, $L_k$, and $L_o$, independently, can be the same or different;

optionally, each $L_d$, $L_i$ and $L_m$, if present, can be the same or different and if not present, represent a bond between the O and respective PA of the compound;

each $PA_c$, $PA_j$ and $PA_n$, independently, can be the same or different;

e is a value from 1 to about 3;
f is a value from 1 to about 10;
g is a value from 1 to about 3;
h is a value from 1 to about 10;

each $z^1$, $z^2$, and $z^3$, independently, are each a value from about 1 to about 10;

each $AA_1$, $AA_2$ and $AA_3$, independently, is an amino acid residue;

each dd, ee and ff, independently, is a value from 1 to about 10;

each jj, kk and mm, independently, is a value from about 1 to about 10;

each of $R_1$, $R_2$ and $R_3$, independently, is a branched or unbranched alkyl group having at least 1 carbon atom;

each PA, independently, is a substantially poly(alkylene oxide) polyether or derivative thereof;

each L, independently, is a linker or is a suitable linking group selected from amide, ether, ester, urea, carbonate or urethane linking groups.

65. The compound of paragraph 64, wherein
each $L_b$, $L_k$, and $L_o$, is an amide bond;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$;
$R_2$ is CH;
each $z^1$, $z^2$, and $z^3$, independently, are each a value about 3;
each $AA_1$, $AA_2$ and $AA_3$, is lysine residue;
each dd, ee and ff, independently, has a value of about 1 to about 3; and
each jj, kk and mm, independently, has a value of about 1 to about 3.

66. The compound of paragraph 1, wherein
each $DHPD_a$, $DHPD_j$, $DHPD_p$, is a dihydroxy benzoic acid residue;
each $L_b$, $L_k$, and $L_o$, is O;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$; and
$R_2$ is CH.

67. The compound of paragraph 1, wherein
each $DHPD_a$, $DHPD_j$, $DHPD_p$, is a gallic acid residue;
each $L_b$, $L_k$, and $L_o$, is NH;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$; and
$R_2$ is CH.

68. The compound of paragraph 1, wherein
each $DHPD_a$, $DHPD_j$, $DHPD_p$, is a gallic acid residue;
each $L_b$, $L_k$, and $L_o$, is O;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$; and
$R_2$ is CH.

69. The compound of paragraph 1, wherein
each $DHPD_a$, $DHPD_j$, $DHPD_p$, is a 2,3,4 trihydroxybenzoic acid residue;
each $L_b$, $L_k$, and $L_o$, is O;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$; and
$R_2$ is CH.

70. The compound of paragraph 1, wherein
each $DHPD_a$, $DHPD_j$, $DHPD_p$, is a 3,4 dihydroxycinnamic acid residue;
each $L_b$, $L_k$, and $L_o$, is NH;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$; and
$R_2$ is CH.

71. The compound of paragraph 1, wherein
each $DHPD_a$, $DHPD_j$, $DHPD_p$, is a 3,4 dihydroxycinnamic acid residue;
each $L_b$, $L_k$, and $L_o$, is O;
each $L_d$, $L_i$ and $L_m$, form an ether bond;
each $PA_c$, $PA_j$ and $PA_n$, are the same;
e is 1;
f is 1;
g is 1;
h is 4 or 6;
$R_1$ and $R_3$ are each $CH_2$; and
$R_2$ is CH.

72. The compound of paragraph 1, wherein each of $DHPD_a$, $DHPD_j$, $DHPD_p$ is a multihydroxy benzylamine residue;
each of the linkers, $L_b$, $L_k$, and $L_o$, form an amide linkage between the benzylamine residue and one terminal portion of a dicarboxylic acid residue and an ester between the second terminal portion of the dicarboxylic acid residue and the terminal portion of the polyethylene glycol polyether;
each of $L_d$, $L_i$ and $L_m$ represent ether bonds;
each of $PA_c$, $PA_j$ and $PA_n$ are polyethylene glycol polyether derivatives comprising a hydroxyl terminal residue, each having a molecular weight of between about 1,500 and about 3,500 daltons;
e is 1;
f is 1;
g is 1;
h is 6;
$R_1$ and $R_3$ are each $CH_2$; and
$R_2$ is CH.

73. The compound of paragraph 72, wherein the multihydroxy benzylamine residue is 3,4 dihydroxybenzylamine, and the dicarboxylic acid residue is glutaric acid.

74. The compound of paragraph 1, wherein each of $DHPD_a$, $DHPD_j$, $DHPD_p$ is a dopamine residue;
each of the linkers, $L_b$, $L_k$, and $L_o$, form an amide linkage between the dopamine residue and one terminal portion of a dicarboxylic acid residue and an ester between the second terminal portion of the dicarboxylic acid residue and the terminal portion of the polyethylene glycol polyether;
each of $L_d$, $L_i$ and $L_m$ represent ether bonds;
each of $PA_c$, $PA_j$ and $PA_n$ are polyethylene glycol polyether derivatives comprising a hydroxyl terminal residue, each having a molecular weight of between about 1,500 and about 5,000 daltons;
e is 1;
f is 1;
g is 1;
h is 6;
$R_1$ and $R_3$ are each $CH_2$; and
$R_2$ is CH.

75. The compound of paragraph 1, wherein each of $DHPD_a$, $DHPD_j$, $DHPD_p$ is a multihydroxyphenylethylamine residue;

each of the linkers, $L_b$, $L_k$, and $L_o$, form an amide linkage between the amine residue and one terminal portion of a dicarboxylic acid residue and an ester between the second terminal portion of the dicarboxylic acid residue and the terminal portion of the polyethylene glycol polyether;

each of $L_d$, $L_i$ and $L_m$ represent ether bonds;

each of $PA_c$, $PA_j$ and $PA_n$ are polyethylene glycol polyether derivatives comprising a hydroxyl terminal residue, each having a molecular weight of between about 1,500 and about 3,500 daltons; and h is 6.

76. The compound of paragraph 75, wherein the multihydroxyphenyethylamine residue is 3,4 dihydroxyphenylethylamine and the dicarboxylic acid residue is 3-methyl glutaric acid or 2,2 dimethylglutaric acid.

77. The compound of paragraph 30, wherein each of $DHPD_a$, $DHPD_l$, $DHPD_p$ is a 3,4-dihydroxyhydrocinnamic acid residue;

each of $L_b$, $L_k$, and $L_o$ are ester linkages;

each of $L_d$, $L_i$ and $L_m$ represent ether bonds;

each of $PA_c$, $PA_j$ and $PA_n$ are polyethylene glycol polyether derivatives each comprising a hydroxy terminal residue which form the ester linkages between the acid residue and the polyethylene glycol polyether derivative, each having a molecular weight of between about 1,500 and about 3,500 daltons; and h is 6.

78. The compound of paragraph 55, wherein each $DHPD_a$, $DHPD_l$, $DHPD_p$, is a dopamine residue;

each $L_b$, $L_k$, and $L_o$, is NH;

each $L_b^1$, $L_k^1$, and $L_o^1$ is 0;

each $L_d$, $L_i$ and $L_m$, form an ether bond;

each $PA_c$, $PA_j$ and $PA_n$, are the same;

e is 1;

f is 1 or 4;

g is 1;

h is 1, 4 or 6;

$R_1$ and $R_3$ are each $CH_2$; and $R_2$ is CH.

79. The compound of paragraph 60, wherein each $DHPD_a$, $DHPD_l$, $DHPD_p$, and $DHP_v$, is a benzoic acid residue;

each $L_b$, $L_k$, $L_o$ and $L_u$, is an amide bond;

each $L_d$, $L_m$ and $L_s$, is an ether bond;

each $PA_c$, $PA_j$, $PA_n$, and $PA_t$, are the same;

e is 1;

f is 1;

g is 1;

h is 2;

q is 1;

r is 1;

each of $R_1$, $R_3$, $R_4$, and $R_5$, is a $CH_2$; and $R_2$, is CH.

80. A compound comprising the formula (X):

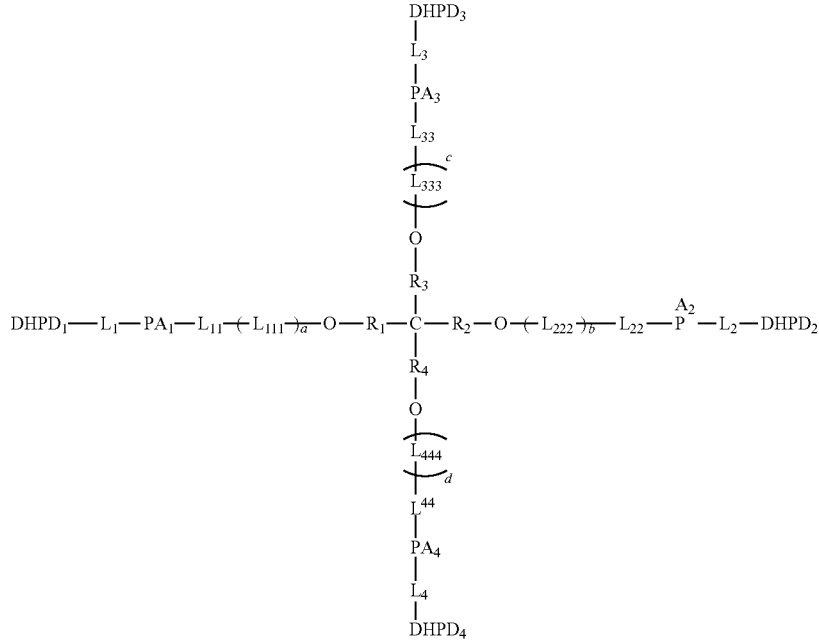

wherein each $DHPD_1$, $DHPD_2$, $DHPD_3$ and $DHPD_4$, independently, can be the same or different;

each $L_1$, $L_2$, $L_3$ and $L_4$, independently, can be either the same linking group or different linking groups;

each $PA_1$, $PA_2$, $PA_3$ and $PA_4$, independently, can be either the same or different;

each $L_{11}$, $L_{22}$, $L_{33}$ and $L_{44}$, independently, can be either the same linker or different linkers;

each $L_{111}$, $L_{222}$, $L_{333}$ and $L_{444}$, independently, can be the same linker or a different linkers;

each a, b, c and d, independently, is a value from 1 to about 100;

each PA, independently, is a substantially poly(alkylene oxide) polyether or derivative thereof; and each DHPD, independently, is a multihydroxy phenyl derivative.

81. The compound of paragraph 80, wherein each $DHPD_1$, $DHPD_2$, $DHPD_3$ and $DHPD_4$ is a 3,4-dihydroxyhydrocinnamic acid residue;

each $L_1$, $L_2$, $L_3$ and $L_4$ forms an amide linkage;

each $PA_1$, $PA_2$, $PA_3$ and $PA_4$ is a polyethylene glycol polyether or derivative thereof;

each $L_{11}$, $L_{22}$, $L_{33}$ and $L_{44}$ is a linker;
each $L_{111}$, $L_{222}$, $L_{333}$ and $L_{444}$ is a linker;
each of $R_1$, $R_2$, $R_3$ and $R_4$ is a —$CH_2$—; and
a, b, c and d are each about 4 to about 20.

82. The compound of paragraph 81, wherein each $L_{11}$, $L_{22}$, $L_{33}$ and $L_{44}$ is a glycolic acid residue, each $L_{111}$, $L_{222}$, $L_{333}$ and $L_{444}$ is a lactic acid residue and a, b, c and d are each about 14.

83. The compound of paragraph 82, wherein each $PA_1$, $PA_2$, $PA_3$ and $PA_4$ is a polyethylene glycol polyether or derivative thereof having a molecular weight of about 2000.

84. A compound comprising the formula ($X_1$):

$$C[R_1-O-(L_{111})_a-L_{11}-PA_1-L_1-DHPD]_4$$

wherein
DHPD is a multihydroxy phenyl derivative;
each $L_1$ is a linking group;
each $PA_1$ is a substantially poly(alkylene oxide) polyether or derivative thereof;
each $L_{11}$ is a linker;
each $L_{111}$ is a linker;
a is a value from 1 to about 100; and
$R_1$ is a branched or unbranched alkyl group having at least 1 carbon atom.

85. The compound of paragraph 84, wherein DHPD is a 3,4-dihydroxyhydrocinnamic acid residue, $L_1$ is an amide linkage, $PA_1$ is a polyethylene glycol polyether or derivative thereof, $L_{11}$ is a glycolic acid residue, $L_{111}$ is a lactic acid residue, a is about 14 and $R_1$ is a methylene.

86. The compound of paragraph 55, wherein
each $DHPD_a$, $DHPD_l$, $DHPD_p$, is a dopamine residue;
each $L_b$, $L_k$, and $L_o$ is NH;
each $L_b^1$, $L_k^1$, and $L_o^1$ is a polylactic acid residue;
each $L_d$, $L_i$ and $L_m$, form an ester bond;
each $PA_c$, $PA_j$ and $PA_n$, are the same;
e is 1;
f is 1;
g is 1;
h is 6;
$R_1$ and $R_3$ are each $CH_2$; and
$R_2$ is CH.

87. The compound of paragraph 55, wherein
each $DHPD_a$, $DHPD_l$, $DHPD_p$ is a dopamine residue;
each $L_b$, $L_k$, and $L_o$ is a methylamino benzoate residue;
each $L_b^1$, $L_k^1$, and $L_o^1$ is an ether bond;
each $L_d$, $L_i$ and $L_m$, is an ether bond;
each $PA_c$, $PA_j$ and $PA_n$, are the same;
e is 1;
f is 1;
g is 1;
h is 6;
$R_1$ and $R_3$ are each $CH_2$; and
$R_2$ is CH.

88. The compound of paragraph 55, wherein
each $DHPD_a$, $DHPD_l$, $DHPD_p$ is a dopamine residue, provided there can be two of each $DHPD_a$, $DHPD_l$, $DHPD_p$ per $L_b$, $L_k$, and $L_o$;
each $L_b$, $L_k$, and $L_o$ is a dimethylaminoterephthalate residue;
each $L_b^1$, $L_k^1$, and $L_o^1$ is an ether bond;
each $L_d$, $L_i$ and $L_m$, is an ether bond;
each $PA_c$, $PA_j$ and $PA_n$, are the same;
e is 1;
f is t;
g is 1;
h is 6;
$R_1$ and $R_3$ are each $CH_2$; and
$R_2$ is CH.

89. A compound comprising formula (XII)

$$DHPD_a-L_1-FnL_1-L_b-PA_c-L_d-O-(\!(R_1)_e-(R_2)_f-(R_3)_g-O)_h-L_i-PA_j-L_k-FnL_2-L_6-DHPD_l$$

with branches:
$L_2-DHPD_a^1$ (from first segment)
$L_m-PA_n-L_o-FnL_3-L_4-DHPD_p^1$; $L_3-DHPD_p$ (from middle O)
$L_5-DHPD_l^1$ (from last segment)

each $DHPD_a$, $DHPD_l$, $DHPD_p$, $DHPD_a^1$, $DHPD_l^1$, $DHPD_p^1$, independently, can be the same or different;
each $L_1$, $L_2$, $L_3$, $L_4$, $L_5$ and $L_6$, independently, can be the same or different;
each $FnL_1$, $FnL_2$ and $FnL_3$, independently, can be the same or different;
each $L_b$, $L_k$, and $L_o$, independently, can be the same or different;
optionally, each $L_d$, $L_i$ and $L_m$, if present, can be the same or different and if not present, represent a bond between the O and respective PA of the compound;
each $PA_c$, $PA_j$ and $PA_n$, independently, can be the same or different;
e is a value from 1 to about 3;
f is a value from 1 to about 10;
g is a value from 1 to about 3;
h is a value from 1 to about 10;
each of $R_1$, $R_2$ and $R_3$, independently, is a branched or unbranched alkyl group having at least 1 carbon atom;
each PA, independently, is a substantially poly(alkylene oxide) polyether or derivative thereof;
each FnL, independently, is a functional linker;
each L, independently, is a linker or is a suitable linking group selected from amide, ether, ester, urea, carbonate or urethane linking group; and
each DHPD, independently, is a multihydroxy phenyl derivative.

90. The compound of paragraph 89, wherein
each $DHPD_a$, $DHPD_l$, $DHPD_p$, $DHPD_a^1$, $DHPD_1^1$, $DHPD_p^1$, is a 3,4-dihydrocinnamic acid;
each $L_1$, $L_2$, $L_3$, $L_4$, $L_5$ and $L_6$ is an amide bond;

each $FnL_1$, $FnL_2$ and $FnL_3$ is a lysine residue;
each $L_b$, $L_k$, and $L_o$ is an ester bond;
each $L_d$, $L_i$ and $L_m$, represent a bond between the O and respective PA of the compound;
each $PA_c$, $PA_j$ and $PA_n$ is each a substantially poly(alkylene oxide) polyether residue;
e is a value from 1 to about 3;
f is a value from 1 to about 10;
g is a value from 1 to about 3;
h is a value from 1 to about 10;
each of $R_1$ and $R_3$ are each —$CH_2$—; and
$R_2$ is —CH.

91. The compound of paragraph 90, wherein e, f and g are each 1, h is 6 and $PA_c$, $PA_j$ and $PA_n$ each have a molecular weight of about 2464.

92. The compound of paragraph 90, wherein e, f and g are each 1, h is 6 and $PA_c$, $PA_j$ and $PA_n$ each have a molecular weight of about 4928.

93. The compound of paragraph 89, wherein
each $DHPD_a$, $DHPD_j$, $DHPD_p$, $DHPD_a^1$, $DHPD_1^1$, $DHPD_p^1$, is a 3,4-dihydrocinnamic acid;
each $L_1$, $L_2$, $L_3$, $L_4$, $L_5$ and $L_6$ is an amide bond;
each $FnL_1$, $FnL_2$ and $FnL_3$ is an aspartic acid residue;
each $L_b$, $L_k$, and $L_o$ is an ester bond;
each $L_d$, $L_i$ and $L_m$, represent a bond between the O and respective PA of the compound;
each $PA_c$, $PA_j$ and $PA_n$ is each a substantially poly(alylene oxide) polyether residue;
e is a value from 1 to about 3;
f is a value from 1 to about 10;
g is a value from 1 to about 3;
h is a value from 1 to about 10;
each of $R_1$ and $R_3$ are each —$CH_2$—; and
$R_2$ is —CH.

94. The compound of paragraph 92, wherein e, f, and g are each 1, h is 6 and $PA_c$, $PA_j$ and $PA_n$ each have a molecular weight of about 2464.

95. A blend of a polymer and a compound of any of paragraphs 1 through 94.

96. The blend of paragraph 95, wherein the polymer is present in a range of about 1 to about 50 percent by weight.

97. The blend of paragraph 96, wherein the polymer is present in a range of about 1 to about 30 percent by weight.

98. A bioadhesive construct comprising:
a support suitable for tissue repair or reconstruction; and
a coating comprising any of the blends of paragraphs 95 through 97.

99. The bioadhesive construct of paragraph 98, further comprising an oxidant.

100. The bioadhesive construct of either of paragraphs 98 or 99, wherein the oxidant is formulated with the coating.

101. The bioadhesive construct of either of paragraphs 98 or 99, wherein the oxidant is applied to the coating.

102. The bioadhesive construct of any of paragraphs 98 through 101, wherein the support is a film, a mesh, a membrane, a nonwoven or a prosthetic.

103. A bioadhesive construct comprising:
a support suitable for tissue repair or reconstruction;
a first coating comprising a multihydroxyphenyl (DHPD) functionalized polymer (DHPp) of any of paragraphs 1 through 94 and a polymer; and
a second coating coated onto the first coating, wherein the second coating comprises a multihydroxyphenyl (DHPD) functionalized polymer (DHPp) of any of paragraphs 1 through 94.

104. A bioadhesive construct comprising:
a support suitable for tissue repair or reconstruction;
a first coating comprising a first multihydroxyphenyl (DHPD) functionalized polymer (DHPp) of any of paragraphs 1 through 94 and a first polymer; and
a second coating coated onto the first coating, wherein the second coating comprises a second multihydroxyphenyl (DHPD) functionalized polymer (DHPp) of any of paragraphs 1 through 94 and a second polymer, wherein the first and second polymer may be the same or different and wherein the first and second DHPp can be the same or different.

105. A bioadhesive construct comprising:
a support suitable for tissue repair or reconstruction;
a first coating comprising a first multihydroxyphenyl (DHPD) functionalized polymer (DHPp) of any of paragraphs 1 through 94; and
a second coating coated onto the first coating, wherein the second coating comprises a second multihydroxyphenyl (DHPD) functionalized polymer (DHPp) of any of paragraphs 1 through 94, wherein the first and second DHPp can be the same or different.

106. A method to reduce bacterial growth on a substrate surface, comprising the step of coating a multihydroxyphenyl (DHPD) functionalized polymer (DHPp) of any of paragraphs 1 through 94 onto the surface of the substrate.

The following examples are illustrative in nature and should not be considered limiting in any way.

EXAMPLES

Synthesis of Medhesive-063 (PEG20k-$(DH)_8$)

51 g of 8-Armed PEG-$NH_2$ (20,000 MW; 21 mmol —$NH_2$) was dissolved with 234 mL of chloroform and 116 mL of DMF. 6.0 g of DOHA (33 mmol), 4.4 g of HOBt (33 mmol), 12 g of HBTU (33 mmol), and 6.9 mL of triethylamine were added. The reaction mixture was stirred at room temperature for one hour and added to 2400 mL of diethyl ether. The precipitate was dissolved in 350 mL of 12 mM HCl and dialyzed (3,500 MWCO) with deionized $H_2O$ (acidified to pH 3.5 with concentrated HCl) for 24 hrs and lyophilized. Medhesive-058 PEG10k-$(DH)_6$, Medhesive-059 PEG15k-$(DH)_6$, and Medhesive-060 PEG20k-$(DH)_6$ were created using similar procedures using corresponding starting material PEGs (6-armed PEG-$NH_2$ 10,000 MW, 6-armed PEG-$NH_2$ 15,000 MW, and 6-armed PEG-$NH_2$ 10,000 MW, respectively). Both $^1H$ NMR and UV-vis were used to quantify the amount of PEG-bound catechol.

PEG20k-$(DH)_8$ [Medhesive-063] L/N's 001479, 001490 and 002216. $^1H$ NMR (400 MHz, D2O): δ 6.84-6.67 (m, 3H, $C_6H_3(OH)_2$—), 3.94-3.60 (m, PEO), 3.52 (s, 2H, PEG-$CH_2$—CH(PEG)-), 3.28 (m, 2H, PEG-$CH_2$—NH—C(O)—), 2.94 (s, 1H, PEG-$CH_2$—CH(PEG)-), 2.80 (m, 2H, PEG-$CH_2$—NH—C(O)—$CH_2$—$CH_2$—), 2.50 (m, 2H, PEG-$CH_2$—NH—C(O)—$CH_2$—$CH_2$—). UV-vis spectroscopy: 0.374±0.028 μmole DH/mg polymer (6.80±0.52 wt % DH).

PEG10k-$(DH)_6$ [Medhesive-058] $^1H$ NMR (400 MHz, DMSO/TMS): δ 8.68 (d, 2H, $C_6H_3(OH)_2$—), 7.84 (m, 1H, PEG-$CH_2$—NH—C(O)—), 6.64-6.40 (m, 3H, $C_6H_3(OH)_2$—), 3.68-3.34 (m, PEO), 3.18 (m, 2H, PEG-$CH_2$—NH—C(O)—), 2.75-2.60 (m, 2H, PEG-$CH_2$—NH—C(O)—$CH_2$—$CH_2$—), 2.28-2.24 (m, 2H, PEG-$CH_2$—NH—C(O)—$CH_2$—$CH_2$—). UV-vis spectroscopy: 0.682±0.092 μmole DH/mg polymer (12.43±1.67 wt % DH).

PEG15k-$(DH)_6$ [Medhesive-059] $^1H$ NMR (400 MHz, DMSO/TMS): δ 8.80-8.60 (d, 2H, $C_6H_3(OH)_2$—), 7.84 (m, 1H, PEG-$CH_2$—NH—C(O)—), 6.64-6.40 (m, 3H, $C_6H_3(OH)_2$—), 3.69-3.3 (m, PEO), 3.19 (m, 2H, PEG-$CH_2$—

NH—C(O)—), 2.62-2.58 (m, 2H, PEG-CH$_2$—NH—C(O)—CH$_2$—CH$_2$—), 2.28-2.26 (m, 2H, PEG-CH$_2$—NH—C(O)—CH$_2$—CH$_2$—). UV-vis spectroscopy: 0.483±0.065 μmole DH/mg polymer (8.80±1.18 wt % DH).

PEG20k-(DH)$_6$ [Medhesive-060] $^1$H NMR (400 MHz, DMSO/TMS): δ 8.69-8.59 (d, 2H, C$_6$H$_3$(OH)$_2$—), 7.90 (m, 1H, PEG-CH$_2$—NH—C(O)—), 6.60-6.42 (m, 3H, C$_6$H$_3$(OH)$_2$—), 3.69-3.35, (m, PEO), 3.19 (m, 2H, PEG-CH$_2$—NH—C(O)—), 2.60-2.58 (m, 2H, PEG-CH$_2$—NH—C(O)—CH$_2$—CH$_2$—), 2.28-2.24 (m, 2H, PEG-CH$_2$—NH—C(O)—CH$_2$—CH$_2$—). UV-vis spectroscopy: 0.338±0.055 μmole DH/mg polymer (6.16±1.00 wt % DH).

Synthesis of Medhesive-061 (PEG20k-(DMu)$_8$)

Dry 50 g of 8-armed PEG-OH (20,000 MW; 20 mmol —OH) via azeotropic evaporation of toluene, followed by drying in a vacuum dessicator. Redissolve PEG in 400 mL toluene, then add 53 mL of phosgene solution (20% phosgene in toluene; 100 mmol phosgene). Stir the mixture at 55° C. for 4 hours with a NaOH solution trap to trap escaped phosgene. Evaporate toluene and dry with vacuum for overnight. Add 350 mL of chloroform and 3.46 g of N-hydroxysuccinimide (30 mmol) to the phosgene-activated PEG, followed by the addition of 4.18 mL (30 mmol) of triethylamine in 30 mL chloroform dropwise. Stir the mixture under Argon for 4 hours. To the reaction mixture, add 7.58 g dopamine-HCl (40 mmol), 11.16 mL triethylamine (80 mmol) and 120 mL DMF, then stir the reaction at room temperature for overnight. Add the reaction mixture to diethyl ether, then collect the precipitate via filtration and dry. The crude product will then be purified further using dialysis (3500 MWCO) in deionized water (acidified to pH 3.5) for 24 hours. Medhesive-082 (PEG40k-(DH)$_8$) was created using similar procedures using an 8-armed PEG-NH$_2$ 40,000 MW. After lyophilization, both $^1$H NMR and UV-vis will be used to determine the coupling efficiency of the catechol to PEG.

PEG20k-(DMu)8 [Medhesive-061 ]$_1$H NMR (400 MHz, DMSO/TMS): δ 8.73-8.63 (d, 2H, C$_6$H$_3$(OH)$_2$—), 7.2 (m, 1H, PEG-C(O)—NH—), 6.62-6.42 (m, 3H, C$_6$H$_3$(OH)$_2$—), 4.04-4.02 (s, 2H, PEG-CH$_2$—O—C(O)—NH—), 3.68 (m, 2H, C$_6$H$_3$(OH)$_2$—CH$_2$—CH$_2$—NH—C(O)—O—), 3.62-3.41 (m, PEG), 3.07 (m, 2H, C$_6$H$_3$(OH)$_2$—CH$_2$—CH$_2$—NH—C(O)—O—). UV-vis spectroscopy: 0.375±0.01 μmole DM/mg polymer (6.84±0.18 wt % DM).

EG40k-(DMu)$_8$ [Medhesive-082] $^1$H NMR (400 MHz DMSO/TMS): δ 8.76-8.63 (d, 2H, C$_6$H$_3$(OH)$_2$—), 7.2 (m, 1H, PEG-C(O)—NH—), 6.62-6.48 (m, 3H, C$_6$H$_3$(OH)$_2$—), 4.03-4.01 (s, 2H, PEG-CH$_2$—O—C(O)—NH—), 3.69-3.67 (m, 2H, C$_6$H$_3$(OH)$_2$—CH$_2$—CH$_2$—NH—C(O)—O—), 3.62-3.41 (m, PEG), 3.1 ((m, 2H, C$_6$H$_3$(OH)$_2$—CH$_2$—CH$_2$—NH—C(O)—O). UV-vis spectroscopy: 0.179±0.01 μmole DM/mg polymer (2.73±0.17 wt % DM).

Synthesis of Medhesive-068 (PEG20k-(SADMe)$_8$)

Added 10 g of 8-armed PEG-OH (20,000 MW; 4 mmol —OH), to 2 g of succinic anhydride (20 mmol), 100 mL chloroform and 1.6 mL of pyridine taken in a round bottom flask equipped with a condensation column. Refluxed the mixture at 80° C. in an oil bath with Ar purging overnight. The polymer solution was cooled to room temperature, added 100 mL of chloroform. The reaction mixture was washed successively with 100 mL each of 12 mM HCl, saturated NaCl solution, and H$_2$O. The organic layer is then dried over MgSO$_4$ and filtered. Reduced the filtrate to around 100 mL and added to 900 mL of diethyl ether. Collected the precipitate via filtration and dried the precipitate. Dissolved the dried precipitate further with 80 mL of chloroform and 40 mL of DMF. Added 1.1 g of dopamine-HCl (5.8 mmol), 2.07 g of HBTU (5.45 mmol), 375 mg of HOBt (2.77 mmol), and 1.0 mL of triethylamine (7.18 mmol) to the mixture and stirred for 1 hr. The mixture was added to 800 mL of diethyl ether. The precipitate was collected via vacuum filtration and dried. The crude product was further purified through dialysis (3500 MWCO) in deionized H$_2$O (acidified to pH 3.5) for 24 hrs. After lyophilization, 5.77 g of Medhesive-068 was obtained. $^1$H NMR (400 MHz, D$_2$O): δ 6.85-6.70 (m, 3H, C$_6$H$_3$(OH)$_2$—), 4.28 (s, 2H, PEG-CH$_2$—O—C(O)—NH—), 3.73-3.63 (m, PEG), 3.38 (t, 2H, C$_6$H$_3$(OH)$_2$—CH$_2$—CH$_2$—NH—C(O)—), 2.68 (t, 2H, C$_6$H$_3$(OH)$_2$—CH$_2$—CH$_2$—NH—C(O)—CH$_2$—CH$_2$—C(O)—O—), 2.63 (t, 2H, C$_6$H$_3$(OH)$_2$—CH$_2$—CH$_2$—NH—C(O)—CH$_2$—CH$_2$—C(O)—O—), 2.49 (t, 2H, C$_6$H$_3$(OH)$_2$—CH$_2$—CH$_2$—NH—C(O)—). UV-vis spectroscopy: 0.395±0.012 μmole DM/mg polymer (5.97±0.18 wt % DM).

Synthesis of Medhesive-069 (PEG20k-(GADMe)$_8$)

Added 10 g of 8-armed PEG-OH (20,000 MW; 4 mmol —OH), to 2.28 g of glutaric anhydride (20 mmol), 100 mL chloroform and 1.6 mL of pyridine taken in a round bottom flask equipped with a condensation column. Refluxed the mixture at 80° C. in an oil bath with Ar purging overnight. The polymer solution was cooled to room temperature, added 100 mL of chloroform. The reaction mixture was washed successively with 100 mL each of 12 mM HCl, saturated NaCl solution, and H$_2$O. The organic layer is then dried over MgSO$_4$ and filtered. Reduced the filtrate to around 100 mL and added to 900 mL of diethyl ether. Collected the precipitate via filtration and dried the precipitate. Dissolved the dried precipitate further with 80 mL of chloroform and 40 mL of DMF. Added 1.6 g of dopamine-HCl (8.62 mmol), 3.2 g of HBTU (8.62 mmol), 582 mg of HOBt (4.31 mmol), and 1.4 mL of triethylamine (10.34 mmol) to the mixture and stirred for 1 hr. The mixture was added to 900 mL of diethyl ether. The precipitate was collected via vacuum filtration and dried. The crude product was further purified through dialysis (3500 MWCO) in deionized H$_2$O (acidified to pH 3.5) for 24 hrs. After lyophilization, 5.65 g of Medhesive-069 was obtained. $^1$H NMR (400 MHz, D$_2$O): δ 6.85-6.70 (m, 3H, C$_6$H$_3$(OH)$_2$—), 4.28 (s, 2H, PEG-CH$_2$—O—C(O)—NH—), 3.73-3.63 (m, PEG), 3.38 (t, 2H, C$_6$H$_3$(OH)$_2$—CH$_2$—CH$_2$—NH—C(O)—), 2.68 (t, 2H, C$_6$H$_3$(OH)$_2$—CH$_2$—CH$_2$—NH—C(O)—CH$_2$—CH$_2$—CH$_2$—C(O)—O—), 2.53 (t, 2H, C$_6$H$_3$(OH)$_2$—CH$_2$—CH$_2$—NH—C(O)—CH$_2$—CH$_2$—CH$_2$—C(O)—O—), 2.43 (t, 2H, C$_6$H$_3$(OH)$_2$—CH$_2$—CH$_2$—NH—C(O)—CH$_2$—CH$_2$—CH$_2$—C(O)—O—), 1.82 (t, 2H, C$_6$H$_3$(OH)$_2$—CH$_2$—CH$_2$—NH—C(O)—). UV-vis spectroscopy: 0.211±0.019 μmole DM/mg polymer (3.48±0.32 wt % DM).

Synthesis of Medhesive-072 (PEG20k-(DMUrea)$_8$)

Dried 10 g of 8-arm PEG-NH$_2$ (20,000 MW; 4 mmol —OH) via azeotropic evaporation of toluene, and further dried under vacuum. Redissolved PEG in 100 mL toluene, followed by addition of 10.6 ml, of phosgene solution (20% phosgene in toluene; 20 mmole phosgene). The reaction mixture was stirred at 55° C. for 4 hours under Argon with a NaOH trap to catch any escaped phosgene. Toluene was removed via rotary evaporation, and the PEG dried with vacuum for 18 hours. Next 65 mL chloroform and 691 mg N-Hydroxysuccinimide (6 mmole) were added to the phosgene-activated PEG, followed by dropwise addition of 840 μL (6 mmole) of triethylamine in 10 mL chloroform. Stirred the reaction under Argon for 4 hours. Added 1.52 g of dopamine-HCl (8 mmole) dissolved in 25 mL DMF and 2.24 mL (16 mmole) triethylamine to the reaction mixture and stirred at room temperature overnight. The reaction mixture was added to 700 mL of diethyl ether, the precipitate was collected via vacuum filtration and dried under vacuum. The crude product was further purified using dialysis (3500 MWCO) in deionized water (acidified to pH 3.5) for 48 hours. After lyophilization 8.86 g of Medhesive-072 was obtained. $^1$H NMR (400 MHz DMSO/TMS): δ 8.76-8.58 (d, 2H, $C_6H_3(OH)_2$—), 6.63-6.36 (m, 3H, $C_6H_3(OH)_2$—), 5.91-5.85 (d, 2H, PEG-$CH_2$—$CH_2$—NH—C(O)—NH—), 3.83-3.70 (m, 2H, PEG-$CH_2$—O—$(CH_2)_2$—NH—), 3.64-3.36 (m, PEG), 3.16-3.12 (m, 4H, —$CH_2$—$CH_2$—NH—C(O)—NH—$CH_2$—$CH_2$—). UV-vis spectroscopy: 0.313±0.006 μmole DM/mg polymer (4.77±0.09 wt % DM).

Synthesis of Medhesive-074 (PEG15k-(DMUrea)$_6$)

Dried 10 g of 6-arm PEG-NH$_2$ (15,000 MW; 4 mmol —OH) via azeotropic evaporation of toluene, and further dried under vacuum. Redissolved PEG in 100 mL toluene, followed by addition of 10.6 ml, of phosgene solution (20% phosgene in toluene; 20 mmole phosgene). The reaction mixture was stirred at 55° C. for 4 hours under Argon with a NaOH trap to catch any escaped phosgene. Toluene was removed via rotary evaporation, and the PEG dried with vacuum for 18 hours. Next 65 mL chloroform and 691 mg N-Hydroxysuccinimide (6 mmole) were added to the phosgene-activated PEG, followed by dropwise addition of 840 μL (6 mmole) of triethylamine in 10 mL chloroform. Stirred the reaction under Argon for 4 hours. Added 1.52 g of dopamine-HCl (8 mmole) dissolved in 25 mL DMF and 2.24 mL (16 mmole) triethylamine to the reaction mixture and stirred at room temperature overnight. Added to diethyl ether, the precipitate was collected via vacuum filtration and dried under vacuum. The crude product was further purified using dialysis (3500 MWCO) in deionized water (acidified to pH 3.5) for 48 hours. After lyophilization 8.45 g of Medhesive-074 was obtained. $^1$H NMR (400 MHz DMSO/TMS): δ 8.76-8.62 (d, 2H, $C_6H_3(OH)_2$—), 6.62-6.40 (m, 3H, $C_6H_3(OH)_2$—), 5.92-5.87 (d, 2H, PEG-$CH_2$—$CH_2$—NH—C(O)—NH—), 3.63-3.60 (m, 2H, PEG-$CH_2$—O—$(CH_2)_2$—NH—), 3.59-3.36 (m, PEG), 3.22-3.19 (m, 4H, —$CH_2$—$CH_2$—NH—C(O)—NH—$CH_2$—$CH_2$—). UV-vis spectroscopy: 0.380±0.020 μmole DM/mg polymer (5.78±0.31 wt % DM).

Synthesis of Medhesive-075 (PEG20k-(BA)$_8$)

5 g of 8-Armed PEG-NH$_2$ (20,000 MW; 1.25 mmol —NH$_2$) was dissolved with 37.5 mL of chloroform and 22.5 mL of DMF. 715 mg of diacetyl-3,4-dihydroxybenzoic acid (3 mmol), 405 mg of HOBt (3 mmol), 1.14 g of HBTU (3 mmol), and 0.627 mL of triethylamine were added. The reaction mixture was stirred at room temperature for 5 hours and added to 400 mL of diethyl ether. The precipitate was dried with vacuum. 2.5 g of the diacetyl protected polymer was dissolved in 20 mL of anhydrous DMF and bubbled with Ar for 10 min. 1.16 mL of piperidine was added and the mixture was stirred at room temperature with Ar bubbling for 15 min. The solution was quickly added to an excess of diethyl ether, and collected precipitate was dried and dialyzed (3,500 MWCO) with deionized H$_2$O (acidified to pH 3.5 with concentrated HCl) for 24 hrs and lyophilized to yield 1.22 g of Medhesive-075. $^1$H NMR (400 MHz, DMSO): δ 9.41 (s, 1H, $C_6H_3(OH)(OH)$—), 9.07 (s, 1H, $C_6H_3(OH)(OH)$—), 8.12 (m, 1H, PEG-$CH_2$—NH—C(O)—), 7.26-6.71 (m, 3H, $C_6H_3(OH)_2$—), 3.17-3.70 (m, PEO). UV-vis spectroscopy: 0.253±0.0023 μmole BA/mg polymer (3.44±0.030 wt % BA).

Synthesis of 3,4-diacetyloxybenzoic acid (Medhesive-076 Starting Material)

Added 20 g of 3,4-dihydroxybenzoic acid (0.13 mmole) with 100 mL of acetic anhydride (1.06 mole) and 100 mL of pyridine (1.24 mmole) in a round bottom flask (500 mL). The reaction was stirred at room temperature for 1 hour. After one hour the reaction was poured into 100 mL of water and acidified to a pH ~2 using concentrated hydrochloric acid. The solution was allowed to cool to room temperature and was extracted 3 times using a total of 500 mL ethyl acetate. The solution was then dried over magnesium sulfate for 24 hours and filtered. The solvent was then rotary evaporated off to give a white solid. This solid was then recrystallized in 150 mL of ethyl acetate. The precipitate was then collected through suction filtration and dried under vacuum.

3,4-diacetyloxybenzoic acid L/N 003119. $^1$H NMR (400 MHz, DMSO/TMS): δ 13.2 (s, 1H, $HOOCC_6H_3(OCOCH_3)_2$—), 7.89 (dd, 1H, $HOOCC_6H_3(OCOCH_3)_2$—) 7.81 (s, 1H, $HOOCC_6H_3(OCOCH_3)_2$—), 7.4 (s, 1H, $HOOCC_6H_3(OCOCH_3)_2$—) 2.28 (d, 6H, $HOOCC_6H_3(OCOCH_3)_2$—).

Synthesis of Medhesive-076 (LN003127)

Dissolve 5 grams of 8-arm PEG-OH-20k (0.25 mmole) and 0.72 grams (3 mmole) of 3,4-diacetyloxybenzoic acid in a round bottom flask with 7.5 mL anhydrous DMF and 47.5 mL of chloroform and place under argon. Add 0.62 grams (3 mmole) of DCC to reaction along with 11 mg (0.3 mmole) of DMAP and place reaction in a cool water bath. Allow reaction to proceed for 24 hours. Take out and filter reaction into diethyl ether and place at 4° C. for 24 hours. Suction filter precipitate and dry in a vacuum pump for 24 hours and run a TLC plate to verify there is coupling as well as $^1$H NMR to determine the coupling efficiency.

Dissolve 2.5 grams (0.125 mmole) in 20 mL of anhydrous DMF. The solution was bubbled with argon for 30 minutes. To the solution was added 1.16 mL of piperidine. The reaction was continued for 25 minutes with argon bubbling through the solution and then added to 350 mL of diethyl ether. The solution was placed at 4° C. overnight with the precipitate being vacuum filtered and dried for 24 hours. The solution was then dissolved in 50 mL of 12.1 mM HCl. This was then filtered using coarse filter paper and dialyzed (3500 MWCO) in 4 L of water at pH 3.5 for 24 hours with changing of the water at least 4 times a day. The solution was then freeze dried and placed under a vacuum for 4-24 hours. After drying, $^1$H NMR, UV-VIS, were used to determine purity and coupling efficiency of the catechol.

PEG20k-(BAe)$_8$ [Medhesive-076] L/N's 003127. $^1$H NMR (400 MHz, DMSO/TMS): δ 9.76 (s, 1H, $C_6H_3(OH)_2$—), 9.36 (s, 1H, $C_6H_3(OH)_2$—), 7.35 (dd, 2H, $C_6H_3(OH)_2$—), 6.8 (dd, 1H, $C_6H_3(OH)_2$—), 4.2 (t, 2H, —$CH_2OCOC_6H_3(OH)_2$) 3.6 (m, 226H, O—$CH_2CH_2$—O). UV-vis spectroscopy: 0.037±0.003 μmole DH/mg polymer (0.51±0.04 wt % BA). Coupling Efficiency by; UV-vis=8.8% $^1$H NMR=10%.

Synthesis of Medhesive-079 (LN003127)

Dissolve 5 grams of 8-arm PEG-NH2-20 k (0.25 mmole) and 0.721 grams (3 mmole) of caffeic acid in a round bottom flask with 12.5 mL anhydrous DMF and 37.5 mL of chloroform. Add 0.541 grams (4 mmole) of HOBt to reaction along with 1.517 g (4 mmole) of HBTU and 0.56 mL of triethylamine (4 mmole). Let the reaction proceed for 1 hour then gravity filter reaction into diethyl ether and place at 4° C. for 24 hours. Suction filter precipitate and dry in a vacuum pump for 24 hours. The solution was then dissolved in 100 mL of 12.1 mM HCl. This was then filtered using coarse filter paper and dialyzed (3500 MWCO) in 4 L of water at pH 3.5 for 24 hours with changing of the water at least 4 times a day. The solution was then freeze dried and placed under a vacuum for 4-24 hours. After drying, $^1$H NMR and UV-VIS were used to determine purity and coupling efficiency of the catechol.

PEG20k-(CA)$_8$ [Medhesive-079] L/N's 003122. $^1$H NMR (400 MHz, DMSO/TMS): δ 9.4 (s, 1H, $C_6H_3(OH)_2$—), 9.2 (s, 1H, $C_6H_3(OH)_2$—), 8.1 (s, 1H, $NHCOCHCHC_6H_3(OH)_2$—), 7.2 (dd, 1H, $C_6H_3(OH)_2$—), 6.9 (s, 1H, $C_6H_3(OH)_2$—), 6.7 (d, 2H, —$NHCOCHCHC_6H_3(OH)_2$), 6.3 (dd, 1H, —$NHCOCHCHC_6H_3(OH)_2$), 3.6 (m, 226H, O—$CH_2CH_2$—O). UV-vis spectroscopy: 0.08±0.02 μmole DH/mg polymer (0.1.29±0.33 wt % CA). Coupling Efficiency by; UV-vis=21.2% $^1$H NMR=25%.

Synthesis of Medhesive-081 (PEG20k-(DOPA$_4$)$_8$)

4.2 g of 8-Armed PEG-NH$_2$ (20,000 MW; 1.66 mmol —NH$_2$) was dissolved with 45 mL of anhydrous THF. 2.56 g of diacetyl-DOPA N-carboxyanhydride (8.31 mmol) and 289 μL of diisopropylethylamine (1.66 mmol) were added. The mixture was stirred for 6 days at room temperature. Precipitated the polymer by adding to diethyl ether and the solid was collected and dried. The polymers was deprotected by dissolving in 60 mL of anhydrous DMF and 3.2 mL of piperidine was added. The solution was stirred with Ar bubbling for 15 min. The solution was quickly added to an excess of diethyl ether, and the collected precipitate was dried and dialyzed (3,500 MWCO) with deionized H$_2$O (acidified to pH 3.5 with concentrated HCl) for 24 hrs and lyophilized to yield 3.5 g of Medhesive-081. $^1$H NMR (400 MHz, DMSO): δ 7.26-6.71 (m, 3H, C$_6$H$_3$(OH)$_2$—), 4.80 (br, 1H, —C(O)—CH (NH—)—CH$_2$—), 3.80-3.35 (m, PEO), 2.90-2.65 (m, 2H, —C(O)—CH(NH—)—CH$_2$—). UV-vis spectroscopy: 1.36±0.050 μmole DOPA/mg polymer (24.4±0.90 wt % DOPA).

Synthesis of Medhesive-086 (dpe-PEG15k-(DH)$_6$)

10 g of dpe-6-Arm PEG-NH$_2$ (15,000 MW; 4.0 mmol —NH$_2$) was dissolved with 44 mL of chloroform and 22 mL of DMF. 1.09 g of DOHA (6.0 mmol), 0.81 g of HOBt (6.0 mmol), 2.27 g of HBTU (6.0 mmol), and 0.84 mL of triethylamine were added. The reaction mixture was stirred at room temperature for one hour and added to 400 mL of diethyl ether. The precipitate was dissolved in 100 mL of 12 mM HCl and dialyzed (3,500 MWCO) with deionized H$_2$O (acidified to pH 3.5 with concentrated HCl) for 24 hrs and lyophilized to yield 6.7 g of Medhesive-086. $^1$H NMR (400 MHz, DMSO): δ 7.84 (d, 2H, C$_6$H$_3$(OH)$_2$—), 6.64-6.40 (m, 3H, C$_6$H$_3$(OH)$_2$—), 3.68-3.17 (m, PEO), 2.98 (m, 2H, PEG-CH$_2$—NH—C(O)—), 2.60 (t, 2H, PEG-CH$_2$—NH—C(O)—CH$_2$—CH$_2$—), 2.26 (t, 2H, PEG-CH$_2$—NH—C(O)—CH$_2$—CH$_2$—). UV-vis spectroscopy: 0.32±0.0053 μmole DH/mg polymer (5.2±0.086 wt % DH).

Synthesis of Medhesive-087 (PEG20k-(LyseDH$_2$)$_8$)

Combined 150.9 g of 8-arm PEG-OH and 300 mL of toluene in a 1 L round bottom flask equipped with a Dean-Stark apparatus, condensation column, and an Argon inlet. The mixture was stirred in a 160-165° C. oil bath until about ¾ of toluene was evaporated and collected with Argon purging. The reaction mixture was allowed to cool to room temperature and 675 mL of chloroform was added. 62.4 g of N,N'-α,ε-Bis-Boc-Lysine, 37.2 g of N,N'-dicyclohexylcarbodiimide, and 729 mg of 4-(Dimethylamino) pyridine were added and the reaction mixture was stirred in a room temperature water bath for overnight with Argon purging. Filtered the insoluble urea byproduct with coarse filter paper through vacuum filtration and filtrate was added to 3.75 L of diethyl ether for overnight at 4° C. After collecting and drying the precipitate, 159.61 g of PEG20k-(Boc$_2$Lyse)$_8$ was obtained. The polymer was dissolved in 319 mL of chloroform and 319 mL of TFA was slowly added. The mixture was stirred at room temperature for 30 min and added to 3.2 mL of diethyl ether. The mixture was placed in −20° C. for overnight and the supernatant was decanted. The gooey solid was precipitated again in chloroform/ether mixture and dried with vacuum pump. The solid was then dissolved in 2 L of deionized water and dialyzed with 3500 MWCO dialysis tubes for two hours in 20 L of deionized water followed by 40 hrs in 20 L of water acidified to pH 3.5 with HCl, and 2 hrs in deionized water. After lyophilization, 83.35 g of PEG20k-(Lyse)$_8$ was obtained. The polymer was further dissolved with 550 mL of chloroform and 275 mL of DMF and 22.42 g of DOHA, 16.67 g of HOBt, 46.76 g of HBTU, and 17.25 mL of triethylamine was added. The reaction mixture was stirred at room temperature for 1.5 hr and then added to 4.2 L of diethyl ether. The precipitate was collected with vacuum filtration and further purified with dialysis (3500 MWCO tubes in pH 3.5 water for 24 hrs and unbuffered water for 20 hrs and then freeze dried. 64.5 g of PEG20k-(LyseDH)$_8$ was obtained (L/N 004433). $^1$H NMR (400 MHz, D$_2$O): δ 6.80-6.50 (m, 6H, O—C(O)—CH$_2$—CH$_2$—C$_6$H$_3$(OH)$_2$), 4.2 (s, 2H, C(O)—CHCH$_2$CH$_2$—NH—), 3.8-3.43 (m, PEG, CH$_2$—CH$_2$—O), 1.8-0.8 (m, 6H, Lys CH$_2$—CH$_2$—CH$_2$—). UV-vis spectroscopy: 0.597±0.032 μmole DH/mg polymer (9.85±0.53 wt % DH).

Synthesis of Medhesive-089 (PEG20k-(DMuDH2e)$_8$)

Dissolved 6.44 g Medhesive-061 (4.77 mmole —OH) in 30 mL chloroform and 20 mL DMF while Ar purging. Added 3.81 g of Diacetyl DOHA (14.3 mmole), 2.95 g dicyclohexylcarbodiimide (DCC, 14.3 mmole) and 58.3 mg 4-(Dimethylamino)pyridine (DMAP, 0.477 mmole) to the reaction. The reaction mixture was sealed under Argon and stirred at room temperature for 20 hours. Insoluble salts were then filtered and washed. Chloroform was removed via rotary evaporation, and the mixture was added to excess diethyl ether. The precipitate was collected with vacuum filtration and dried under vacuum to yield 7 g of diacetyl protected polymer. $^1$H NMR confirmed over 100% coupling of diacetyl DOHA. 3.5 g of the protected polymer was dissolved in 22.5 mL of anhydrous DMF and bubbled with Ar for 10 min. 1.18 mL of piperidine was added and the mixture was stirred at room temperature with Ar bubbling. The solution was quickly added to an excess of diethyl ether, and the collected precipitate was reprecipitate in chloroform/ethyl ether. After drying, 2.7 g of Medhesive-089 was obtained. $^1$H NMR (400 MHz, DMSO): δ 8.73-8.63 (br, 2H, C$_6$H$_3$(OH)$_2$—), 7.2 (m, 1H, PEG-C(O)—NH—), 6.81-6.39 (m, 9H, C$_6$H$_3$(O—C(=O)—CH$_2$—CH$_2$—C$_6$H$_3$(OH)$_2$)$_2$—), 4.04-4.02 (s, 2H, PEG-CH$_2$—O—C(O)—NH—), 3.69-3.32 (m, PEG), 3.09-2.49 (m, 12H, C$_6$H$_3$(O—C(=O)—CH$_2$—CH$_2$—)$_2$—CH$_2$—CH$_2$—NH—C(O)—O—).

Mixing 30 μL of 300 mg/mL of Medhesive-089 (in PBS 2×) with equal volume of 9.6 mg/mL of NaIO$_4$ (44.9 μLmol/mL) resulted in a solid hydrogel (15 wt % polymer, [$^-$IO$_4$]: [DOHA]~0.25) in 7-9 seconds. When the hydrogel was submerged in 1N NaOH solution, the hydrogel completely dissolved in 21 minutes. This indicates that Medhesive-089 can be rapidly cured while still capable of undergoing degradation through hydrolysis of ester linkages.

Synthesis of Medhesive-091 (PEG20K-(DH)$_8$)

Dissolved PEG20K (10 g, 0.5 mmol), Diacetylated DOHA (1331.25 mg, 4.8 mmol) and DMAP (17.60 mg, 0.144 mmol) in 75 mL of Chloroform in ice water bath. DCC (1089.5 mg, 5.28 mmol) was added and allowed to stir overnight at room temperature. Filtered the solution into 600 mL of diethyl ether. Collected the precipitate via filtration and dried the precipitate. Dissolved the dried precipitate in 100 ml of anhydrous DMF with argon purging for 10 minutes. Added 5 ml of piperidine and stirred with argon purging for 15 minutes. Filtered into 800 ml of diethyl ether. The precipitate was collected via vacuum filtration and dried. The crude product was further purified through dialysis (3500 MWCO) in deionized H$_2$O (acidified to pH 3.5) for 48 hrs. After lyophilization, 6.82 g of Medhesive-91 was obtained. $^1$H NMR (400 MHz, D$_2$O): δ 6.83-6.69 (m, 3H, C$_6$H$_3$(OH)$_2$—), 4.26 (s, 2H, PEG-CH$_2$—O—C(O)—), 3.79-3.48 (m, PEG), 2.83 (t, 2H, C$_6$H$_3$(OH)$_2$—CH$_2$—CH$_2$—C(O)—), 2.60 (t, 2H, C$_6$H$_3$(OH)$_2$—CH$_2$—CH$_2$—C(O)—), UV-vis spectroscopy: 0.0626±0.002 μmole DH/mg polymer (1.03±0.00038 wt % DH).

Synthesis of 3,4-diacetyloxybenzoic acid (Medhesive-076 Starting Material)

Added 20 g of 3,4-dihydroxybenzoic acid (0.13 mmole) with 100 mL of acetic anhydride (1.06 mole) and 100 mL of pyridine (1.24 mmole) in a round bottom flask (500 mL). The reaction was stirred at room temperature for 1 hour. After one hour the reaction was poured into 100 mL of water and acidified to a pH ~2 using concentrated hydrochloric acid. The solution was allowed to cool to room temperature and was extracted 3 times using a total of 500 mL ethyl acetate. The solution was then dried over magnesium sulfate for 24 hours and filtered. The solvent was then rotary evaporated off to give a white solid. This solid was then recrystallized in 150 mL of ethyl acetate. The precipitate was then collected through suction filtration and dried under vacuum.

3,4-diacetyloxybenzoic acid L/N 003119. $^1$H NMR (400 MHz, DMSO/TMS): δ 13.2 (s, 1H, $HOOCC_6H_3(OCOCH_3)_2$—), 7.89 (dd, 1H, $HOOCC_6H_3(OCOCH_3)_2$—) 7.81 (s, 1H, $HOOCC_6H_3(OCOCH_3)_2$—), 7.4 (s, 1H, $HOOCC_6H_3(OCOCH_3)_2$—) 2.28 (d, 6H, $HOOCC_6H_3(OCOCH_3)_2$—).

Synthesis of Medhesive-092 (LN003125)

Add 1.67 g (7 mmol) of 3,4-diacetyloxybenzoic acid along with 1.61 g (7 mmole) of NHS and 1.45 g (14 mmol) of DCC in 7 mL chloroform and 16.7 mL of anhydrous DMF. Allow reaction to stir in a water bath for 24 hours. Filter and place in a 100 mL round bottom flask and dissolve 6-arm PEG-NH2-15 k (0.33 mmole). Add 25 mL of chloroform to reaction so completely dissolves mixture. Add 280 μL of triethylamine and let react for 24 hours. Gravity filter reaction into 350 ml, of diethyl ether and place at 4° C. for 24 hours. Suction filter precipitate and dry in a vacuum pump for 24 hours.

Dissolve 5 grams (0.25 mmole) in 40 mL of anhydrous DMF. The solution was bubbled with argon for 30 minutes. To the solution was added 2.32 mL of piperidine. The reaction was continued for 15 minutes with argon bubbling through the solution and then added to 350 mL of diethyl ether. The solution was placed at 4° C. overnight with the precipitate being vacuum filtered and dried for 24 hours. The solution was then dissolved in 100 mL of 12.1 mM HCl. This was then filtered using coarse filter paper and dialyzed (3500 MWCO) in 4 L of water at pH 3.5 for 24 hours with changing of the water at least 4 times a day. The solution was then freeze dried and placed under a vacuum for 4-24 hours. After drying, $^1$H NMR and UV-VIS were used to determine purity and coupling efficiency of the catechol.

PEG15k-$(BA)_6$ [Medhesive-092] L/N's 003125. $^1$H NMR (400 MHz, DMSO/TMS): δ 9.4 (s, 1H, $C_6H_3(OH)_2$—), 9.2 (s, 1H, $C_6H_3(OH)_2$—), 8.1 (s, 1H, $NHCOCHCHC_6H_3(OH)_2$—), 7.2 (dd, 1H, $C_6H_3(OH)_2$—), 6.9 (s, 1H, $C_6H_3(OH)_2$—), 6.7 (d, 2H, —$NHCOCHCHC_6H_3(OH)_2$), 6.3 (dd, 1H, —$NHCOCHCHC_6H_3(OH)_2$), 3.6 (m, 226H, O—$CH_2CH_2$—O). UV-vis spectroscopy: 0.029±0.007 μmole DH/mg polymer (0.4±0.1 wt % BA). Coupling Efficiency by; UV-vis=6.97% $^1$H NMR=2.9%.

Synthesis of 2,3,4-triacetyloxybenzoic acid (Medhesive-093 Starting Material)

Added 5 g of 2,3,4-trihydroxybenzoic acid (2.94 mmole) with 37.5 mL of acetic anhydride (39.8 mmole) and 37.5 mL of pyridine (46.5 mmole) in a round bottom flask (250 mL). The reaction was stirred at room temperature for 48 hour. Reaction was poured into 500 mL of water and acidified to a pH ~2 using concentrated hydrochloric acid. The solution was allowed to cool to room temperature and was extracted 3 times using a total of 500 mL ethyl acetate. The solution was then dried over magnesium sulfate for 24 hours and filtered. The solvent was then rotary evaporated off to give a white solid. This solid was then recrystallized in 150 mL of ethyl acetate. The precipitate was then collected through suction filtration and dried under vacuum. The product was then added to 200 mL of nanopure water and sonicated for 3 hours. The product (2.41 g) was taken and added to 25 mL (264 mmol) of acetic anhydride and 25 mL (309 mmol) of pyridine for 1 hour. Reaction was poured into 500 mL of water and acidified to a pH ~2 using concentrated hydrochloric acid. The solution was allowed to cool to room temperature and was extracted 3 times using a total of 500 mL ethyl acetate. The solution was then dried over magnesium sulfate for 24 hours and filtered. The solvent was then rotary evaporated off to give a white solid. This solid was then recrystallized in 150 mL of ethyl acetate. The precipitate was then collected through suction filtration and dried under vacuum. TLC was done to analyze the purity along with $^1$H NMR.

3,4-diacetyloxybenzoic acid L/N 003131. $^1$H NMR (400 MHz, DMSO/TMS): δ 13.3 (s, 1H, $HOOCC_6H_2(OCOCH_3)_2$—), 7.9 (s, 1H, $HOOCC_6H_2(OCOCH_3)_3$—) 7.3 (s, 1H, $HOOCC_6H_2(OCOCH_3)_3$—), 2.3 (d, 9H, $HOOCC_6H_2(OCOCH_3)_3$—).

Synthesis of Medhesive-093 (LN003141)

Dissolve 2.5 grams of 8-arm PEG-OH-20k (0.125 mmole) and 0.6 grams (2 mmole) of 3,4-diacetyloxybenzoic acid in a round bottom flask with 35 mL dioxane, 5 mL of THF and 15 mL 1,4-dioxane and place under argon. Add 0.413 grams (2 mmole) of DCC to reaction along with 24.4 mg (0.2 mmole) of DMAP and place reaction in a cool water bath. Allow reaction to proceed for 24 hours. Take out and filter reaction into diethyl ether and place at 4° C. for 24 hours. Suction filter precipitate and dry in a vacuum pump for 24 hours and run a TLC plate to verify there is coupling as well as $^1$H NMR to determine the coupling efficiency.

Dissolve 1.99 grams (0.1 mmole) in 20 mL of anhydrous DMF. The solution was bubbled with argon for 30 minutes. To the solution was added 1.16 mL of piperidine. The reaction was continued for 15 minutes with argon bubbling through the solution and then added to 350 mL of diethyl ether. The solution was placed at 4° C. overnight with the precipitate being vacuum filtered and dried for 24 hours. The solution was then dissolved in 50 mL of 12.1 mM HCl. This was then filtered using coarse filter paper and dialyzed (3500 MWCO) in 4 L of water at pH 3.5 for 24 hours with changing of the water at least 4 times a day. The solution was then freeze dried and placed under a vacuum for 4-24 hours. After drying, TLC and $^1$H NMR was used to determine purity and coupling efficiency of the catechol.

PEG20k-$(THBAe)_8$ [Medhesive-093] L/N's 003127. $^1$H NMR (400 MHz, DMSO/TMS): δ 10.6 (s, 1H, $C_6H_3(OH)_3$—), 9.9 (s, 1H, $C_6H_3(OH)_3$—), 8.6 (s, 1H, $C_6H_3(OH)_3$—), 7.2 (dd, 2H, $C_6H_3(OH)_3$—), 6.4 (dd, 1H, $C_6H_3(OH)_3$—), 4.4 (t, 2H, —$CH_2OCOC_6H_3(OH)_3$) 3.6 (m, 226H, O—$CH_2CH_2$—O). $^1$H NMR=13.8%.

Synthesis of Medhesive-094 (PEG20k-$(DOPA_3$-$Lys_3)_8$)

5 g of 8-Armed PEG-$NH_2$ (20,000 MW; 2 mmol —$NH_2$) was dissolved with 50 mL of anhydrous THF. 3.08 g of diacetyl-DOPA N-carboxyanhydride (10 mmol), 3.94 g of Fmoc-Lysine N-carboxyanhydride (10 mmol), and 348 μL of diisopropylethylamine (2 mmol) were added. The mixture was stirred for 5 days at room temperature. Precipitated the polymer by adding to diethyl ether and the solid was collected and dried. To yield diacetyl and Fmoc protected version of Medhesive-094. The polymers can be deprotected using a similar method as describe in the synthesis of Medhesive-081.

Synthesis of Medhesive-095 (PEG20k-(PLA-DMu)$_8$)

25 g of 8-armed PEG-OH (20,000 MW; 10 mmol —OH) was dried via azeotropic evaporation of toluene using rotary evaporation, followed by drying in a vacuum dessicator for overnight. PEG was dissolved in 200 mL of anhydrous THF and purged with Ar. 438 mg (11 mmol) of NaH (dispersed in mineral oil) was washed with 30 mL each of hexane 3 times under Ar. Add PEG solution to NaH and the mixture was stirred at room temperature for 4 hrs with Ar purging. Lactide (5.76 g 40 mmol) in 100 mL of anhydrous THF was added and the mixture was stirred under Ar for 24 hrs. 5.68 mL of glacial acetic acid was added to stop the polymerization and the mixture was precipitated in 800 mL of diethyl ether. After collecting the precipitate, the polymer was reprecipitated in chloroform/diethyl ether. The polymer was collected using vacuum filtration and the dried with vacuum. 23 g of the polymer was further dried via azeotropic evaporation of toluene using rotary evaporation, followed by drying in a vacuum dessicator for overnight. The polymer was dissolved 100 mL of phosgene solution (20% phosgene in toluene; 200 mmol phosgene) and the mixture was stirred under Ar at 55° C. for 4 hours with a NaOH solution trap to trap escaped phosgene. The solvent was evaporated and the polymer was dried with vacuum for overnight. 100 mL of chloroform and 2.31 g of N-hydroxysuccinimide (20 mmol) were added to the phosgene-activated PEG, followed by the addition of 2.46 mL (17.6 mmol) of triethylamine in 50 mL chloroform dropwise. The mixture was stirred under Argon for 4 hours and then 3.79 g of dopamine-HCl (20 mmol) in 25 mL of DMF and 2.8 mL triethylamine (20 mmol) were added and the mixture was stirred at room temperature for overnight. The reaction mixture was filtered into 800 mL of diethyl ether and placed in 4° C. for overnight. The precipitate was collected via vacuum filtration and dried in vacuum for 2 hrs. The crude product will then dissolved in 200 mL of 12 mM HCl and dialyzed for 2 days (3500 MWCO) in deionized water (acidified to pH 3.5). After lyophilization, 14.3 g of Medhesive-095 was obtained. $^1$H NMR (400 MHz, CDCl$_3$): δ 6.80-6.50 (m, 3H, C$_6$H$_3$(OH)$_2$—), 5.17 (m, 1H, —C(=O)CH(CH$_3$)—O—), 4.30 (s, 2H, PEG-CH$_2$—O—C(=O)—), 3.95-3.50 (m, PEG), 3.21 (t, 2H, C$_6$H$_3$(OH)$_2$—CH$_2$—CH$_2$—NH—C(O)—), 2.61 (t, 2H, C$_6$H$_3$(OH)$_2$—CH$_2$—CH$_2$—NH—C(O)—), 1.54 (m, 1H, —C(=O)CH(CH$_3$)—O—). UV-v is 0.23±0.016 μmol dopamine/mg polymer; 3.5±0.25 wt % dopamine; 68% coupling efficiency.

Synthesis of Medhesive-102 (PEG20k-(MGADMe)$_8$)

Added 10 g of 8-armed PEG-OH (20,000 MW; 4 mmol —OH), to 2.56 g of 3-Methyl glutaric anhydride (20 mmol), 100 mL chloroform and 1.6 mL of pyridine taken in a round bottom flask equipped with a condensation column. Refluxed the mixture at 80° C. in an oil bath with Ar purging overnight. The polymer solution was cooled to room temperature, added 100 mL of chloroform. The reaction mixture was washed successively with 100 mL each of 12 mM HCl, saturated NaCl solution, and H$_2$O. The organic layer is then dried over MgSO$_4$ and filtered. Reduced the filtrate to around 100 mL and added to 900 mL of diethyl ether. Collected the precipitate via filtration and dried the precipitate. Dissolved the dried precipitate further with 80 mL of chloroform and 40 mL of DMF. Added 1.16 g of dopamine-HCl (6.16 mmol), 2.33 g of HBTU (6.16 mmol), 416 mg of HOBt (3.08 mmol), and 1.03 mL of triethylamine (7.4 mmol) to the mixture and stirred for 1 hr. The mixture was added to 900 mL of diethyl ether. The precipitate was collected via vacuum filtration and dried. The crude product was further purified through dialysis (3500 MWCO) in deionized H$_2$O (acidified to pH 3.5) for 24 hrs. After lyophilization, 5.46 g of Medhesive-102 was obtained.

$^1$H NMR (400 MHz, D$_2$O): δ 6.83-6.69 (m, 3H, C$_6$H$_3$(OH)$_2$—), 4.26 (s, 2H, PEG-CH$_2$—O—C(O)—NH—), 3.79-3.48 (m, PEG), 3.36 (t, 2H, C$_6$H$_3$(OH)$_2$—CH$_2$—CH$_2$—NH—C(O)—), 2.65 (t, 2H, C$_6$H$_3$(OH)$_2$—CH$_2$—CH$_2$—NH—C(O)—), 2.18 (m, 5H, C$_6$H$_3$(OH)$_2$—CH$_2$—CH$_2$—NH—C(O)—CH$_2$—CH(CH$_3$)—CH$_2$—C(O)—O—), 0.86 (s, 3H, C$_6$H$_3$(OH)$_2$—CH$_2$—CH$_2$—NH—C(O)—CH$_2$—CH(CH$_3$)—CH$_2$—C(O)—O—), UV-vis spectroscopy: 0.254±0.011 μmole DH/mg polymer (3.86±0.00173 wt % DH).

Synthesis of Medhesive-103 (PEG20k-(DMGADMe)$_8$)

Added 10 g of 8-armed PEG-OH (20,000 MW; 4 mmol —OH), to 2.8 g of 2,2-Dimethyl glutaric anhydride (20 mmol), 100 mL chloroform and 1.6 mL of pyridine taken in a round bottom flask equipped with a condensation column. Refluxed the mixture at 80° C. in an oil bath with Ar purging overnight. The polymer solution was cooled to room temperature, added 100 mL of chloroform. The reaction mixture was washed successively with 100 mL each of 12 mM HCl, saturated NaCl solution, and H$_2$O. The organic layer is then dried over MgSO$_4$ and filtered. Reduced the filtrate to around 100 mL and added to 900 mL of diethyl ether. Collected the precipitate via filtration and dried the precipitate. Dissolved the dried precipitate further with 80 mL of chloroform and 40 mL of DMF. Added 1.16 g of dopamine-HCl (6.16 mmol), 2.33 g of HBTU (6.16 mmol), 416 mg of HOBt (3.08 mmol), and 1.03 mL of triethylamine (7.4 mmol) to the mixture and stirred for 1 hr. The mixture was added to 900 mL of diethyl ether. The precipitate was collected via vacuum filtration and dried. The crude product was further purified through dialysis (3500 MWCO) in deionized H$_2$O (acidified to pH 3.5) for 24 hrs. After lyophilization, 5.84 g of Medhesive-103 was obtained. $^1$H NMR (400 MHz, D$_2$O): δ 6.82-6.66 (m, 3H, C$_6$H$_3$(OH)$_2$—), 4.24 (s, 2H, PEG-CH$_2$—O—C(O)—NH—), 3.78-3.49 (m, PEG), 3.43 (t, 2H, C$_6$H$_3$(OH)$_2$—CH$_2$—CH$_2$—NH—C(O)—), 2.65 (t, 2H, C$_6$H$_3$(OH)$_2$—CH$_2$—CH$_2$—NH—C(O)—), 2.42 (t, 2H, C$_6$H$_3$(OH)$_2$—CH$_2$—CH$_2$—NH—C(O)—CH$_2$—CH$_2$—C(CH$_3$)$_2$—C(O)—O—), 1.87 (t, 2H, C$_6$H$_3$(OH)$_2$—CH$_2$—CH$_2$—NH—C(O)—CH$_2$—CH$_2$—C(CH$_3$)$_2$—C(O)—O—), 1.15 (s, 6H, C$_6$H$_3$(OH)$_2$—CH$_2$—CH$_2$—NH—C(O)—CH$_2$—CH$_2$—(CH$_3$)$_2$—C(O)—O—), UV-vis spectroscopy: 0.224±0.017 μmole DH/mg polymer (3.41±0.0026 wt % DH).

Synthesis of Medhesive-107 (PEG20k-(GABMe)$_8$)

Added 10 g of 8-armed PEG-OH (20,000 MW; 4 mmol —OH), to 2.28 g of glutaric anhydride (20 mmol), 100 mL chloroform and 1.6 mL of pyridine taken in a round bottom flask equipped with a condensation column. Refluxed the mixture at 80° C. in an oil bath with Ar purging overnight. The polymer solution was cooled to room temperature, added 100 mL of chloroform. The reaction mixture was washed successively with 100 mL each of 12 mM HCl, saturated NaCl solution, and H$_2$O. The organic layer is then dried over MgSO$_4$ and filtered. Reduced the filtrate to around 100 mL and added to 900 mL of diethyl ether. Collected the precipitate via filtration and dried the precipitate. Dissolved the dried precipitate further with 80 mL of chloroform and 40 mL of DMF. Added 1.76 g of 3,4-dihydroxy benzylamine (8.0 mmol), 3.0 g of HBTU (8.0 mmol), 540 mg of HOBt (4.0 mmol), and 1.3 mL of triethylamine (9.6 mmol) to the mixture and stirred for 2 hours. The mixture was added to 900 mL of diethyl ether. The precipitate was collected via vacuum filtration and dried. The crude product was further purified through dialysis (3500 MWCO) in deionized H$_2$O (acidified to pH 3.5) for 48 hrs. After lyophilization, 3.75 g of Medhesive-107 was obtained. $^1$H NMR (400 MHz, D$_2$O): δ 6.88-6.76 (m, 3H, C$_6$H$_3$(OH)$_2$—), 4.27 (s, 2H, PEG-CH$_2$—O—C (O)—NH—), 3.79-3.52 (m, PEG), 3.36 (t, 2H, $C_6H_3(OH)_2$—$CH_2$—NH—C(O)—), 2.16 (m, 4H, $C_6H_3(OH)_2$—$CH_2$—NH—C(O)—$CH_2$—$CH_2$—$CH_2$—C(O)—O—), 1.74 (t, 2H, $C_6H_3(OH)_2$—$CH_2$—NH—C(O)—$CH_2$—$CH_2$—$CH_2$—C(O)—O—), UV-vis spectroscopy: 0.328±0.011 μmole DH/mg polymer (4.52±0.0016 wt % DH).

Synthesis of Medhesive-108 (PEG40K-(LysDH2)$_8$)

Combined 50 g of 8-arm PEG-OH (40,000 MW; 10 mmol —OH) and 100 mL of toluene in a 1500 mL round bottom flask equipped with a Dean-Stark apparatus, condensation column, and an Argon inlet. The mixture was stirred in a 160-165° C. oil bath until about ¾ of toluene was evaporated and collected with Argon purging. The reaction mixture was allowed to cool to room temperature and 225 mL of chloroform was added. 10.4 g of N,N'-α,ε-Bis-Boc-Lysine, 6.2 g of N,N'-dicyclohexylcarbodiimide, and 121.5 mg of 4-(Dimethylamino) pyridine were added and the reaction mixture was stirred in a room temperature water bath for overnight with Argon purging. Filtered the insoluble urea byproduct with coarse filter paper through vacuum filtration and filtrate was added to 1.25 L of diethyl ether for overnight at 4° C. After collecting and drying the precipitate, 41.65 g of PEG20k-(Boc$_2$Lyse)$_8$ was obtained. The polymer was dissolved in 80 mL of chloroform and 80 mL of TFA was slowly added. The mixture was stirred at room temperature for 30 min and added to 800 mL of diethyl ether. The mixture was placed in −20° C. for overnight and the supernatant was decanted. The gooey solid was precipitated again in chloroform/ether mixture and dried with vacuum pump. The solid was then dissolved in 520 mL of deionized water and dialyzed with 3500 MWCO dialysis tubes for two hours in 8 L of deionized water followed by 40 hrs in 10 L of water acidified to pH 3.5 with HCl, and 2 hrs in deionized water. After lyophilization, 20.17 g of PEG20k-(Lyse)$_8$ was obtained. The polymer was further dissolved with 120 mL of chloroform and 60 mL of DMF and 4.87 g of DOHA, 3.62 g of HOBt, 10.15 g of HBTU, and 3.745 mL of triethyl amine was added. The reaction mixture was stirred at room temperature for 1.5 hr and then added to 1.1 L of diethyl ether. The precipitate was collected with vacuum filtration and further purified with dialysis (3500 MWCO tubes in pH 3.5 water for 40 hrs and unbuffered water for 7 hrs) and freeze dried. 9.92 g of PEG40k-(LyseDH)$_8$ was obtained.

Synthesis of Medhesive-113 (PEG40k-(GADMe)$_8$

Added 50 g of 8-armed PEG-OH (40,000 MW; 10 mmol —OH), to 5.7 g of glutaric anhydride (50 mmol), 500 mL chloroform and 4 mL of pyridine taken in a round bottom flask equipped with a condensation column. Refluxed the mixture at 80° C. in an oil bath with Ar purging overnight. The polymer solution was cooled to room temperature, added 500 mL of chloroform. The reaction mixture was washed successively with 500 mL each of 12 mM HCl, saturated NaCl solution, and $H_2O$. The organic layer is then dried over $MgSO_4$ and filtered. Reduced the filtrate to around 500 mL and added to 8000 mL of diethyl ether. Collected the precipitate via filtration and dried the precipitate. Dissolved the dried precipitate further with 84 mL of chloroform and 56 mL of DMF. Added 2.22 g of dopamine-HCl (11.7 mmol) to the above. 5.08 g of HBTU (13.3 mmol), 1.8 g of HOBt (13.3 mmol), and 2.8 mL of triethylamine (20 mmol) are dissolved in 56 mL of DMF and added dropwise to the mixture and stirred for 1 hr. The mixture was added to 850 mL of diethyl ether. The precipitate was collected via vacuum filtration and dried. The crude product was further purified through dialysis (3500 MWCO) in deionized $H_2O$ (acidified to pH 3.5) for 48 hrs. After lyophilization, 15 g of Medhesive-113 was obtained. $^1$H NMR (400 MHz, $D_2O$): δ 6.77-6.61 (m, 3H, $C_6H_3(OH)_2$—), 4.18 (s, 2H, PEG-$CH_2$—O—C(O)—NH—), 3.76-3.49 (m, PEG), 3.36 (t, 2H, $C_6H_3(OH)_2$—$CH_2$—$CH_2$—NH—C(O)—), 2.65 (t, 2H, $C_6H_3(OH)_2$—$CH_2$—$CH_2$—NH—C(O)—), 2.16 (m, 2H, $C_6H_3(OH)_2$—$CH_2$—$CH_2$—NH—C(O)—$CH_2$—$CH_2$—$CH_2$—C(O)—O—), 2.16 (m, 2H, $C_6H_3(OH)_2$—$CH_2$—$CH_2$—NH—C(O)—$CH_2$—$CH_2$—$CH_2$—C(O)—O—), 1.74 (t, 2H, $C_6H_3(OH)_2$—$CH_2$—$CH_2$—NH—C(O)—$CH_2$—$CH_2$—$CH_2$—C(O)—O—), UV-vis spectroscopy: 0.229±0.003 μmole DM/mg polymer (3.49±0.0004 wt % DM).

Medhesives 77, 78, 80, 83, 85, 88, 99 and 100 can be prepared by the conditions provided above with the understanding that selection of the multihydroxy containing moieties are selected as required as well as the selection of PEGs.

Testing Protocols (Table 1)

Gel Time Measurement by Vial Tilt Method

200 μL of the polymer precursor was added to a 10 mm glass test tube. 200 μL of the crosslinking precursor was added to the test tube and the mixture was rapidly agitated for ~1 second on a vortexer. The test tube was then tilted every 5 seconds to observe the gross flow characteristics of the fluid. Gelation was defined as the absence of fluid flow when the vial is tilted. Concentrations of components were varied to determine optimal gelation times.

Gel Time Measurement by Stir Bar Method

A 5 mm×2 mm Teflon-coated stir bar was placed in a 10 mm test tube containing 100 μL of the polymer precursor solution. The stir bar was rotated at 300 rpm. 100 μL of the crosslinking precursor was added to the test tube. Gelation was defined as the time when the stir bar stopped spinning Concentrations of components were varied to determine optimal gelation times.

Equilibrium Swelling Method

Six 20 mL plastic scintillation vials were weighed (without the cap) and labeled and weights were recorded. Adhesive precursor solutions (1 mL each) were individually loaded into 3 mL disposable polypropylene syringes. Using a manual spray-type applicator (Micromedics, #SA-3674), the adhesive was expressed in a Teflon sheet in 1-2 cm drops. The adhesive drops were allowed to cure on the bench for 10 min. The gels were carefully placed in each of the vials and weighed. The weight of the vial was subtracted to arrive at the relaxed weight ($W_r$) of the gel. The gels were covered with 10 mL of phosphate-buffered saline and allowed to stand at room temperature for 24 h. The saline solution was aspirated and excess liquid in the vial was absorbed using a laboratory tissue. The vials containing the gels were reweighed to obtain the swollen weight ($W_s$). Swollen gels were placed in a vacuum dessicator overnight to remove water and were then reweighed to obtain dry weight ($W_d$). The volumetric swelling ratio (R) is calculated as follows:

$$R = \frac{V_s}{V_r}$$

$$V_s = \frac{W_d}{\rho_{PEG}} + \frac{W_s - W_d}{\rho_{Solvent}}$$

$$V_r = \frac{W_d}{\rho_{PEG}} + \frac{W_r - W_d}{\rho_{Solvent}}$$

where $\rho_{PEG}$ is the density of the polymer (1.123 g/mL) and $\rho_{Solvent}$ is the density of the solvent (1.123 g/mL for water).

Burst Strength Test Method

The burst strengths of various adhesive formulations were tested using a protocol based on ASTM Standard F 2392-04. In brief, collagen sausage casing (Vista International) was rinsed well in water and 0.1% sodium dodecyl sulfate to remove glycerin preservative. The collagen material was cut into 30 mm dia. circular pieces. In each piece a 3 mm circular defect was created on-center using a leatherworking punch. Adhesive formulations were applied to the collagen substrate inside a PFTE mask (inside diameter=15 mm). The adhesive gels were allowed to cure at ambient for 5 min and were then transferred to a 37° C. saline bath for one hour. Sealed defects were tested on a custom built apparatus consisting of a syringe pump, test fixture, and pressure gauge. The system was pressurized at 2 mL/min until the gel failed. The maximum pressure attained was recorded.

Compression Testing

To determine the compressive modulus and toughness of cured hydrogels, small (6.35 mm dia., 6.35 mm height; ~200 μL) cylinders of hydrogel material were prepared. Briefly, a thin layer of petroleum jelly was spread on a glass backing plate. A prefabricated PTFE mold (6.35 mm thick) containing 6.35 mm diameter holes was also coated with a thin layer of petroleum jelly. The back plate was then clamped to the mold. The adhesive precursors (polymer and crosslinker) were prepared and loaded into 3 mL syringes according to standard procedure. The hydrogel was expressed into holes in the mold filling them to the top. Any excess (e.g. overflow) was trimmed off with a scalpel before testing so that the hydrogel surface is flush with the top of the mold. Hydrogels were allowed to cure for 5 minutes on the bench. The mold was then unclamped from the glass plate, and the hydrogels were gently removed from the mold using a cotton swab. The cured hydrogels were place in PBS and incubated at 37° C. for 1 hour. Samples were tested in compression until failure at a strain rate of 10% min. Compressive modulus was calculated by measuring the slope of the resulting stress-strain curve between 0 and 10% strain. The compressive toughness was calculated by measuring the area under the stress-strain curve from 0% strain to maximum strain (i.e., strain at failure).

Tensile Testing

To determine the elastic modulus and toughness of cured hydrogels, "dog bone" shaped hydrogels material were prepared. Briefly, silicone molds and glass slides were sprayed with a mold release agent (Rocket Release, Stoner, Inc.) and allowed to dry for several minutes. The adhesive precursors (2.5 mL each) were prepared and loaded into 3 mL syringes. Precursors were expressed into the molds filling them to the top using slow, steady pressure to introducing air bubbles into the hydrogel. The molds containing the hydrogel material were quickly covered with the release-coated glass slide. Hydrogels were allowed to cure for 5 minutes on the bench. Using a metal spatula, the mold and glass slide were carefully separated. The hydrogel was gently removed from the mold using the metal spatula. The cured hydrogels were place in PBS and incubated at 37° C. for 1 hour. Use a strain rate of 10 mm/min and load until failure. Samples were tested in tension until failure at a strain rate of 10 mm/min. Elastic modulus was calculated by measuring the slope of the resulting stress-strain curve between 0 and 10% strain. The elastic toughness was calculated by measuring the area under the stress-strain curve from 0% strain to maximum strain (i.e., strain at failure).

TABLE 1

NERITES COMPOUND MECHANICAL PROPERTIES LIST

| Nerites Name | R&D Name | Lot# | Weight % | Component Vol. Ratio (Polymer:IO4-) | Component Conc. Ratio (IO4-:DHP) | Gelation Time, Spin Method (sec) |
|---|---|---|---|---|---|---|
| Medhesive-058 | PEG10k-(DOHA)$_6$ | 1451 | 15 | 1:1 | 0.5 | 104 +/− 8 |
| Medhesive-059 | PEG15k-(DOHA)$_6$ | 1475 | 15 | 1:1 | 0.4 | 54 +/− 7 |
| Medhesive-060 | PEG20k-(DOHA)$_6$ | 1455 | 15 | 1:1 | 0.4 | 30 +/− 1 |
| Medhesive-061 | (PEG20k-(DMu)8), ~62.5% coupling | | 15 | 1:1 | 0.5 | 30 +/− 4 |
| Medhesive-061 | (PEG20k-(DMu)8), 100% coupling | 2203 | 15 | 1:1 | 0.5 | 6 +/− 0 (JD_080530) |
| Medhesive-061 | (PEG20k-(DMu)8), 100% coupling | 2203 | 30 | 1:1 | 0.5 | 5.9 +/− 0.2 (LN002173) |
| Medhesive-061 | (PEG20k-(DMu)8), 100% coupling | 2220 | 30 | | | |
| Medhesive-061 | (PEG20k-(DMu)8), 100% coupling | 2236 | 15 | 1:1 | 0.5 | 8.3 +/− 1.5 (LN003017) |
| Medhesive-061 | (PEG20k-(DMu)8), 100% coupling | 2236 | 30 | 1:1 | 0.5 | 11.3 +/− 1.2 (LN003021) |
| Medhesive-061 | (PEG20k-(DMu)8), 98.92% coupling | 2247 | 15 | 1:1 | 0.5 | 10.3 +/− 1.2 (LN003051) |
| Medhesive-061 | (PEG20k-(DMu)8), 98.92% coupling | 2247 | 30 | 1:1 | 0.5 | 9.3 +/− 1.5 (LN003061) |
| Medhesive-063 | (PEG20k-(DH)8) | | 15 | 1:1 | 0.5 | 15 |

TABLE 1-continued

NERITES COMPOUND MECHANICAL PROPERTIES LIST

| | | | | | | |
|---|---|---|---|---|---|---|
| Medhesive-063 | (PEG20k-(DH)8) | 2216 | 30 | 1:1 | 0.5 | 24 +/− 0.6 (LN002175) |
| Medhesive-068 | PEG20k-(SADMe)8 | 2647 | 15 | 1:1 | 0.5 | 28 +/− 2.0 (LN003071) |
| Medhesive-069 | PEG20k-(GADMe)8 | 2633 | 15 | 1:1 | 0.5 | 22 +/− 1.0 (LN003046) |
| Medhesive-072 | PEG20k-(DMUrea)8 | 2259 | 15 | 1:1 | 0.5 | 10.3 +/− 2.9 (LN003064) |
| Medhesive-074 | PEG15k-(DMUrea)6 | 2271 | 15 | 1:1 | 0.5 | 14.0 +/− 4.0 (LN003067) |
| Medhesive-075 | | | 15 | 1:1 | 0.5 | 1 +/− 0 (LN003058) |
| Medhesive-082 | PEG40k-(Dmu)8, 99% Coupling | 2278 | 15 | 1:1 | 0.5 | 12.7 +/− 2.9 (LN003088) |
| Medhesive-086 | dpe-PEG15k-(DH)6 | 2372 | 15 | 1:1 | 0.5 | 31.3 +/− 3.8 (LN003083) |

| Nerites Name | Burst Strength (mmHg/mm Applied) | Swelling, (% Vol. Change), 37 deg C., PBS | Compressive Modulus | Compressive Toughness |
|---|---|---|---|---|
| Medhesive-058 | 141.8 +/− 8.0 (LN002145) | 30 +/− 3 | 70.84 +/− 17.68 (LN002119) | 32.63 +/− 5.45 (LN002119) |
| Medhesive-059 | 124.2 +/− 5.0 (LN002146) | 101 +/− 14 | 62.4 +/− 8.7 | 30.7 +/− 2.8 |
| Medhesive-060 | 104.2 +/− 3.2 (LN002132) | 162 +/− 16 | 26.8 +/− 14.5 (LN002133) | 16.6 +/− 8.8 (LN002133) |
| Medhesive-061 | 52.2 +/− 7.3 | 144 +/− 12 | | |
| Medhesive-061 | 163.3 +/− 11.3 (LN002148) | 27 +/− 7 | | |
| Medhesive-061 | 181.7 +/− 17.4 (LN002173) | | | |
| Medhesive-061 | | 54 +/− 7 (LN002182) | | |
| Medhesive-061 | 180.16 +/− 25.63 (LN003017) | | 88.18 +/− 29.12 (LN003002) | 45.16 +/− 14.57 (LN003002) |
| Medhesive-061 | 161.88 +/− 51.22 (LN003022) | | 12.28 +/− 9.43 (LN003019) | 46.98 +/− 17.84 (LN003018) |
| Medhesive-061 | 167.33 +/− 22.85 (LN003050) | 25 +/− 10% (LN003056) | 68.45 +/− 10.26 (LN003052) | 26.44 +/− 9.20 (LN003052) |
| Medhesive-061 | | 56 +/− 16% (LN003056) | | |
| Medhesive-063 | 131 +/− 21 | 71 +/− 12 | 39.8 +/− 9.1 | 27.1 +/− 8.9 |
| Medhesive-063 | 202.7 +/− 20.2 (LN002174) | 101 +/− 18 (LN002181) | 40.17 +/− 7.63 (LN003033) | 31.35 +/− 10.72 (LN003033) |
| Medhesive-068 | 131.28 +/− 18.3 (LN003077) | 103 +/− 8 (LN003075) | 55.47 +/− 9.10 (LN003079) | 26.30 +/− 11.6 (LN003079) |
| Medhesive-069 | 145.28 +/− 34.75 (LN003047) | 34 +/− 8% (LN003073) | 49.19 +/− 10.88 (LN003060) | 25.86 +/− 8.16 (LN003060) |
| Medhesive-072 | | 36 +/− 5% (LN006065) | | |
| Medhesive-074 | | | | |
| Medhesive-075 | | | | |
| Medhesive-082 | | | | |
| Medhesive-086 | | | | |

TABLE 2

Hydrogel formation and characterization of the hydrogels Medhesive 102 and 107.

| Polymer | Polymer Wt % | Gelation Time (s) | Percent Swelling | Burst Strength (mmHg) |
|---|---|---|---|---|
| Medhesive-102 | 15 | 15 ± 2.3 | 25 ± 6.0 | 169.3 ± 12.7 |
| Medhesive-107 | 15 | 35 ± 3.5 | 150 ± 28 | — |

Testing Protocols (Table 2)
Gelation and Characterization of the Adhesive Polymers
Gelation Time Determination A known amount of polymer is dissolved in 2× phosphate buffered saline at the desired concentration. A solution of sodium periodate is prepared at a concentration of 0.5 $IO_4^-$: DHP. 100 μL of polymer solution is pipetted into a test tube and stirred with a micro stir bar at 300 rpm. As 100 μL of the sodium periodate cross-linking solution is pipetted into the polymer solution, a timer is started. When the micro stir bar stops spinning, the timer is stopped, and the time is recorded. The gelation times from three samples are used to calculate a mean and standard deviation.

Percent Swelling

A known amount of polymer is dissolved in 2× phosphate buffered saline at the desired concentration and loaded into a 3 mL syringe. An additional 3 mL syringe is filled with a solution of sodium periodate prepared at a concentration of 0.5 $IO_4^-$: DHP. Both the polymer solution syringe and the sodium periodate syringe, in a volumetric ratio of 1:1 are connected to a y-adaptor and secured with a syringe holder and plunger lock. A spray tip is connected and a mixture of the two solutions is expressed onto the surface of a PTFE sheet. The hydrogels produced are allowed to cure for approximately 10 minutes, then are cut into 6 approximately equal pieces and placed into 6 glass vials. The relaxed weight of each polymer gel is collected. 10 mL of phosphate buffered saline is then added to each glass vial and the gels are allowed to swell at 37 degrees Celsius for 24 hours. After which, the phosphate buffered saline is decanted from the vials and the interior of the vial is dried. The swollen weight of the gel is collected. The swollen gels are then placed in a vacuum desiccator for 48 hours and weighed again. The percent volumetric swelling is then calculated.

Burst Strength Adhesion Test

Fresh collagen substrate is prepared by hydrating and washing in a mild detergent for 20 min. 40 mm circles are cut and a 2-mm circular defect is cut in the center of each circle. The samples are stored in phosphate buffered saline until use. A known amount of polymer is dissolved in 2× phosphate buffered saline at the desired concentration and loaded into a 3 mL syringe. An additional 3 mL syringe is filled with a solution of sodium periodate prepared at a concentration of 0.5 $IO_4^-$: DHP. Both the polymer solution syringe and the sodium periodate syringe, in a volumetric ratio of 1:1 are connected to a y-adaptor and secured with a syringe holder and plunger lock. The collagen substrates are placed on a petroleum coated PTFE sheet, and covered with a 3.5 cm diameter PTFE mask with a 1.5 cm hole. A spray tip is connected and a mixture of the two solutions is expressed into the PTFE mask hole. The sample is then covered with a petroleum coated glass slide, and a 100 gram weight is placed on top to ensure uniform thickness. The samples are allowed to cure approximately 10 minutes before they are placed in phosphate buffered saline at 37 degrees Celsius and incubated for one hour. The samples are then burst tested in accordance with ASTM F2392 entitled, "Standard Test Method for Burst Strength of Surgical Sealants". The pressure required to burst through the hydrogel was then recorded.

Effect of Acid and Base on Gelation Time of Adhesive Hydrogels

Figure 9:
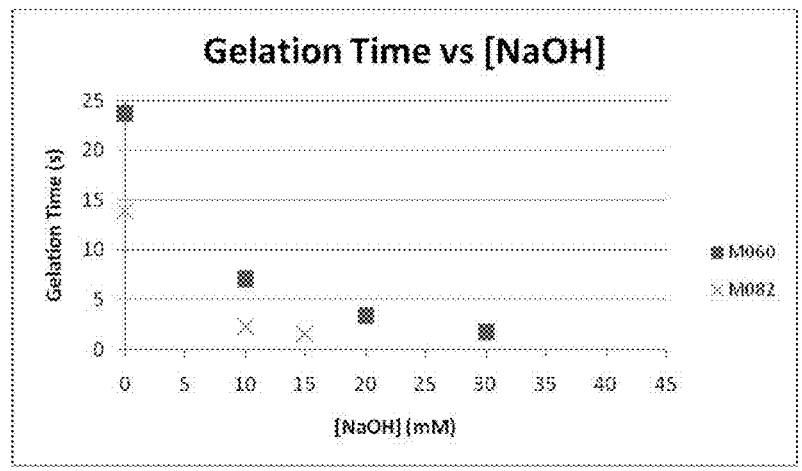
FIG. 9 provides a graphical representation of gelation time for two adhesives of the invention.

Solutions of Medhesive were prepared at different concentrations with buffers containing varying amounts of acid or base. The gelation time of each formulation was assessed. The results shown in Table 3 indicate that gelation time decreases proportionately with the addition of base and increases proportionately with the addition of acid. See also FIG. 9.

TABLE 3

Gelation Time of Polymers with buffers containing Acid or Base

| Medhesive | Wt % | Buffer | Gelation Time (Seconds) |
|---|---|---|---|
| M-069 | 15 | 2xPBS + 5 mM NaOH | 29 ± 3.1 |
| M-069 | 15 | 2xPBS + 10 mM NaOH | 11 ± 1.2 |
| M-069 | 15 | 2xPBS + 15 mM NaOH | 6.3 ± 2.3 |
| M-069 | 15 | 2xPBS + 20 mM NaOH | 2.7 ± 0.57 |
| M-069 | 15 | 2xPBS + 30 mM NaOH | 1.3 ± 0.57 |
| M-087 | 15 | 2xPBS + 5 mM NaOH | 2.6 ± 0.57 |
| M-087 | 15 | 2xPBS + 10 mM NaOH | 2.0 ± 0.0 |
| M-087 | 15 | 2xPBS + 15 mM NaOH | 1.0 ± 0.0 |
| M-087 | 30 | 2xPBS + 15 mM HCl | 54 ± 3.8 |
| M-087 | 30 | 2xPBS + 20 mM HCl | 74 ± 5.1 |
| M-087 | 30 | 2xPBS + 25 mM HCl | 110 ± 2 |
| M-087 | 30 | 2xPBS + 30 mM HCl | 140 ± 6.1 |
| M-102 | 15 | 2xPBS | 18 ± 0.90 |
| M-102 | 15 | 2xPBS + 15 mM NaOH | 2.6 ± 0.050 |
| M-102 | 15 | 2xPBS + 30 mM NaOH | 0.77 ± 0.070 |
| M-102 | 10 | 2xPBS + 15 mM NaOH | 2.5 ± 0.40 |
| M-102 | 20 | 2xPBS + 30 mM NaOH | 1.3 ± 0.30 |
| M-102 | 17.5 | 2xPBS + 30 mM NaOH | 1.2 ± 0.10 |
| M-102 | 10 | 2xPBS + 30 mM NaOH | 0.70 ± 0.10 |

2xPBS refers to double salt concentration.

Assessing Degradation Time of Adhesive Hydrogels

To assess the degradation time of adhesive hydrogels, polymer was weighed into a syringe and linked to another syringe containing the appropriate amount of buffer. The two syringes were mixed via a blending connector until the entire polymer was dissolved. A solution of $NaIO_4$ was prepared and loaded into a syringe. The mixed polymer syringe and the $NaIO_4$ syringe were connected to a Y-adapter and a spray tip, syringe holder, and plunger lock were attached. The Medhesive was then expressed onto a PTFE sheet and allowed to cure on the bench top for approximately 10 minutes. The hydrogels were then cut into pieces approximately 1 cm×1 cm. Each piece was then placed into a glass vial of known weight and the relaxed weight was collected. The polymer was then covered with 10 mL PBS and placed in an incubator, at a temperature of 37° C. or 55° C. Periodically the vials were removed, the water emptied, and then remaining gel weighed. The remaining gel was then dried under vacuum for 48 hours and weighed again. The change in mass was calculated.

Polymer Structure Dictates Rate of Degradation

Medhesives 87, 69, 68 and 102 were assessed for degradation time. The results shown in Table 4 indicate that different polymer structures provide different rates of degradation.

TABLE 4

Degradation Time of Different Polymers.

| Medhesive | 55° C. | 37° C. |
|---|---|---|
| M-069 | 7 Days | 63 Days |
| M-087 | 11-12 Days | ~3 Months |
| M-102 | 15 Days | ~3 Months |
| M-068 | 7 hrs | 26 hrs |

Assessing Sprayability of Adhesive Hydrogels

To assess the sprayability of hydrogels, polymer was weighed into a syringe and linked to another syringe containing an appropriate amount of buffer. The two syringes were mixed via a blending connector until the entire polymer was dissolved. A solution of $NaIO_4$ was prepared and loaded into a syringe. The mixed polymer syringe and the $NaIO_4$ syringe were connected to a Y-adapter and a spray tip, syringe holder and plunger lock were attached. The Medhesive assembly was then loaded into a custom built spray test bed. The desired speed, acceleration, sweep length, and dispensing rate are entered and the Medhesive was sprayed onto a piece of collagen, typically at a 90° angle. The drip length of any visible drips was then measured and averaged over a specified length of 20 centimeters.

Effect of Formulation on Sprayability of Medhesive

Medhesives 87, 69, and 102 were assessed for sprayability. The results shown in Table 5 indicate that formulating the polymer with different buffers and spraying the polymer at different angles changes the average drip length observed.

TABLE 5

Drip Length of Medhesive at various formulations

| Sample | Wt % Polymer Solutino | Angle | Distance |
|---|---|---|---|
| M-087 in 2xPBS + 4.5 mM NaOH | 15 | 30° | 1.48 cm |
| M-087 in 2xPBS + 6 mM NaOH | 15 | 30° | 1.06 cm |
| M-087 in 2xPBS + 7.5 mM NaOH | 15 | 30° | 0.488 cm |
| M-087 in 2xPBS + 7.5 mM NaOH | 15 | 90° | 2.97 cm |
| M-102 in 2xPBS + 15 mM NaOH | 15 | 90° | 1.13 cm |
| M-069 in 2xPBS + 30 mM NaOH | 15 | 90° | 0.18 cm |
| M-087 in 2xPBS + 15 mM NaOH | 15 | 90° | 0.49 cm |

Burst Pressure Performed on Intestine

Average burst pressures for different formulations of adhesive polymers tested is shown in Table 6, along with data spread and failure mode. For most compounds, brushing the adhesive over the defect seemed to increase the burst strength over spraying. Additionally, increasing the polymer concentration (weight percent) also increased burst strength.

Burst Testing Method Using Porcine Intestine

Porcine small intestines (Animal Technologies, Inc.) were rinsed and cut to 6-inch segments with mesentery tissue removed. A 2-3 mm perforation was made with a #11 scalpel blade on the side of the intestine opposite the mesentery tissue and sutured once with nylon 5-0 thread. Adhesive solution was applied by brush to the area of the defect and allowed to cure for 10 min. All samples were then hydrated in PBS (37° C.) for 1 hour. After which, intestine substrates were tied using umbilical tape to a burst tester consisting of threaded barbed fittings connected to a 60 mL air-filled syringe and pressure gauge. While the test setup was submerged underwater, air was pumped through the intestine at a rate of 20 mL/min until failure occurred, verified by the presence of bubbles emerging from the defect. Peak pressure and mode of failure were recorded.

TABLE 6

Burst pressures on porcine intestine for different adhesive formulations

| Medhesive Formulation | Average Burst Pressure (Std Dev) mmHg | Data Spread mmHg | Failure Mode |
|---|---|---|---|
| M060, 15 wt %, sprayed | 27.1 (17.6) | 9-61 | Not Recorded |
| M060, 15 wt %, painted | 31.4 (13.8) | 9-48 | 5/8 Cohesive |
| M060, 30 wt %, sprayed | 31.3 (10.4) | 15-45 | 6/8 Adhesive |
| M061, 30 wt %, sprayed | 29.1 (18.0) | 9-66 | 5/8 Adhesive |
| M061, 30 wt %, painted (15 mM HCl) | 60.3 (26.1) | 39-121 | 9/9 Cohesive |
| M061, 30 wt %, painted (17.5 mM HCl) | 64.1 (19.6) | 38-98 | 7/8 Cohesive |
| M063, 30 wt %, sprayed | 43.0 (7.3) | 34-53 | 8/8 Cohesive |
| M069, 30 wt %, painted | 27.5 (6.0) | 18-35 | 8/8 Cohesive |
| M082, 15 wt %, sprayed | 22.6 (8.7) | 11-36 | Not Recorded |
| M082, 30 wt %, painted (15 mM HCl) | 45.5 (15.0) | 22-64 | 6/6 Cohesive |

Preparation of Adhesive Blends

A multitude of additives were added to Medhesive polymers to create various adhesive blends. Each additive was dissolved in de-ionized water at a concentration of 100 mg/mL and diluted to a desired range with addition of 2xPBS (phosphate buffer solution with doubled salt concentration). Each Medhesive polymer was reconstituted at 30 or 60 wt % with its corresponding diluent solution (2x PBS+additive). Depending on the polymer, adhesive blends were formulated with dilute acid (0-17.5 mM HCl) to further tune the gelation time. The polymer solution was mixed with a solution of sodium periodate ($IO_4^-$:DHP molar ratio of 0.5) to cure.

Gelation of Adhesive Blends

Gelation time was determined by mixing adhesive blends with $NaIO_4$ solution using stir bar method as described above. As shown in Table 7, incorporation of additives such as polyvinylalchol (PVA) and carboxymethylcellulose (CMC) and 8-arm, 40k PEG-amine to Medhesive-061 did not dramatically increase the gelation time.

TABLE 7

Gelation time of various adhesive blends of Medhesive-061

| Medhesive Formulation | Gelation (s) |
|---|---|
| 15 wt % M061 | 8.98 ± 1.21 |
| M061 + 15 mg/mL PVA (31-50k) | 9.8 ± 2.29 |
| M061 + 30 mg/mL PVA (31-50k) | 9.11 ± 1.54 |
| M061 + 5 mg/mL PVA (89-98k) | 8.49 ± 1.17 |
| M061 + 10 mg/mL PVA (89-98k) | 9.60 ± 0.6 |
| M061 + 15 mg/mL PVA (89-98k) | 7.62 ± 0.37 |
| M061 + 0.5 mg/mL CMC | 8 ± 0.62 |
| M061 + 1 mg/mL CMC | 7.67 ± 0.19 |
| M061 + 2 mg/mL CMC | 7.31 ± 0.18 |
| M061 + 3 mg/mL CMC | 7.55 ± 0.33 |
| M061 + 4 mg/mL CMC | 9.42 ± 0.79 |
| M061 + 5 mg/mL CMC | 9.39 ± 1.76 |
| 15 wt % M061 | 8.7 ± 0.69 |
| M061 + 5 mg/mL pegamine | 8.5 ± 0.39 |
| M061 + 10 mg/mL pegamine | 8.2 ± 0.30 |
| M061 + 15 mg/mL pegamine | 8.1 ± 0.35 |
| M061 + 20 mg/mL pegamine | 8.7 ± 0.33 |
| M061 + 30 mg/mL pegamine | 9.1 ± 1.25 |
| M061 + 50 mg/mL pegamine | 9.4 ± 1.76 | and PVA blends with HCl

Gelation time of adhesive blends Medhesive-113 (15 and 30 wt %) with PVA is shown in Table 8. The blends were formulated with 7.5-15 mM of HCl. The gelation time was lengthened with increased HCl content.

TABLE 8

Gelation time of adhesive blends of Medhesive-113 and PVA

| Wt % | Formulation | Gelation Time (sec) |
|---|---|---|
| 15% | 2XPBS | 23.5 ± 3.30 |
| 15% | 2XPBS w/7.5 mM HCl & 10 mg/ml PVA (89-98K) | 55.5 ± 6.29 |
| 15% | 2XPBS w/11.25 mM HCl & 10 mg/ml PVA (89-98K) | 141 ± 8.83 |
| 30% | 2XPBS w/7.5 mM HCl & 10 mg/ml PVA (89-98K) | 34.8 ± 2.01 |
| 30% | 2XPBS w/11.25 mM HCl & 10 mg/ml PVA (89-98K) | 52.8 ± 1.96 |
| 30% | 2XPBS w/15 mM HCl & 10 mg/ml PVA (89-98K) | 102 ± 0.900 |
| 30% | 2XPBS w/15 mM HCl & 10 mg/ml PVA (89-98K) | 73.1 ± 5.19 |

Medhesive-061 and PVA Blends

Figure 2:
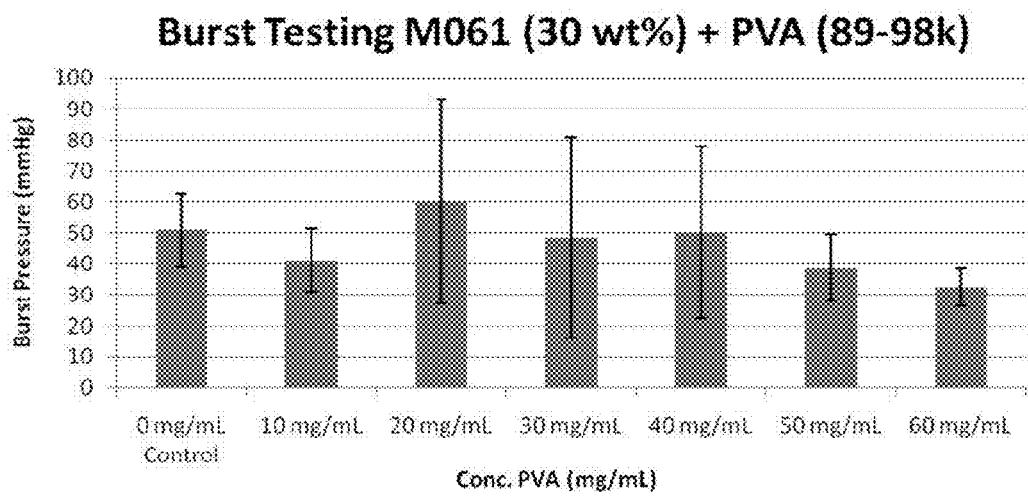
FIG. 2 shows burst pressures of 30 wt % M061+different concentrations 89-98 k PVA.

Burst test was performed on a blend of Medheisve-061 (30 wt %, with 15-17.5 mM HCl) with polyvinyl alcohol (PVA, MW=89-98 kDa) at a final PVA concentration of 0-60 mg/mL in 2×PBS using porcine intestines as the test substrate. Solution also contains 15-17.5 mM HCl to slow the curing time. As shown in FIG. 2, PVA did not strongly increased the maximum burst pressure, which decreased at elevated PVA concentrations.

Medhesive-082 and PVA Blends

Figure 3:
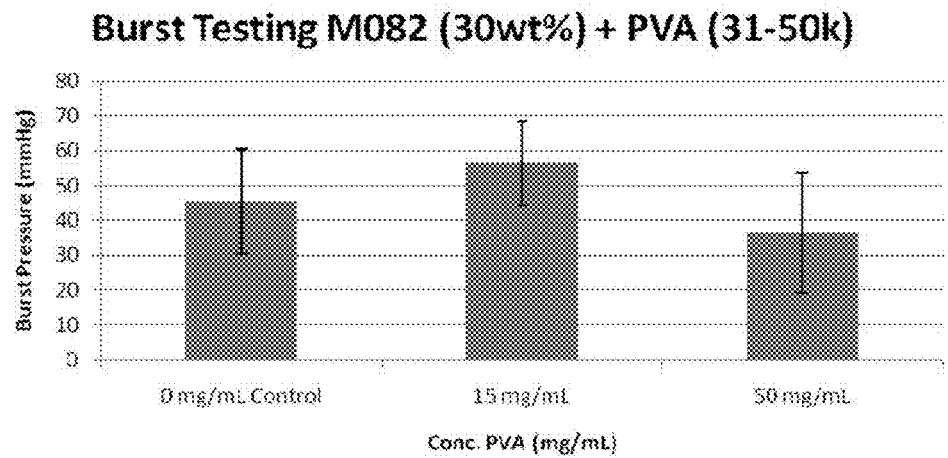
FIG. 3 provides burst pressures of 30 wt % M082+different concentrations of 31-50 k PVA.
Figure 4:
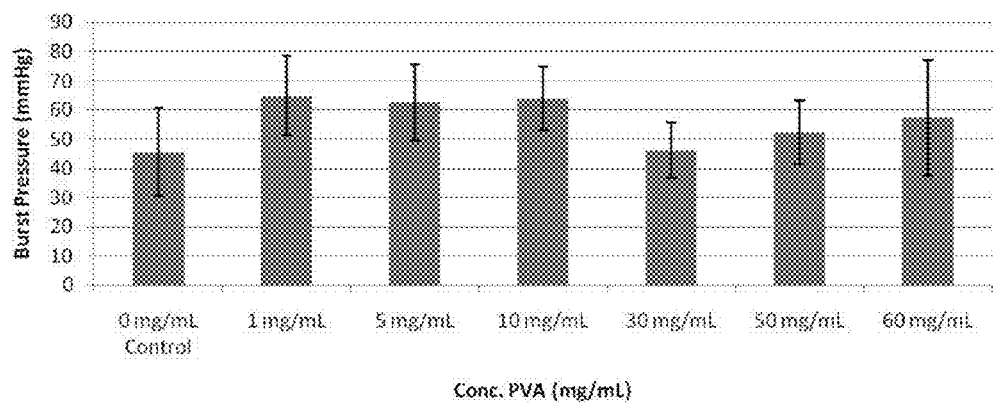
FIG. 4 shows burst pressures of 30 wt % M082+different concentrations of 89-98 k PVA.

Burst test was performed on a blend of Medheisve-082 (30 wt %, 15 mM HCl) with PVA at a final PVA concentration of 0-60 mg/mL using porcine intestines as the test substrate. Incorporation of 15 mg/mL PVA (31–50 kPa) resulted in an increase in the burst pressure which decreased with a further increase in PVA content (FIG. 3). Similarly, maximum burst pressures were the highest at a lower content of higher molecular weight PVA (89-98 kDa at 1-10 mg/mL) (FIG. 4). With further increase in the PVA concentration, a slightly lowered burst pressures was observed. Precipitation of PVA at elevated concentration (above 10 mg/mL) may have affected the lower recorded pressure.

Medhesive-113 and PVA Blends

Figure 5:
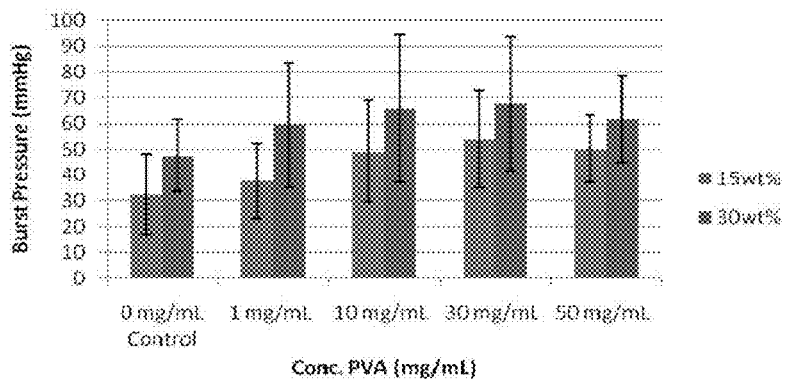
FIG. 5 provides burst pressures of 15 and 30 wt % M113+ different concentrations of 89-98 k PVA.

Burst test was performed on a blend of Medheisve-113 (15 mM HCl) with PVA at a final PVA concentration of 0-50 mg/mL using porcine intestines as the test substrate. FIG. 5 shows that by increasing the concentration of PVA, burst pressure also increased for both 15 and 30 wt % polymer solution. At the higher PVA concentrations (30-50 mg/mL), some of the additive precipitates out of solution.

Medhesive-113 and Sorbitol Blends

Figure 6:
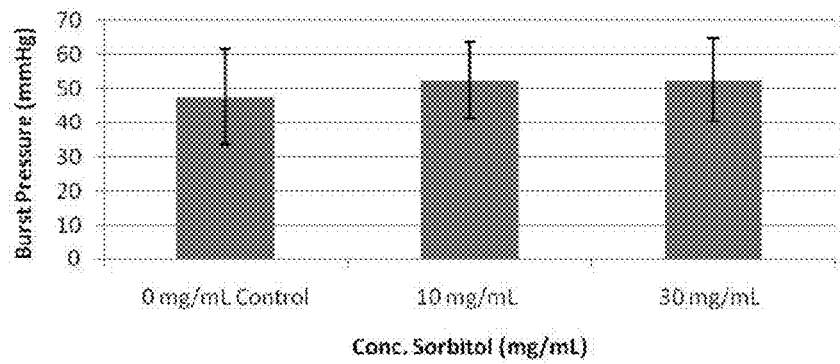
FIG. 6 depicts burst pressure of 30 wt % M113 plus Sorbitol.

Burst test was performed on a blend of (30 wt %) with sorbitol at a final sorbitol concentration of 0-30 mg/mL using porcine intestines as the test substrate. FIG. 6 shows a slight increase in burst pressure with the addition of Sorbitol.

Medhesive-113 and Dopa-Pluronic

Figure 7:
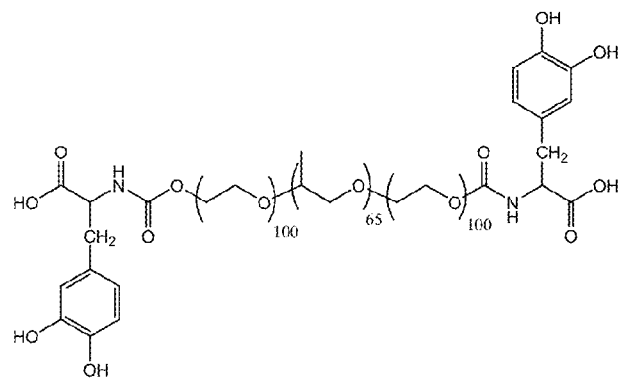
FIG. 7 is a depiction of a DOPA-Pluronic.
Figure 8:
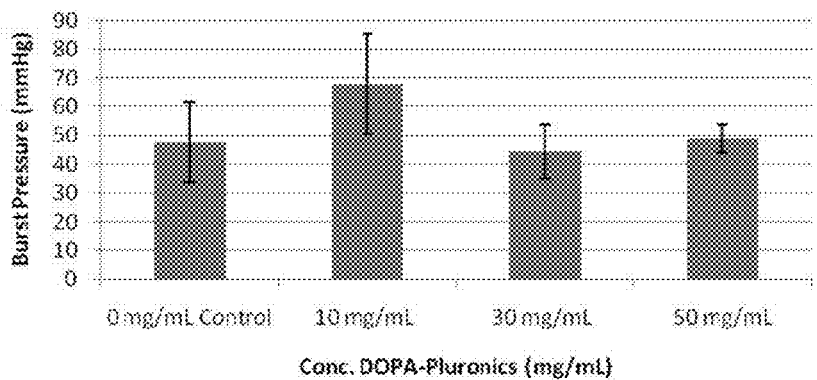
FIG. 8 provides burst pressure of 30 wt % M113 plus DOPA-Pluronics.

Burst test was performed on a blend of Medheisve-113 (30 wt %, 15 mM HCl) with DOPA-Pluronic (0-50 mg/mL, FIG. 7) using porcine intestines as the test substrate. As shown in FIG. 8, burst pressure increased with adding a small amount of DOPA-Pluronic (10 mg/mL). However, burst pressure was not affected when a higher concentrations of the DOPA-Pluronic was used.

Patterned Adhesive Coating of Mesh for Accelerated Mesh-Tissue Integration

Figure 10:
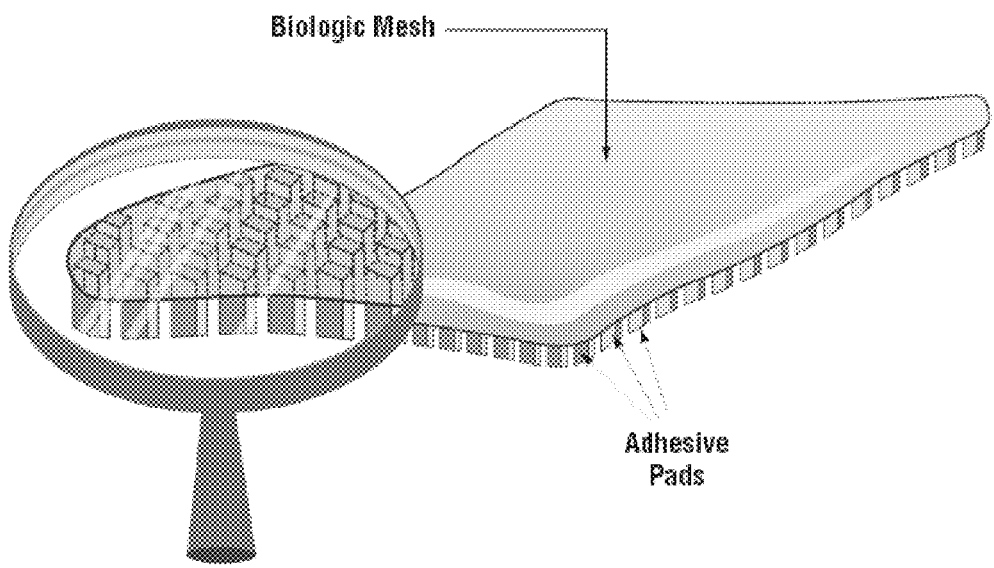
FIG. 10 provides a mesh coated with adhesive pads.
Figure 11:
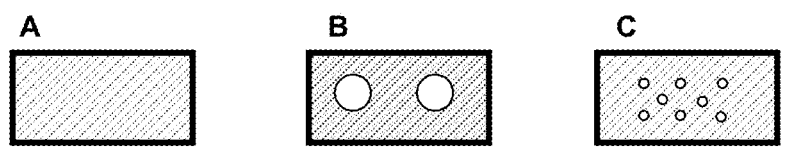
FIG. 11 provides chematics of A) construct with 100% area coverage, B) a patterned construct with 2 circular uncoated areas with larger diameter, and C), a patterned construct with 8 circular uncoated areas with smaller diameter.

The adhesive polymer can be coated on the mesh in a pattern to promote faster integration of the host tissue and mesh. Unlike other fixation methods, adhesives may act as a barrier for tissue ingrowth into the mesh if their degradation rate is slower than the cell invasion rate and subsequent graft incorporation. Meshes secured with a slow degrading adhesive such as cyanoacrylate demonstrated impaired tissue integration. For meshes secured with conventional methods, the tensile strength of the mesh-tissue interface reached a maximum within four weeks after implantation, indicating that the meshes were fully integrated with the host tissue. This suggests that cellular infiltration occurs earlier. While the adhesive polymers of the invention exhibit a variety of degradation profiles, some formulations may take several months to be completely absorbed. To ensure rapid tissue integration into the mesh while maintaining strong adhesion at the time of implantation, adhesives can be coated onto a mesh in an array of adhesive pads, leaving other areas of the mesh uncoated as shown in FIG. 10. Other patterns with various geometric shapes (circular, rectangular, etc.) can also be created FIG. 11. The regions coated with adhesive will provide the initial bonding strength necessary to secure the mesh in place, while the uncoated regions will provide an unobstructed path for cellular invasion and tissue ingrowth to immediately Occur.

To create a patterned adhesive polymer coating, a solvent casting method could be used, in which a metallic lattice will be placed over the mesh while the polymer solution is drying. The lattice will be used to displace the polymer solution so that an uncoated region is formed as the solution dries. By controlling the dimensions (5-10 mm) and the thickness (0.2-1.0 mm) of the lattice, it is possible to vary the ratio of the surface areas of the coated and uncoated regions. Bovine pericardium will be used both as the surrogate backing and test substrate. Lap shear adhesion testing will be performed to determine the effect of the patterned coating on the adhesive properties of the bioadhesive construct. For each coating pattern, a minimum of 10 repetitions will be tested, and statistical analysis will be performed using ANOVA, the Tukey post hoc analysis, and a significance level of p=0.05.

It is expected that a patterned adhesive can be easily achieved using the described method. The adhesive strength of the patterned coating will likely be slightly lower compared to the non-patterned adhesive coating since the overall surface area of the adhesive is decreased. By varying the ratio of the surface areas between the coated and uncoated regions, the surface can be tailored adjust for the initial adhesive strength to the rate of tissue ingrowth. A pattern that results in greater than 80% of the adhesive strength of the non-patterned coating will be selected for subsequent animal studies. The rate of tissue ingrowth will be determined by implanting both patterned and non-patterned bioadhesive constructs into a rabbit model.

Medhesive Coatings

TiO2 coated silicon substrates were cut into 8 mm×8 mm squares with a diamond cutter. Substrates were cleaned using 10 min sonication cycles of 5% phosphate free detergent, deionized water, acetone and 2-propanol. Substrates were then immersed in aqueous coating solutions containing one of the Medhesive compounds listed in Table 9 for 24 hours at the lower critical solution temperature (LCST). Coated samples were then rinsed twice with ultra-pure deionized water and inoculated with a 1×105 suspension of S. aureus in Tryptic Soy Broth (TSB). After 24 hours in culture at 37° C. on a plate shaker, substrates were rinsed in sterile 1×PBS to remove any non-adherent bacteria and swabbed with two sterile cotton-tipped applicators. The swabs were placed into 5 mL sterile 1× PBS for sonication and vortexing. Serial dilutions of the resulting suspension were made and 100 μL of each suspension was plated onto Tryptic Soy Agar (TSA) plates for overnight incubation at 37° C. Bacterial counts for each substrate were obtained, normalized to the surface area, and compared to uncoated TiO2 controls.

TABLE 9

Percent Reduction of S. aureus on Medhesive-coated TiO2 substrates

| Polymer | # Arms, MW | Reduction on TiO2 Substrates |
|---|---|---|
| Medhesive-058 | 6-arm, 10k | −63% |
| Medhesive-059 | 6-arm, 15k | −45% |
| Medhesive-060 | 6-arm, 20k | −76% |
| Medhesive-061 | 8-arm, 20k | −60% |
| Medhesive-063 | 8-arm, 20k | −82% |
| Medhesive-068 | 8-arm, 20k | −75% |
| Medhesive-069 | 8-arm, 20k | −77% |
| Medhesive-072 | 8-arm, 20k | −70% |
| Medhesive-074 | 6-arm, 15k | −30% |
| Medhesive-075 | 8-arm, 20k | −83% |
| Medhesive-081 | 8-arm, 20k | −51% |
| Medhesive-082 | 8-arm, 40k | −89% |
| Medhesive-084 | 6-arm, 15k | −81% |
| Medhesive-086 | 6-arm, 15k | −69% |
| Medhesive-087 | 8-arm, 20k | −2% |
| Medhesive-088 | 8-arm, 20k | −80% |
| Medhesive-089 | 8-arm, 20k | −75% |
| Medhesive-090 | 8-arm, 20k | 0% |
| Medhesive-094 | 8-arm, 20k | pos. 20% |
| Medhesive-095 | 8-arm, 20k | −78% |
| Medhesive-100 | 8-arm, 20k | −80% |
| Medhesive-101 | 8-arm, 20k | −91% |
| Medhesive-102 | 8-arm, 20k | −84% |
| Medhesive-103 | 8-arm, 20k | −95.70% |
| Medhesive-107 | 8-arm, 20k | −86.50% |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound comprising formula (I):

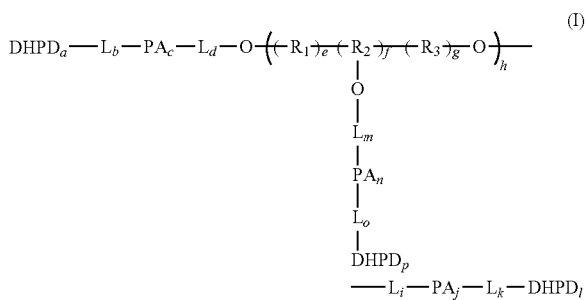

wherein each $DHPD_a$, $DHPD_l$, $DHPD_p$, independently, can be the same or different;

each $L_b$, $L_k$, and $L_o$ is;

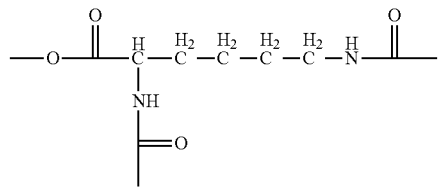

each $L_d$, $L_i$ and $L_m$ represent a bond between an O and PA;

each $PA_c$, $PA_j$ and $PA_n$, independently, can be the same or different;

e is a value from 1 to about 3;

f is a value from 1 to about 10;

g is a value from 1 to about 3;

h is a value from 1 to about 10, wherein f+h is a value from 6 to about 20;

each of $R_1$, $R_2$ and $R_3$, independently, is a branched or unbranched alkyl group having at least 1 carbon atom;

each PA, independently, is a poly(alkylene oxide) polyether having a molecular weight between about 1,500 and about 5,000 daltons; and each DHPD, independently, is a dopamine, 3,4-dihydroxyphenylalanine, 3,4-dihydroxyphenyl ethanol or 3,4-dihydroxyhydrocinnamic acid residue.

2. The compound of claim 1, wherein each $PA_c$, $PA_j$, and $PA_n$ is a polyethylene glycol polyether.

3. The compound of claim 1, wherein each $L_b$, $L_k$, and $L_o$ are amide linkages and $L_d$, $L_i$ and $L_m$ represent ether bonds 4. The compound of claim 1, wherein e and g each have a value of 1 and f is 4 or 6.

5. The compound of claim 1, wherein h is 1.

6. The compound of claim 1, wherein each $DHPD_a$, $DHPD_l$, $DHPD_p$ is a 3,4-dihydroxyhydrocinnamic acid residue;

each $L_d$, $L_i$ and $L_m$ represent ether bonds;

each $PA_c$, $PA_j$, and $PA_n$ are polyethylene glycol polyether derivatives comprising a hydroxyl terminal residue, each having a molecular weight of between about 1,500 and about 5,000 daltons;

e is 1;

f is 1;

g is 1; and h is 6.

7. A compound comprising formula (I):

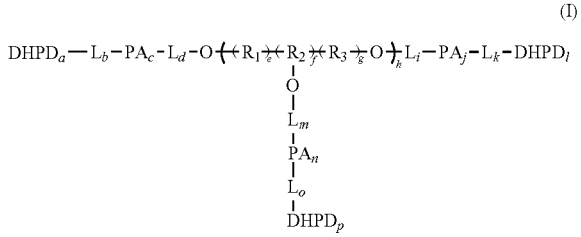

wherein each $DHPD_a$, $DHPD_l$, $DHPD_p$ is a dihydroxyhydrocinnamic acid residue;

each $L_b$, $L_k$, and $L_o$ form amide linkages between a 3,4-dihydroxyhydrocinnamic acid residue and the primary amines of a lysine residue and an ester linkage between a carboxylic acid of said lysine residue and a terminal portion of a polyethylene glycol polyether;

each $L_b$, $L_k$, and $L_o$, independently, can be the same or different;

each of $L_d$, $L_i$, and $L_m$ represent ether bonds;

each $PA_c$, $PA_j$, and $PA_n$ are polyethylene glycol polyether derivatives comprising a hydroxyl terminal residue, each having a molecular weight of between about 1,500 and about 3,500 daltons;

each $PA_c$, $PA_j$, and $PA_n$, independently, can be the same or different;

wherein e, f and g each have a value of 1; and h is 6.

8. The compound of claim 7, wherein each $L_b$, $L_k$, and $L_o$ is

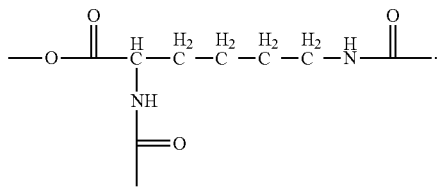

9. A compound comprising formula (I):

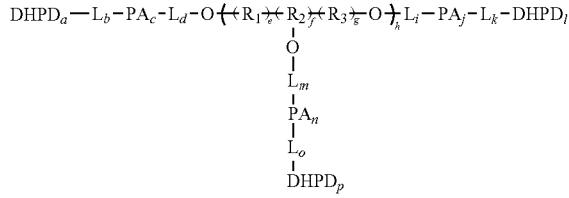

wherein each $DHPD_a$, $DHPD_l$, $DHPD_p$ is a dihydroxyhydrocinnamic acid residue;

each, $L_b$, $L_k$, and $L_o$, form an ester linkage between a 3,4-dihydroxyhydrocinnamic acid residue and a 3-amino-1,2-propandiol hydroxyl residues and a urethane linkage between an amine of a 3-amino-1,2-propandiol residue and a terminal portion of a polyethylene glycol polyether;

each $L_b$, $L_k$, and $L_o$, independently, can be the same or different;

each of $L_d$, $L_i$, and $L_m$ represent ether bonds;

each $PA_c$, $PA_j$, and $PA_n$ are polyethylene glycol polyether derivatives comprising a hydroxyl terminal residue, each having a molecular weight of between about 1,500 and about 3,500 daltons;

each $PA_c$, $PA_j$, and $PA_n$, independently, can be the same or different;

wherein e, f and g each have a value of 1; and h is 6.

10. The compound of claim 9, wherein each $L_b$, $L_k$, and $L_o$ is

11. A compound comprising formula (I):

wherein each $DHPD_a$, $DHPD_l$, $DHPD_p$ is a dopamine residue;

each $L_b$, $L_k$, and $L_o$ form a urethane linkage between an amine on a dopamine residue and a terminal portion of a polyethylene glycol polyether;

each $L_b$, $L_k$, and $L_o$, independently, can be the same or different;

each $L_d$, $L_i$, and $L_m$ represent ether bonds;

each $PA_c$, $PA_j$, and $PA_n$ are polyethylene glycol polyether derivatives comprising a hydroxyl terminal residue, each having a molecular weight of between about 1,500 and about 3,500 daltons;

each $PA_c$, $PA_j$, and $PA_n$, independently, can be the same or different;

wherein e, f and g each have a value of 1; and h is 6.

12. The compound of claim 11, wherein each $L_b$, $L_k$, and $L_o$ is

* * * * *